(12) United States Patent
Gengenbach et al.

(10) Patent No.: US 6,222,099 B1
(45) Date of Patent: *Apr. 24, 2001

(54) TRANSGENIC PLANTS EXPRESSING MAIZE ACETYL COA CARBOXYLASE GENE AND METHOD OF ALTERING OIL CONTENT

(75) Inventors: Burle G. Gengenbach, St. Paul; David A. Somers, Roseville; Donald L. Wyse, Wyoming; John W. Gronwald, Shoreview; Margaret A. Egli, Roseville; Sheila M. Lutz, St. Paul, all of MN (US)

(73) Assignees: Regents of the University of Minnesota, Minneapolis, MN (US); The United States of America, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/930,285

(22) PCT Filed: Apr. 4, 1996

(86) PCT No.: PCT/US96/04625

§ 371 Date: Apr. 13, 1998

§ 102(e) Date: Apr. 13, 1998

(87) PCT Pub. No.: WO96/31609

PCT Pub. Date: Oct. 10, 1996

Related U.S. Application Data

(63) Continuation-in-part of application No. 08/417,089, filed on Apr. 5, 1995, now Pat. No. 6,069,298, which is a continuation-in-part of application No. 08/014,326, filed on Feb. 5, 1993, now Pat. No. 5,498,544.

(51) Int. Cl.[7] .............................. A01H 5/00; A01H 5/10; C12N 15/82
(52) U.S. Cl. .................. 800/298; 435/320.1; 800/281
(58) Field of Search .................. 435/320.1, 69.1, 435/419, 468; 536/23.2, 23.6; 800/281, 298

(56) References Cited

U.S. PATENT DOCUMENTS

| | | | |
|---|---|---|---|
| 4,326,358 | 4/1982 | Lawrence, Jr. et al. | 47/58 |
| 4,731,499 | 3/1988 | Puskaric et al. | 800/1 |
| 4,761,373 | 8/1988 | Anderson et al. | 435/172.3 |
| 4,874,421 | 10/1989 | Kleschick et al. | 71/9 H |
| 4,940,835 | 7/1990 | Shah et al. | 800/205 |
| 5,107,065 | 4/1992 | Shewmaker et al. | 800/205 |
| 5,162,602 | 11/1992 | Somers et al. | 800/235 |
| 5,190,931 | 3/1993 | Inouye | 435/91 |
| 5,290,696 | 3/1994 | Somers et al. | 436/240.5 |
| 5,498,544 | 3/1996 | Gengenbach et al. | 435/320.1 |
| 5,500,361 | 3/1996 | Kinney | 435/172.3 |
| 5,510,474 * | 4/1996 | Quail et al. | 536/24.1 |
| 5,530,186 | 6/1996 | Hitz et al. | 800/205 |
| 5,539,092 | 7/1996 | Haselkorn et al. | 536/23.2 |
| 5,559,220 | 9/1996 | Roessler et al. | 536/23.6 |
| 5,608,152 | 3/1997 | Kridl et al. | 800/205 |
| 5,689,045 | 11/1997 | Logemann et al. | 800/205 |
| 5,767,362 | 6/1998 | Best et al. | 800/205 |
| 5,767,363 | 6/1998 | De Silva et al. | 800/205 |
| 5,792,627 | 8/1998 | Haselkorn et al. | 435/69.1 |
| 5,801,233 | 9/1998 | Haselkorn et al. | 536/23.6 |
| 5,854,420 | 12/1998 | Ashton et al. | 800/205 |

FOREIGN PATENT DOCUMENTS

| | | | |
|---|---|---|---|
| 42 34 131 | 4/1994 | (DE) | A01H/5/00 |
| 0 270 356 A2 | 6/1988 | (EP) | C12N/15/00 |
| 0 469 810 A1 | 2/1992 | (EP) | C07K/13/00 |
| 1 720 594 | 3/1992 | (SU) | A01H/1/02 |
| 89/07647 | 8/1989 | (WO) | C12N/15/00 |
| 93/11243 | 6/1993 | (WO) | C12N/15/52 |
| 94/08016 | 4/1994 | (WO) | C12N/15/52 |
| 94/17188 | 8/1994 | (WO) | C12N/15/52 |
| 94/23027 | 10/1994 | (WO) | C12N/15/11 |
| 94/29467 | 12/1994 | (WO) | C12N/15/82 |
| 95/06128 | 3/1995 | (WO) | C12N/15/82 |
| 95/29246 | 11/1995 | (WO) | C12N/15/82 |

OTHER PUBLICATIONS

Stam M, et al. "The silence of genes in transgenic plants." Ann. Bot. 79: 3–12, 1997.*
Koziel MG, et al. "Optimizing expression of transgenes with an emphasis on post–transcriptional events." Plant Mol. Biol. 32: 393–405, 1996.*
Smith CJS, et al. "Antisense RNA inhibition of polygalacturonase gene expression in transgenic tomatoes." Nature 334: 724–726, Aug. 25, 1988.*
Elborough, K.M., et al., "Studies on Wheat Acetyl CoA Carboxylase and the Cloning of a Partial cDNA", *Plant Molecular Biology*, 24, pp. 21–34, (1994).
Alrefai, R., et al., "Quantitative Trait Locus Analysis of Fatty Acid Concentrations in Maize", *Genome*, 38, 894–901, (1995).
Lutz, S.M., et al., "Characterization of Two Acetyl–CoA Carboxylase Genes from Maize", *Abstracts, International Meeting on Plant Lipids*, Paris, France, 1 p., (Jun. 1994).
Lutz, S.M., et al., "Genomic Mapping of Acetyl–CoA Carboxylase Clones and Herbicide Resistance in Maize", *Proceedings of the 1993 Plant Lipid Symposium*, Minneapolis, MN, p. 10, (Jul. 29–31, 1993).
Roessler, P., "Expression of an Algal Acetyl–CoA Carboxylase Gene in *E. Coli* and Yeast", *Abstracts, 11th International Lipid Meeting*, Paris, France, (Jun. 1994).

(List continued on next page.)

Primary Examiner—Amy J. Nelson
(74) Attorney, Agent, or Firm—Schwegman, Lundberg, Woessner & Kluth, P.A.

(57) ABSTRACT

The present invention provides a complete cDNA sequence and partial DNA sequences encoding maize acetyl CoA carboxylase and methods for altering the oil content of plants by introducing and expressing a maize acetyl CoA carboxylase gene in plant cells.

34 Claims, 29 Drawing Sheets

OTHER PUBLICATIONS

Roessler, R.G., et al., "Expression of an Algal Acetyl–CoA Carboxylase Gene in *E. Coli*", In: *Plant Lipid Metabolism*, Kader, J.–C., et al., (eds.), Kluwer Academic Publishers, The Netherlands, p. 46–48, (1995).

Al–Feel, W., et al., "Cloning of the Yeast *FAS3* Gene and Primary Structure of Yeast Acetyl–CoA Carboxylase", *Proc. Natl. Acad. Sci. USA*, 89, 4534–4538 (May 1992).

Anderson, P.C., et al., "Cell Culture Selection of Herbicide Tolerant Corn", Agronomy Abstract, Division C–1—Crop Breeding, Genetics and Cytology, ASA, Madison, WI, p. 56 (1985).

Anderson, P.C., et al., "Selection of an Imidazolinone Tolerant Mutant of Corn", *Abstracts, Sixth International Congress on Plant Tissue Cell Culture*, Minneapolis, MN, p. 437 (Aug. 4–8, 1986).

Ashton, A.R., et al., "Molecular Cloning of Two Different cDNAs for Maize Acetyl CoA Carboxylase", *Plant Molecular Biology*, 24, 35–49 (1994).

Bai, D.H., et al., "Molecular Cloning of cDNA for Acetyl–Coenzyme A Carboxylase", *Journal of Biological Chemistry*, 261, 12395–12399 (Sep. 15, 1986).

Bettey, M., et al., "Purification and Characterization of Acetyl CoA Carboxylase from Developing Pea Embryos", *J. Plant Physiol.*, 140, 513–520 (1992).

Botterman, J., et al., "Engineering Herbicide Resistance in Plants", *Trends in Genetics*, 4, 219–222 (Aug. 1988).

Bowman, T.R., et al., "Selection for Resistance to Paraquat in Maize Embryogenic Cell Cultures", *Abstracts, Sixth International Congress on Plant Tissue Cell Culture*, Minneapolis, MN, Abstract No. 85, p. 73 (Aug. 4–8, 1986).

Caffrey, J.J., et al., "Genetic Mapping of Two Acetyl–CoA Carboxylase Genes", *Maize Genetics Cooperation Newsletter*, 69, 3–4 (1995).

Charles, D.J., et al., "Characterization of Acetyl–CoA Carboxylase in the Seed of Two Soybean Genotypes", *Phytochemistry*, 25, 55–59 (1986).

Charles, D.J., et al., "Purification and Characterization of Acetyl–CoA Carboxylase from Developing Soybean Seeds", *Phytochemistry*, 25, 1067–1071 (1986).

D'Halluin, K., et al., "Transgenic Maize Plants by Tissue Electroporation", *The Plant Cell*, 4, 1495–1505 (Dec. 1992).

Darnell, J., et al., In: *Molecular Cell Biology, Revised*, Scientific American Books, Inc., New York, p. 248–257 (1986).

Dimroth, P., et al., "Crystallization of Biotin Carboxylase, a Component Enzyme of the Acetyl–CoA Carboxylase System from *Escherichia coli*", *Hoppe–Seyler's Z. Physiol. Chem.*, 352, 351–354 (Mar. 1971).

Egin–Buhler, B., et al., "Improved Purification and Further Characterization of Acetyl–CoA Carboxylase from Cultured Cells of Parsley (*Petroselinum hortense*)", *Eur. J. Biochem.*, 133, 335–339 (1983).

Egli, M., et al., "Cloning and Expression of Maize Acetyl–CoA Carboxylase", *Agronomy Abstracts*, 1992 Annual Meeting, Minneapolis, MN, p. 189 (1992).

Egli, M., et al., "Purification and Characterization of Maize Acetyl–CoA Carboxylase", *Plant Physiology*, 96S, p. 92 (1991).

Egli, M.A., et al., "A 233–kD Subunit of Acetyl–CoA Carboxylase is Encoded by the Maize Acc–1 Gene", *Maize Genetics Cooperation Newsletter*, 66, 94 (1992).

Egli, M.A., et al., "A Maize Acetyl–CoA Carboxylase cDNA Maps to Chromosome 2S", *Plant Physiology*, 105S, Abstract No. 311, p. 64 (1994).

Egli, M.A., et al., "A Maize Acetyl–Coenzyme A Carboxylase cDNA Sequence", *Plant Physiology*, 108, 1299–1300 (1995).

Egli, M.A., et al., "Characterization of Maize Acetyl–Coenzyme A Carboxylase", *Plant Physiology*, 101, 499–506 (1993).

Egli, M.A., et al., "Cloning and Sequence Analysis of a Maize Acetyl–CoA Carboxylase Gene", *Plant Physiology*, 102S, Abstract No. 384, p. 70 (1993).

Egli, M.A., et al., "Identification and Mapping of Maize Acetyl–CoA Carboxylase Genes", *Maize Genetics Cooperation Newsletter*, 68, 92–93 (Mar. 15, 1994).

Egli, M.A., et al., "Purification of Maize Leaf Acetyl CoA Carboxylase", *Maize Genetics Cooperation Newsletter*, 65, p. 95 (1991).

Elborough, K.M., et al., "Isolation of cDNAs from *Brassica napus* Encoding the Biotin–Binding and Transcarboxylase Domains of Acetyl–CoA Carboxylase: Assignment of the Domain Structure in a Full–Length *Arabidopsis thaliana* Genomic Clone", *Biochem. J.*, 301, 599–605 (1994).

Fawcett, J.A., et al., "Influence of Environment on Corn (*Zea mays*) Tolerance to Sethoxydim", *Weed Science*, 35, 568–575 (1987).

Finlayson, S.A., et al., "Acetyl–Coenzyme A Carboxylase from the Developing Endosperm of *Ricinus communis*", *Archives of Biochemistry and Biophysics*, 225, 576–585 (1983).

Gengenbach, B., et al., "Maize Acetyl–Coenzyme A Carboxylase Genes", In: *Plant Lipid Metabolism*, Kader, J.–C., et al., (eds.), Kluwer Academic Press, the Netherlands, p. 43–45 (1995).

Gornicki, P., et al., "Genes for Two Subunits of Acetyl Coenzyme A Carboxylase of *Anabaena* sp. Strain PCC 7120: Biotin Carboxylase and Biotin Carboxyl Carrier Protein", *Journal of Bacteriology*, 175, 5268–5272 (Aug. 1993).

Gornicki, P., et al., "Wheat Acetyl–CoA Carboxylase", *Plant Molecular Biology*, 22, 547–522 (1993).

Gornicki, P., et al., "Wheat Acetyl–Coenzyme A Carboxylase: cDNA and Protein Structure", *Proc. Natl. Acad. Sci. USA*, 91, 6860–6864 (Jul. 1994).

Green, C.E., et al., "Plant Regeneration in Tissue Cultures of Maize", In: *Maize for Biological Research*, Sheridan, W.F., (ed.), Plant Mol. Biol. Assoc., Charlottesville, VA, pp. 367–372 (1982).

Kannangra, C.G., et al., "Fat Metabolism in Higher Plants— LIV. A Procaryotic Type Acetyl CoA Carboxylase in Spinach Chloroplasts", *Archives of Biochemistry and Biophysics*, 152, 83–91 (1972).

Klein, T.M., et al., "High–Velocity Microprojectiles for Delivering Nucleic Acids into Living Cells", *Nature*, 327, 70–73 (1987).

Kondo, H., et al., "Acetyl–CoA Carboxylase from *Escherichia coli*: Gene Organization and Nucleotide Sequence of the Biotin Carboxylase Subunit", *Proc. Natl. Acad. Sci. USA*, 88, 9730–9733 (Nov. 1991).

Koziel, M.G., et al., "Optimizing Expression of Transgenes with an Emphasis on Post–Transcriptional Events", *Plant Molecular Biology*, 32, 398–405 (1996).

Laing, W.A., et al., "Activation of Spinach Chloroplast Acetyl–Coenzyme A Carboxylase by Coenzyme A", *FEBS Letters*, 144, 341–344 (Aug. 1982).

Lamhonwah, A.-M., et al., "Sequence Homology around the Biotin–Binding Site of Human Propionyl–CoA Carboxylase and Pyruvate Carboxylase", *Archives of Biochemistry and Biophysics,* 254, 631–636 (May 1, 1987).

Li, S.-J., et al., "The Gene Encoding the Biotin Carboxylase Subunit of *Escherichia coli* Acetyl–CoA Carboxylase", *Journal of Biological Chemistry,* 267, 855–863 (Jan. 15, 1992).

Li, S.-J., et al., "The Genes Encoding the Two Carboxyltransferase Subunits of *Escherichia coli* Acetyl–CoA Carboxylase", *Journal of Biological Chemistry,* 267, 16841–16847 (Aug. 25, 1992).

López–Casillas, F., et al., "Structure of the Coding Sequence and Primary Amino Acid Sequence of Acetyl–Coenzyme A Carboxylase", *Proc. Natl. Acad. Sci. USA,* 85, 5784–5788 (Aug. 1988).

Lutz, S., et al., "Characterization of Two Acetyl–CoA Carboxylase Genes from Maize", *Abstracts, International Congress of Plant Molecular Biology,* Amsterdam, The Netherlands (Jun. 1994).

Lutz, S., et al., "Intron Sequence Divergence in Type A and B Maize ACCase Genes", *Abstracts, 37th Annual Maize Genetics Conference,* Pacific Grove, CA, Poster No. 34, p. 38 (Mar. 16–19, 1995).

Marshall, L., et al., "Chromosome Number and Fatty Acid Levels in Sethoxydim–Tolerant Corn Cell Lines", *Agronomy Abstracts,* 170 (1988).

Marshall, L.C., et al., "Allelic Mutations in Acetyl–Coenzyme A Carboxylase Confer Herbicide Tolerance in Maize", *Theor. Appl. Genet.,* 83, 435–442 (1992).

McCabe, D.E., et al., "Stable Transformation of Soybean (*Glycine max*) by Particle Acceleration", *Bio/Technology,* 6, 923–926 (Aug. 1988).

Meredith, C.P., et al., "Herbicide Resistance in Plant Cell Cultures", In: *Herbicide Resistance in Plants,* LeBaron, H.M., et al., (eds.), John Wiley and Sons, New York, p. 275–291 (1982).

Metzler, D.E., In: *Biochemistry—The Chemical Reactions of Living Cells,* Academic Press, New York, p. 303 (1977).

Nikolau, B.J., et al., "Purification and Characterization of Maize Leaf Acetyl–Coenzyme A Carboxylase", *Archives of Biochemistry and Biophysics,* 288, 86–96 (Jan. 1984).

Parker, W.B., et al., "Dominant Mutations Causing Alterations in Acetyl–Coenzyme A Carboxylase Confer Tolerance to Cyclohexanedione and Aryloxyphenoxypropionate Herbicides in Maize", *Proc. Natl. Acad. Sci. USA,* 87, 7175–7179 (Sep. 1990).

Parker, W.B., et al., "Selection and Characterization of Corn Cell Lines Tolerant to Sethoxydim", Abstract No. 180, p. 64 (Feb. 3, 1988).

Parker, W.B., et al., "Selection and Characterization of Corn Cell Lines Tolerant to Sethoxydim", *Proceedings of the North Central Weed Control Conference,* 42, Kansas City, MO, p. 56 (Dec. 8–10, 1987).

Parker, W.B., et al., "Selection and Characterization of Sethoxyim Tolerant Corn Cell Lines", Third University of Minnesota Research Poster Session: Basic and Applied Bio–Medical Research in Academia and Industry (May 25, 1988).

Parker, W.B., et al., "Selection for Tolerance to Sethoxydim in Corn Tissue Culture", *Proceedings of the North Central Weed Control Conference,* 41, Milwaukee, WI, p. 93 (Dec. 2–4, 1986).

Phillips, R.L., et al., "Cell/Tissue Culture and In Vitro Manipulation", In: *Corn and Corn Improvement,* Sprague, G.F., et al., (eds.), American Society of Agronomy, Madison, WI, p. 345–387 (1988).

Post–Beittenmiller, D., et al., "Regulation of Plant Fatty Acid Biosynthesis", *Plant PHysiology,* 100, 923–930 (1992).

Rhodes, C.A., et al., "Genetically Transformed Maize Plants from Protoplasts", *Science,* 240, 204–207 (Apr. 1988).

Roesler, K.R., et al., "Structure and Expression of an Arabidopsis Acetyl–Coenzyme A Carboxylase Gene", *Plant Physiology,* 105, 611–617 (Jun. 1994).

Roessler, P.G., "Purification and Characterization of Acetyl–CoA Carboxylase from the Diatom *Cyclotella cryptica*", *Plant Physiology,* 92, 73–78 (1990).

Roessler, P.G., et al., "Cloning and Characterization of the Gene that Encodes Acetyl–Coenzyme A Carboxylase in the Alga *Cyclotella cryptica*", *Journal of Biological Chemistry,* 268, 19254–19259 (Sep. 15, 1993).

Sasaki, Y., et al., "Chloroplast–Encoded Protein as a Subunit of Acetyl–CoA Carboxylase in Pea Plant", *Journal of Biological Chemistry,* 268, 25118–25123 (Nov. 25, 1993).

Schulte, W., et al., "A Gene Encoding Acetyl–Coenzyme A Carboxylase from *Brassica napus*", *Plant Physiology,* 106, 793–794 (1994).

Shorrosh, B.S., et al., "Molecular Cloning, Characterization, and Elicitation of Acetyl–CoA Carboxylase from Alfalfa", *Proc. Natl. Acad. Sci. USA,* 91, 4323–4327 (May 1994).

Slabas, A.R., et al., "Rapid Purification of a High Molecular Weight Subunit Polypeptide Form of Rape Seed Acetyl CoA Carboxylase", *Plant Science,* 39, 177–182 (1985).

Smith, C.J.S., et al., "Antisense RNA Inhibition of Polygalacturonase Gene Expression in Transgenic Tomatoes", *Nature,* 334, 724–726 (Aug. 25, 1988).

Somers, D.A., et al., "Expression of the *Acc1* Gene–Encoded Acetyl–Coenzyme A Carboxylase in Developing Maize (*Zea mays* L.) Kernels", *Plant Physiology,* 101, 1097–1101 (1993).

Stam, M., et al., "The Silence of Genes in Transgenic Plants", *Annals of Botany,* 79, 3–12 (1997).

Takai, T., et al., "Primary Structure of Chicken Liver Acetyl–CoA Carboxylase Deduced from cDNA Sequence", *Journal of Biological Chemistry,* 263, 2651–2657 (1988).

Turnham, E., et al., "Changes in the Activity of Acetyl–CoA Carboxylase During Rape–Seed Formation", *Biochem. J.,* 212, 223–229 (1983).

Vahlensieck, H.F., et al., "Identification of the Yeast *ACC1* Gene Product (Acetyl–CoA Carboxylase) as the Target of the Polyketide Fungicide Soraphen A", *Current Genetics,* 25, 95–100 (1994).

Van Dee, K.L., "Evidence for Two Independently Segregating Loci Encoding Acetyl–CoA Carboxylase in *Zea mays*", Master of Science Thesis, University of Minnesota, 75 p. (Jan. 1994).

Van Dee, K.L., et al., "RFLP Mapping of *Acc1* in *Zea mays* L.", *Agronomy Abstracts,* p. 198 (1992).

Vasil, I.K., "Progress in the Regeneration and Genetic Manipulation of Cereal Crops", *Bio/Technology,* 6, 398–402 (Apr. 1988).

Von Heijne, G., et al., "Domain Structure of Mitochondrial and Chloroplast Targeting Peptides", *Eur. J. Biochem.,* 180, 535–545 (1989).

Yamada, Y., "Tissue Culture Studies on Cereals", *In*: *Plant Cell, Tissue and Organ Culture,* Springer–Verlag, Berlin, 144–159 (1977).

\* cited by examiner

```
AGA GAT GAA GCT CGC ATG CCA ATG CGC CAC ACA TTC CTC TGG TTG GAT
GAC AAG AGT TGT TAT GAA GAA GAG CAG ATT CTC CGG CAT GTG GAG CCT
CCC CTC TCT ACA CTT CTT GAA TTG GAT AAG TTG AAG GTG AAA GGA TAC
AAT GAA ATG AAG TAT ACT CCT TCG CGT GAC CGC CAA TGG CAT ATC TAC
ACA CTA AGA AAT ACT GAA AAC CCC AAA ATG TTG CAT AGG GTG TTT TTC
CGA ACT ATT GTC AGG CAA CCC AAT GCA GGC AAC AAG TTT AGA TCG CTT
CAG ATC AGC GAC GCN AAG GTA GGA TGT CCC GAA GAA TCT CTT TCA TTT
ACA TCA AAT AGC ATC TTA AGA TCA TTG ATG ACT GCT ATT GAA GAA TTA
GAG CTT CAT GCA ATT AGG ACA GGT CAT TCT CAC ATG TAT TTG TGC ATA
CTG AAA GAG CAA AAG CTT CTT GAC CTC ATT CCA TTT TCA GGG AGT ACA
ATT GTT GAT GTT GGC CAA GAT GAA GCT ACC GCT TGT TCA CTT TTA AAA
TCA ATG GCT TTG AAG ATA CAT GAG CTT GTT GGT GCA AGG ATG CAT CAT
CTG TCT GTA TGC CAG TGG GAG GTG AAA CTC AAG TTG GAC TGT GAT GGC
CCT GCA AGT GGT ACC TGG AGA GTT GTA ACT ACA AAT GTT ACT GGT CAC
ACC TGC ACC ATT GAT ATA TAC CGA GAA GTG GAG GAA ATA GAA TCA CAG
AAG TTA GTG TAC CAT TCA GCC AGT TCG TCA GCT GGA CCA TTG CAT GGT
GTT GCA CTG AAT AAT CCA TAT CAA CCT TTG AGT GTG ATT GAT CTA AAG
CGC TGC TCT GCT AGG AAC AAC AGA ACA ACA TAT GCT TAT GAT TTT CCG
CTG GCC TTT GAA ACT GCA CTG CAG AAG TCA TGG CAG TCC AAT GGC TCT
ACT GTT TCT GAA GGC AAT GAA AAT AGT AAA TCC TAC GTG AAG GCA ACT
GAG CTA GTG TTT GCT GAA AAA CAT GGG TCC TGG GGC ACT CCT ATA ATT
CCG ATG GAA CGC CCT GCT GGG CTC AAC GAC ATT GGT ATG GTC GCT TGG
ATC ATG GAG ATG TCA ACA CCT GAA TTT CCC AAT GGC AGG CAG ATT ATT
GTT GTA GCA AAT GAT ATC ACT TTC AGA CTG GGA TCA TTT GGC CCA AGG
GAA GAT GCA TTT TTT GAA ACT GTC ACT AAC CTG GCT TGC GAA AGG AAA
CTT CCT CTT ATA TAC TTG GCA GCA AAC TCT GGT GCT AGG ATT GGC ATA
GCT GAT GAA GTA AAA TCT TGC TTC CGT GTT GGA TGG TCT GAC GAA GGC
AGT CCT GAA CGA GGG TTT CAG TAC ATC TAT CTG ACT GAA GAA GAC TAT
GCT CGC ATT AGC TCT TCT GTT ATA GCA CAT AAG CTG GAG CTA GAT AGT
GGT GAA ATT AGG TGG ATT ATT GAC TCT GTT GTG GGC AAG GAG GAT GGG
CTT GGT GTC GAG AAC ATA CAT GGA AGT GCT GCT ATT GCC AGT GCT TAT
TCT AGG GCA TAT GAG GAG ACA TTT ACA CTT ACA TTT GTG ACT GGG CGG
ACT GTA GGA ATA GGA GCT TAT CTT GCT CGA CTT GGT ATA CGG TGC ATA
CAG CGT CTT GAC CAG CCT ATT ATT TTA ACA GGG TTT TCT GCC CTG AAC
AAG CTC CTT GGG CGG GAA GTG TAC AGC TCC CAC ATG CAG CTT GGT GGT
CCT AAG ATC ATG GCG ACC AAT GGT GTT GTC CAC CTC ACT GTT CCA GAT
```

FIG. 10A

```
GTC CTT GAA GGT GTT TCC AAT ATA TTG AGG TGG CTC AGC TAT GTT CCT
GCA AAC ATT GGT GGA CCT CTT CCT ATT ACC AAA CCT CTG GAC CCT CCA
GAC AGA CCT GTT GCT TAC ATC CCT GAG AAC ACA TGC GAT CCA CGT GCA
GCT ATC TGT GGT GTA GAT GAC AGC CAA GGG AAA TGG TTG GGT GGT ATG
TTT GAC AAA GAC AGC TTT GTG GAG ACA TTT GAA GGA TGG GCA AAA ACA
GTG GTT ACT GGC AGA GCA AAG CTT GGA GGA ATT
```

FIG. 10B

```
   1  GGTCTTCAAT TGTGCTGTCT GGGCCACGGA ACGACAATGT CACAGCTTGG
  51  ATTAGCCGCA GCTGCCTCAA AGGCCTTGCC ACTACTCCCT AATCGCCAGA
 101  GAAGTTCAGC TGGGACTACA TTCTCATCAT CTTCATTATC GAGGCCCTTA
 151  AACAGAAGGA AAAGCCATAC TCGTTCACTC CGTGATGGCG GAGATGGGGT
 201  ATCAGATGCC AAAAAGCACA GCCAGTCTGT TCGTCAAGGT CTTGCTGGCA
 251  TTATCGACCT CCCAAGTGAG GCACCTTCCG AAGTGGATAT TTCACATGGA
 301  TCTGAGGATC CTAGGGGCC AACAGATTCT TATCAAATGA ATGGGATTAT
 351  CAATGAAACA CATAATGGAA GACATGCCTC AGTGTCCAAG GTTGTTGAAT
 401  TTTGTGCGGC ACTAGGTGGC AAAACACCAA TTCACAGTAT ATTAGTGGCC
 451  AACAATGGAA TGGCAGCAGC AAAATTTATG AGGAGTGTCC GGACATGGGC
 501  TAATGATACT TTTGGATCTG AGAAGGCAAT TCAACTCATA GCTATGGCAA
 551  CTCCGGAAGA CATGAGGATA AATGCAGAAC ACATTAGAAT TGCTGACCAA
 601  TTCGTAGAGG TGCCTGGTGG AACAAACAAT AATAACTACG CCAATGTTCA
 651  ACTCATAGTG GGGATGGCAC AAAAACTAGG TGTTTCTGCT GTTTGGCCTG
 701  GTTGGGGTCA TGCTTCTGAG AATCCTGAAC TGCCAGATGC ATTGACCGCA
 751  AAAGGGATCG TTTTCTTGG CCCACCTGCA TCATCAATGA ATGCTTTGGG
 801  AGATAAGGTC GGCTCAGCTC TCATTGCTCA AGCAGCCGGG GTCCCAACTC
 851  TTGCTTGGAG TGGATCACAT GTTGAAGTTC CATTAGAGTG CTGCTTAGAC
 901  GCGATACCTG AGGAGATGTA TAGAAAAGCT TGCGTTACTA CCACAGAGGA
 951  AGCAGTTGCA AGTTGTCAAG TGGTTGGTTA TCCTGCCATG ATTAAGGCAT
1001  CCTGGGGAGG TGGTGGTAAA GGAATAAGAA AGGTTCATAA TGATGATGAG
1051  GTTAGAGCGC TGTTTAAGCA AGTACAAGGT GAAGTCCCTG GCTCCCCAAT
1101  ATTTGTCATG AGGCTTGCAT CCCAGAGTCG GCATCTTGAA GTTCAGTTGC
1151  TTTGTGATCA ATATGGTAAT GTAGCAGCAC TTCACAGTCG TGATTGCAGT
1201  GTGCAACGGC GACACCAGAA GATTATTGAA GAAGGTCCAG TTACTGTTGC
1251  TCCTCGTGAG ACAGTTAAAG CACTTGAGCA GGCAGCAAGG AGGCTTGCTA
1301  AGGCTGTGGG TTATGTTGGT GCTGCTACTG TTGAGTATCT TTACAGCATG
1351  GAAACTGGAG ACTACTATTT TCTGGAACTT AATCCCCGAC TACAGGTTGA
1401  GCATCCAGTC ACTGAGTGGA TAGCTGAAGT GAATCTGCCT GCAGCTCAAG
1451  TTGCTGTTGG AATGGGCATA CCTCTTTGGC AGATTCCAGA AATCAGACGT
1501  TTCTATGGAA TGGACTATGG AGGAGGGTAT GACATTTGGA GGAAAACAGC
1551  AGCTCTTGCT ACACCATTTA ATTTTGATGA AGTAGATTCT CAATGGCCAA
1601  AGGGCCATTG TGTAGCAGTT AGAATTACTA GTGAGGACCC AGATGATGGT
1651  TTCAAACCTA CTGGTGGGAA AGTGAAGGAG ATAAGTTTTA AAAGCAAGCC
1701  TAATGTTTGG GCCTACTTCT CAGTAAAGTC TGGTGGAGGC ATTCATGAAT
1751  TTGCTGATTC TCAGTTTGGA CATGCTTTTG CATATGGACT CTCTAGACCA
```

FIG. 13A

```
1801  GCAGCTATAA CAAACATGTC TCTTGCATTA AAAGAGATTC AGATTCGTGG
1851  AGAAATTCAT TCAAATGTTG ATTACACAGT TGACCTCTTA AACGCTTCAG
1901  ACTTCAGAGA AAACAAGATC CACACTGGTT GGCTGGATAC AAGAATAGCT
1951  ATGCGTGTTC AAGCTGAGAG GCCCCCATGG TATATCTCAG TGGTTGGAGG
2001  TGCTTTATAT AAAACAGTAA CCACCAATGC AGCCACTGTT TCTGAATATG
2051  TTAGTTATCT CACCAAGGGC CATATTCCAC CAAAGCATAT ATCCCTTGTC
2101  AATTCTACAG TTAATTTGAA TATAGAAGGG AGCAAATACA CAATTGAAAC
2151  TGTAAGGACT GGACATGGTA GCTACAGGTT GAGAATGAAT GATTCAACAG
2201  TTGAAGCGAA TGTACAATCT TTATGTGATG GTGGCCTCTT AATGCAGTTG
2251  GATGGAAACA GCCATGTAAT TTATGCAGAA GAAGAAGCTG GTGGTACACG
2301  GCTTCAGATT GATGGAAAGA CATGTTTATT GCAGAATGAC CATGATCCAT
2351  CGAAGTTATT AGCTGAGACA CCCTGCAAAC TTCTTCGTTT CTTGGTTGCT
2401  GATGGTGCTC ATGTTGATGC GGATGTACCA TACGCGGAAG TTGAGGTTAT
2451  GAAGATGTGC ATGCCTCTCT TGTCACCTGC TTCTGGTGTC ATTCATTGTA
2501  TGATGTCTGA GGGCCAGGCA TTGCAGGCTG GTGATCTTAT AGCAAGGTTG
2551  GATCTTGATG ACCCTTCTGC TGTGAAAAGA GCTGAGCCAT TTGATGGAAT
2601  ATTTCCACAA ATGGAGCTCC CTGTTGCTGT CTCTAGTCAA GTACACAAAA
2651  GATATGCTGC AAGTTTGAAT GCTGCTCGAA TGGTCCTTGC AGGATATGAG
2701  CACAATATTA ATGAAGTCGT TCAAGATTTG GTATGCTGCC TGGACAACCC
2751  TGAGCTTCCT TTCCTACAGT GGGATGAACT TATGTCTGTT CTAGCAACGA
2801  GGCTTCCAAG AAATCTCAAG AGTGAGTTAG AGGATAAATA CAAGGAATAC
2851  AAGTTGAATT TTTACCATGG AAAAAACGAG GACTTTCCAT CCAAGTTGCT
2901  AAGAGACATC ATTGAGGAAA ATCTTTCTTA TGGTTCAGAG AAGGAAAAGG
2951  CTACAAATGA GAGGCTTGTT GAGCCTCTTA TGAACCTACT GAAGTCATAT
3001  GAGGGTGGGA GAGAGAGCCA TGCACATTTT GTTGTCAAGT CTCTTTTCGA
3051  GGAGTATCTT ACAGTGGAAG AACTTTTTAG TGATGGCATT CAGTCTGACG
3101  TGATTGAAAC ATTGCGGCAT CAGCACAGTA AAGACCTGCA GAAGGTTGTA
3151  GACATTGTGT TGTCTCACCA GGGTGTGAGG AACAAAGCTA AGCTTGTAAC
3201  GGCACTTATG GAAAAGCTGG TTTATCCAAA TCCTGGTGGT TACAGGGATC
3251  TGTTAGTTCG CTTTTCTTCC CTCAATCATA AAGATATTA TAAGTTGGCC
3301  CTTAAAGCAA GTGAACTTCT TGAACAAACC AAACTAAGTG AACTCCGTGC
3351  AAGCGTTGCA AGAAGCCTTT CGGATCTGGG GATGCATAAG GGAGAAATGA
3401  GTATTAAGGA TAACATGGAA GATTTAGTCT CTGCCCCATT ACCTGTTGAA
3451  GATGCTCTGA TTTCTTTGTT TGATTACAGT GATCGAACTG TTCAGCAGAA
3501  AGTGATTGAG ACATACATAT CACGATTGTA CCAGCCTCAT CTTGTAAAGG
3551  ATAGCATCCA AATGAAATTC AAGGAATCTG GTGCTATTAC TTTTTGGGAA
```

FIG. 13B

```
3601  TTTTATGAAG GGCATGTTGA TACTAGAAAT GGACATGGGG CTATTATTGG
3651  TGGGAAGCGA TGGGGTGCCA TGGTCGTTCT CAAATCACTT GAATCTGCGT
3701  CAACAGCCAT TGTGGCTGCA TTAAAGGATT CGGCACAGTT CAACAGCTCT
3751  GAGGGCAACA TGATGCACAT TGCATTATTG AGTGCTGAAA ATGAAAGTAA
3801  TATAAGTGGA ATAAGCAGTG ATGATCAAGC TCAACATAAG ATGGAAAAGC
3851  TTAGCAAGAT ACTGAAGGAT ACTAGCGTTG CAAGTGATCT CCAAGCTGCT
3901  GGTTTGAAGG TTATAAGTTG CATTGTTCAA AGAGATGAAG CTCGCATGCC
3951  AATGCGCCAC ACATTCCTCT GGTTGGATGA CAAGAGTTGT TATGAAGAAG
4001  AGCAGATTCT CCGGCATGTG GAGCCTCCCC TCTCTACACT TCTTGAATTG
4051  GATAAGTTGA AGGTGAAAGG ATACAATGAA ATGAAGTATA CTCCTTCGCG
4101  TGACCGCCAA TGGCATATCT ACACACTAAG AAATACTGAA AACCCCAAAA
4151  TGTTGCATAG GGTGTTTTC CGAACTATTG TCAGGCAACC CAATGCAGGC
4201  AACAAGTTTA GATCGGCTCA GATCAGCGAC GCTGAGGTAG GATGTCCCGA
4251  AGAATCTCTT TCATTTACAT CAAATAGCAT CTTAAGATCA TTGATGACTG
4301  CTATTGAAGA ATTAGAGCTT CATGCAATTA GGACAGGTCA TTCTCACATG
4351  TATTTGTGCA TACTGAAAGA GCAAAAGCTT CTTGACCTCA TTCCATTTTC
4401  AGGGAGTACA ATTGTTGATG TTGGCCAAGA TGAAGCTACC GCTTGTTCAC
4451  TTTTAAAATC AATGGCTTTG AAGATACATG AGCTTGTTGG TGCAAGGATG
4501  CATCATCTGT CTGTATGCCA GTGGGAGGTG AAACTCAAGT TGGACTGTGA
4551  TGGCCCTGCA AGTGGTACCT GGAGAGTTGT AACTACAAAT GTTACTGGTC
4601  ACACCTGCAC CATTGATATA TACCGAGAAG TGGAGGAAAT AGAATCACAG
4651  AAGTTAGTGT ACCATTCAGC CAGTTCGTCA GCTGGACCAT TGCATGGTGT
4701  TGCACTGAAT AATCCATATC AACCTTTGAG TGTGATTGAT CTAAAGCGCT
4751  GCTCTGCTAG GAACAACAGA ACAACATATT GCTATGATTT TCCGCTGGCC
4801  TTTGAAACTG CACTGCAGAA GTCATGGCAG TCCAATGGCT CTACTGTTTC
4851  TGAAGGCAAT GAAAATAGTA ATCCTACGT GAAGGCAACT GAGCTAGTGT
4901  TTGCTGAAAA ACATGGGTCC TGGGGCACTC CTATAATTCC GATGGAACGC
4951  CCTGCTGGGC TCAACGACAT TGGTATGGTC GCTTGGATCA TGGAGATGTC
5001  AACACCTGAA TTTCCCAATG GCAGGCAGAT TATTGTTGTA GCAAATGATA
5051  TCACTTTCAG AGCTGGATCA TTTGGCCCAA GGGAAGATGC ATTTTTTGAA
5101  ACTGTCACTA ACCTGGCTTG CGAAAGGAAA CTTCCTCTTA TATACTTGGC
5151  AGCAAACTCT GGTGCTAGGA TTGGCATAGC TGATGAAGTA AAATCTTGCT
5201  TCCGTGTTGG ATGGTCTGAC GAAGGCAGTC CTGAACGAGG GTTTCAGTAC
5251  ATCTATCTGA CTGAAGAAGA CTATGCTCGC ATTAGCTCTT CTGTTATAGC
5301  ACATAAGCTG GAGCTAGATA GTGGTGAAAT TAGGTGGATT ATTGACTCTG
5351  TTGTGGGCAA GGAGGATGGG CTTGGTGTCG AGAACATACA TGGAAGTGCT
```

FIG. 13C

```
5401  GCTATTGCCA GTGCTTATTC TAGGGCATAT GAGGAGACAT TTACACTTAC
5451  ATTTGTGACT GGGCGGACTG TAGGAATAGG AGCTTATCTT GCTCGACTTG
5501  GTATACGGTG CATACAGCGT CTTGACCAGC CTATTATTTT AACAGGGTTT
5551  TCTGCCCTGA ACAAGCTCCT TGGGCGGGAA GTGTACAGCT CCCACATGCA
5601  GCTTGGTGGT CCTAAGATCA TGGCGACCAA TGGTGTTGTC CACCTCACTG
5651  TTCCAGATGT CCTTGAAGGT GTTTCCAATA TATTGAGGTG GCTCAGCTAT
5701  GTTCCTGCAA ACATTGGTGG ACCTCTTCCT ATTACCAAAC CTCTGGACCC
5751  TCCAGACAGA CCTGTTGCTT ACATCCCTGA GAACACATGC GATCCACGTG
5801  CAGCTATCTG TGGTGTAGAT GACAGCCAAG GGAAATGGTT GGGTGGTATG
5851  TTTGACAAAG ACAGCTTTGT GGAGACATTT GAAGGATGGG CAAAAACAGT
5901  GGTTACTGGC AGAGCAAAGC TTGGAGGAAT TCCTGTGGGC GTCATAGCTG
5951  TGGAGACACA GACCATGATG CAGATCATCC CTGCTGATCC AGGTCAGCTT
6001  GATTCCCATG AGCGATCTGT CCCTCGTGCT GGACAAGTGT GGTTCCCAGA
6051  TTCTGCAACC AAGACCGCTC AGGCATTATT AGACTTCAAC CGTGAAGGAT
6101  TGCCTCTGTT CATCCTGGCT AATTGGAGAG GCTTCTCTGG TGGACAAAGA
6151  GATCTCTTTG AAGGAATTCT TCAGGCTGGG TCAACAATTG TCGAGAACCT
6201  TAGGACATAT AATCAGCCTG CTTTTGTGTA CATTCCTATG GCTGGAGAGC
6251  TTCGTGGAGG AGCTTGGGTT GTGGTCGATA GCAAAATAAA TCCAGACCGC
6301  ATTGAGTGTT ATGCTGAAAG GACTGCCAAA GGTAATGTTC TCGAACCTCA
6351  AGGGTTAATT GAAATCAAGT TCAGGTCAGA GGAACTCCAA GACTGTATGG
6401  GTAGGCTTGA CCCAGAGTTG ATAAATCTGA AAGCAAAACT CCAAGATGTA
6451  AATCATGGAA ATGGAAGTCT ACCAGACATA GAAGGGATTC GGAAGAGTAT
6501  AGAAGCACGT ACGAAACAGT TGCTGCCTTT ATATACCCAG ATTGCAATAC
6551  GGTTTGCTGA ATTGCATGAT ACTTCCCTAA GAATGGCAGC TAAAGGTGTG
6601  ATTAAGAAAG TTGTAGACTG GGAAGAATCA CGCTCGTTCT TCTATAAAAG
6651  GCTACGGAGG AGGATCGCAG AAGATGTTCT TGCAAAAGAA ATAAGGCAGA
6701  TAGTCGGTGA TAAATTTACG CACCAATTAG CAATGGAGCT CATCAAGGAA
6751  TGGTACCTTG CTTCTCAGGC CACAACAGGA AGCACTGGAT GGGATGACGA
6801  TGATGCTTTT GTTGCCTGGA AGGACAGTCC TGAAAACTAC AAGGGGCATA
6851  TCCAAAAGCT TAGGGCTCAA AAAGTGTCTC ATTCGCTCTC TGATCTTGCT
6901  GACTCCAGTT CAGATCTGCA AGCATTCTCG CAGGGTCTTT CTACGCTATT
6951  AGATAAGATG GATCCCTCTC AGAGAGCGAA GTTTGTTCAG GAAGTCAAGA
7001  AGGTCCTTGA TTGATGATAC CAACACATCC AACACAATGT GTGCATGTCA
7051  CATCTTTTTG TTCTAGTACA TACATAGAAG GATATTGCTT GGTCTTGATT
7101  GATCATGTCT GATTTAAGTC GACTATTATT TCTTGGAATT TTCTTTTGGA
7151  CCTGGTGCTA TGGTTGATGG ATGTATATTG GATATGTGCG TTCTGCCAGG
```

FIG. 13D

```
7201  TGTAAGCACA  AAGGTTTAGA  CARAMMRARA  RCAAGAGCGA  GTGAACCTGT
7251  TCTGGTTTTG  CAGTGGTTCA  GTAAGGCAGA  AAGTTGTTAA  ACCGTAGTTC
7301  TGAGATGTAT  TACCAGTGNC  GCCATGCTGT  ACTTTTAGGG  TGTATAATGC
7351  GGATACAAAT  AAACAATTTA  GCGGTTCATT  AAAGTTTGAA  CTCAAATAAC
7401  ATGTTCTTTG  TAAGCATATG  TACCGTACCT  CTACGTGAAA  TAAAGTTGTT
7451  GAATTAGCAT  TCGAAAAAAA
```

FIG. 13E

```
   1  MSQLGLAAAA  SKALPLLPNR  QRSSAGTTFS  SSSLSRPLNR  RKSHTRSLRD
  51  GGDGVSDAKK  HSQSVRQGLA  GIIDLPSEAP  SEVDISHGSE  DPRGPTDSYQ
 101  MNGIINETHN  GRHASVSKVV  EFCAALGGKT  PIHSILVANN  GMAAAKFMRS
 151  VRTWANDTFG  SEKAIQLIAM  ATPEDMRINA  EHIRIADQFV  EVPGGTNNNN
 201  YANVQLIVGM  AQKLGVSAVW  PGWGHASENP  ELPDALTAKG  IVFLGPPASS
 251  MNALGDKVGS  ALIAQAAGVP  TLAWSGSHVE  VPLECCLDAI  PEEMYRKACV
 301  TTTEEAVASC  QVVGYPAMIK  ASWGGGGKGI  RKVHNDDEVR  ALFKQVQGEV
 351  PGSPIFVMRL  ASQSRHLEVQ  LLCDQYGNVA  ALHSRDCSVQ  RRHQKIIEEG
 401  PVTVAPRETV  KALEQAARRL  AKAVGYVGAA  TVEYLYSMET  GDYYFLELNP
 451  RLQVEHPVTE  WIAEVNLPAA  QVAVGMGIPL  WQIPEIRRFY  GMDYGGGYDI
 501  WRKTAALATP  FNFDEVDSQW  PKGHCVAVRI  TSEDPDDGFK  PTGGKVKEIS
 551  FKSKPNVWAY  FSVKSGGGIH  EFADSQFGHA  FAYGLSRPAA  ITNMSLALKE
 601  IQIRGEIHSN  VDYTVDLLNA  SDFRENKIHT  GWLDTRIAMR  VQAERPPWYI
 651  SVVGGALYKT  VTTNAATVSE  YVSYLTKGHI  PPKHISLVNS  TVNLNIEGSK
 701  YTIETVRTGH  GSYRLRMNDS  TVEANVQSLC  DGGLLMQLDG  NSHVIYAEEE
 751  AGGTRLQIDG  KTCLLQNDHD  PSKLLAETPC  KLLRFLVADG  AHVDADVPYA
 801  EVEVMKMCMP  LLSPASGVIH  CMMSEGQALQ  AGDLIARLDL  DDPSAVKRAE
 851  PFDGIFPQME  LPVAVSSQVH  KRYAASLNAA  RMVLAGYEHN  INEVVQDLVC
 901  CLDNPELPFL  QWDELMSVLA  TRLPRNLKSE  LEDKYKEYKL  NFYHGKNEDF
 951  PSKLLRDIIE  ENLSYGSEKE  KATNERLVEP  LMNLLKSYEG  GRESHAHFVV
1001  KSLFEEYLTV  EELFSDGIQS  DVIETLRHQH  SKDLQKVVDI  VLSHQGVRNK
1051  AKLVTALMEK  LVYPNPGGYR  DLLVRFSSLN  HKRYYKLALK  ASELLEQTKL
1101  SELRASVARS  LSDLGMHKGE  MSIKDNMEDL  VSAPLPVEDA  LISLFDYSDR
1151  TVQQKVIETY  ISRLYQPHLV  KDSIQMKFKE  SGAITFWEFY  EGHVDTRNGH
1201  GAIIGGKRWG  AMVVLKSLES  ASTAIVAALK  DSAQFNSSEG  NMMHIALLSA
1251  ENESNISGIS  SDDQAQHKME  KLSKILKDTS  VASDLQAAGL  KVISCIVQRD
1301  EARMPMRHTF  LWLDDKSCYE  EEQILRHVEP  PLSTLLELDK  LKVKGYNEMK
1351  YTPSRDRQWH  IYTLRNTENP  KMLHRVFFRT  IVRQPNAGNK  FRSAQISDAE
1401  VGCPEESLSF  TSNSILRSLM  TAIEELELHA  IRTGHSHMYL  CILKEQKLLD
1451  LIPFSGSTIV  DVGQDEATAC  SLLKSMALKI  HELVGARMHH  LSVCQWEVKL
1501  KLDCDGPASG  TWRVVTTNVT  GHTCTIDIYR  EVEEIESQKL  VYHSASSSAG
1551  PLHGVALNNP  YQPLSVIDLK  RCSARNNRTT  YCYDFPLAFE  TALQKSWQSN
1601  GSTVSEGNEN  SKSYVKATEL  VFAEKHGSWG  TPIIPMERPA  GLNDIGMVAW
1651  IMEMSTPEFP  NGRQIIVVAN  DITFRAGSFG  PREDAFFETV  TNLACERKLP
1701  LIYLAANSGA  RIGIADEVKS  CFRVGWSDEG  SPERGFQYIY  LTEEDYARIS
1751  SSVIAHKLEL  DSGEIRWIID  SVVGKEDGLG  VENIHGSAAI  ASAYSRAYEE
```

FIG. 14A

```
1801  TFTLTFVTGR  TVGIGAYLAR  LGIRCIQRLD  QPIILTGFSA  LNKLLGREVY
1851  SSHMQLGGPK  IMATNGVVHL  TVPDVLEGVS  NILRWLSYVP  ANIGGPLPIT
1901  KPLDPPDRPV  AYIPENTCDP  RAAICGVDDS  QGKWLGGMFD  KDSFVETFEG
1951  WAKTVVTGRA  KLGGIPVGVI  AVETQTMMQI  IPADPGQLDS  HERSVPRAGQ
2001  VWFPDSATKT  AQALLDFNRE  GLPLFILANW  RGFSGGQRDL  FEGILQAGST
2051  IVENLRTYNQ  PAFVYIPMAG  ELRGGAWVVV  DSKINPDRIE  CYAERTAKGN
2101  VLEPQGLIEI  KFRSEELQDC  MGRLDPELIN  LKAKLQDVNH  GNGSLPDIEG
2151  IRKSIEARTK  QLLPLYTQIA  IRFAELHDTS  LRMAAKGVIK  KVVDWEESRS
2201  FFYKRLRRRI  AEDVLAKEIR  QIVGDKFTHQ  LAMELIKEWY  LASQATTGST
2251  GWDDDDAFVA  WKDSPENYKG  HIQKLRAQKV  SHSLSDLADS  SSDLQAFSQG
2301  LSTLLDKMDP  SQRAKFVQEV  KKVLD
```

FIG. 14B

```
   1  AAGCTTGGTA TGGATTCgTC AGCGCCAAgC CGGGGTTTTG CATGCGCCCg
  51  ACTGGaArCs GAATTCCgTg AgCCCtGTaC rrCaATGGCA ACCCCAsGGT
 101  TACTggGGTG GCTGAATGGT CTCsGCTTAC GCAATTGTTT GTGGCAgCwG
 151  CGTGGGCTAA ATGTArGTTG TCTCTTGTTG CACTGCArGA TGGATGGGTA
 201  gCCTCTGGGC CGCCTCTGCT ArTGTCTArC GtTTGCTGAC TGTGGTTTAt
 251  TCAgGGATGC CCATGCCCAT GCTAgATTGA tAGGTGCCAT TCTAATGGTA
 301  GGTGGCGGTA AGGTTTATTA AGCTGyAGyA TCAGTAGGTA ACCTCATGAA
 351  TCAGGGTTTA aGCACACCTT TTCCTTTGTG TGGGTGCATA AGGAATGCAC
 401  TTGGCTTCGT TCCCTGATAG TCTTTGsTCA TGTGTCATTC TACCAAGTGG
 451  GTTACTGTAA CATTGCACTC TATGATGGTT GGTGGTtGTG CATCTTTyTG
 501  CTyCCCCTGG yTGTCTAATA CCTGCATGTa ACTGATGACC yyCyTTTATG
 551  TATCATATAG ATTACATCCT TTTGTTGTAC ATCTCAATTC TGAAAAAACA
 601  ATGTTTTGCA TTCTTAGCGc TCTGTGCaCA AgGaAAaGGa gGTTTTACCT
 651  gCAAcTtTTT TTTTCGAGAA AAAACAAACC TTTCTGAAaG gCAGTGATCA
 701  TTTAGtATAA AGAAATTTG ATTTACTTTC TTCAGAGAGA AtATkCCAAr
 751  CAAACAATTT TCTTACTGTC TGAGCCACGA AATTTGATCT TGATCtTACT
 801  TTCACAAGCC ACATGAAGCC tTATCATCGC TcTGATAAAA AArCCAAaTA
 851  GGTGATTCAT AGAATGAGar AAAGAACCTG TTGCCATTTG GGGaCCTTGT
 901  TGTGTACTCA TTATCCCCCC TGCTCAGGTT GAGGTTTCCT TGCCACTGCC
 951  ACCCCTTGGC CCCTTCTTAT ACAACCATCT CCATTGAAAa AGATTTTGCA
1001  CtACATTTGG GCTTcGTATG aCAAAAaAGG aAAATaAAaC TaAaCAGCAG
1051  AAACATAGTA TAaTTATAGg TAAAAGGTTc TGGCAAGTTT GAGTGGaAGA
1101  GACCTTTGTA TATTTGGACA TATTTCACTA GTAAATAGTT TTCTAAAATc
1151  TTCATGAATG GTGGCCAATA AACTTGATAA GATCTCAACA TGGCAGGTTC
1201  CTTCmAAATG AGAGGAAAAC TGGAAACATC ACAAATATTT TTTAGCGAGT
1251  GGCCTATAAA TTATAATGTT GCTTTCATTT CTTTGATATT CaAAACTTCC
1301  TAAGAGTATT CTGCTAGAGC TCTGATGGTG TCTTTTGCCT CTGTCAGATT
1351  TTCCAGGaGT TTTCTTCCCT TTTtATGGCA CTGTGCGTTT GAGAAGGTCT
1401  TCAATTGTGC TGTCTGGGCC ACGGAACGAC AATGTCACAG CTTGGATTAG
1451  CCGCAGCTGC CTCAAAGGCC TTGCCACTAC TCCCTAATCG CCAGAGAAGT
1501  TCAGCTGGGA CTACATTCTC ATCATCTTCA TTATCGAGGC CCTTAAACAG
1551  AAGGAAAAGC CATACTCGtT CACTCCGTGA TGGCGGAGAT GGgGTATCAG
1601  ATGCCAAAAA GCACAGCCAG TCTGTTCGTC AAGGTACTGt GAATATCTTT
1651  tGaTACAAgc tAAAATTTTG cTACAGAATA TaTAtTtaAA GAGTtCTtTC
1701  TTGGcTGGtG ttGtTTATTT GttT.aACAt sCGAAAgGGC CtctAgttGg
1751  attGgttaGG tggsCTGAAT ACCACTCCTT AAGGTCTTGA GTTTGCTTTT
```

FIG. 16A

```
1801  CCCCnCGGAG CGAATTTTAG GCTAGGGTTA CCCCCCCACC CCCACCCGAA
1851  TCTGCACAGy CCGGyCGyGG yCGyCCTCAT ATAGGCTACG ATGTCATTGT
1901  GTATCGGCGG GCCAGGGGTT TAAGAGTTTT CTTGACCTTT GTTAGAAGAT
1951  CTTAATAATA CAATGTCCAA GGGCTGTCTT ACCCTGTAGG TCGAGTTTTT
2001  AGTTGTTTTA ACATGGTAAT GTTTGAAGCC TCATTCTAGG TrCCAATATA
2051  GATATGCTCA CTGCTCAGTT TCAAATGTTT GTCTGCATGT AGGTCTTGCT
2101  GGCATTATCG ACCTCCCAAG TGAGGCACCT TCCGAAGTGG ATATTTCACA
2151  GTAAGGACTA CAATATTTG CGTACGTTTG TTTTGGAAAA AGAAAATATT
2201  CTCAGCTTAT TTATACTAGC TTCGCTAATA CTGAAATGCT GTCTTAATGT
2251  CCTGGTGCTG TATGCTCAAT CTTTCATAGT AAATGCTGCA AAATATGTGA
2301  TGTAACTGTT GCAACACAGC CAGGGACCTG TTATTTAGAG CATGGTGAAT
2351  GCTCTGGTTC AGTTATATGA TGTAGTTATA GCTCATGTTG AAGAATTAGT
2401  TGCAGTGTTT GCTGGACAAT GGTCACTTAT TATAAATCAT ATCTGCATAC
2451  ACATTTGTGA CTTCTGTTGC TGTAAATGCC CGCATTTTTT GAGAAAATT
2501  TAAATGCTTG GCCTAAATTG GACATATATG ATAGACAAAG CTGATTTGAA
2551  CTTTGTTTAT TTTGACATC CATGCATATT GTCAGTGTTG TGAAAACAAT
2601  ACTAATCCTT TTTTTTTGTC TTTTTCCAGT GGATCTGAGG ATCCTAGGGG
2651  GCCAACAGAT TCTTATCAAA TGAATGGGAT TATCAATGAA ACACATAATG
2701  GAAGACATGC CTCAGTGTCC AAGGTTGTTG AATTTGTGC GGCACTAGGT
2751  GGCAAAACAC CAATTCACAG TATATTAGTG GCCAACAATG GAATGGCAGC
2801  ACCCAAATTT ATGAGGAGTG TCCGGACATG GGCTAATGAT ACTTTGGAT
2851  CTGAGAAGGC AATTCAACTC ATAGCTATGG CAACTCCGGA AGACATGAGG
2901  ATAAATGCAG AACACATTAG AATTGCTGAC CAATTACGTA GAGGTGCCTG
2951  GTGGAACAAA CAATAATAAC TACGCCAATG TTCAACTCAT AGTGGAGGTT
3001  AGCCTTGCTA ATCTGTTAGT TTACTACTGG TCTGCTGTTT CCTTTATTTG
3051  TTGTATAATG ATTGACATAT TTAAGTAGAG AAATTTATAT TTCTCCTCTG
3101  CTGTTGTGGA AGTCCAATTG TCATCATTAA CTGTGAAATA TTGCAGATGG
3151  CACAAAAACT AGGTGTTTCT GCTGTTTGGC CTGGTTGGGG TCATGCTTCT
3201  GAGAATCCTG AACTGCCAGA TGCATTGACC GCAAAAGGGA TCGTTTTTCT
3251  TGGCCCACCT GsATCATCAA TGAATGCTTT GGGAGATAAG GTCGGCTCAG
3301  CTCTCATTGC TCAAGCAGCC GGGGnCCCAA CTCTTGCTTG GAGTGGATCA
3351  CATGTGAGTC TCACTCTTTG ATTACTATCC GCCTGTCTCA TTGCTCTCTC
3401  TTTCATATTC TAATGACACT AAATTTAGGT TGAAGTTCCA TTAGAGTGCT
3451  GCTTAGACGC GATACCTGAG GAGATGTATA GAAAAGCTT
```

FIG. 16B

```
   1 GAATTCCGTG AGCCCTGTAC GGCAATGGCA ACCCCAGGGT TACTGGGGTG
  51 GCTGAATGGT CTCGGCTTAC GCAATTGTTT GTGGCAGCTG CGTGGGCTAA
 101 ATGTAGGTTG TCTCTTGTTG CACTGCAGGA TGGATGGGTA GCCTCTGGGC
 151 CGCCTCTGCT AGTGTCTAGC GTTGCTGACT GTGGTTTATT CAGGGATGCC
 201 CATGCCCATG CTAGATTGAT AGGTCATAGG TGCCATTCTA ATGGTAGGTG
 251 GCGGTAAGGT TTATTAAGCT GTCGTATCAG TAGGTAACCT CATGAATCAG
 301 GGTTTAAGCC CACCTTCTCC TTTGTGGGG TGCATAAGGA ATGCACTTGG
 351 CTTCGTTCCC TGCTAGTCTT TGCTCATGTG TCATTCTACC AAGTGGGTTA
 401 CTGTAACATT GCACTCTATG ATGGTTGGTG GTTGTGCATC TTTTTGCTTC
 451 CCCTGGTTGT CTAATACCTG CATGTAACTG ATGACCTTCT TTTATGTATC
 501 ATATAGATTA CATCTTTTGT TGTACATCTC AATTCTGAAA AACAATGTTT
 551 TGCATTCTTA GCGCTCTGTG CACAAGGAAA AGGAGGTTTT ACCTGCAACT
 601 TTTTTTTTCG AGAAAAACA AACCTTTCTG AAAGGCAGTG ATCATTTAGT
 651 ATAAAGAAAA TTTGATTTAC TTTCTTCAGA GAGAATATTC CAAACAAACA
 701 ATTTTCTTAC AGTCTGAGCC ACGAAATTTG ATCTTGATCT TACTTTCACA
 751 AGCCACATGA AGCCTTATCA TCGCTCTGAT AAAAAAACCA AATAGGTGAT
 801 TCATAGAATG AGAAAAAGAA CCTGTTGCCA TTTGGGGACC TTGTTGTGTA
 851 CTCATTATCC CCCTGCTCA GGTTGAGGTT TCCTTGCCAC TGCCACCCCT
 901 TGGCCCCTTC TTATACAACC ATCTCCATTG AAAAAGATTT TGCACTACAT
 951 TTGGGCTTCG TATAACAAAA AAGGAAAATA AAACTAAACA GCAGAAACAT
1001 AGTATAATTA TAGGTAAAAG GTTNTGGCAA GTTTGAGTGG TAGAGACCTT
1051 TGTATATTTG GACATATTTC ACTAGTAAAT AGTTTTCTAA AATGTTCATG
1101 AATGGTGGCC AATAAACTTG ATAAGATCTC AACATGGCAG GTTCCTTCAA
1151 AATGAGAGGA AAACTGGAAA CATCACAAAT ATTTTTTAGC GAGTGGCCTA
1201 TAAATTATAA TGTTGCTTTC ATTTCTTTGA TATTCAAAAC TTCCTAAGAG
1251 TATTCTGCTA GAGCTCTGAT GGTGTCTTTT GCCTCTGTCA GATTTTCCAG
1301 GAGTTTTCTT CCCTTTTTAT GGCACTGT
```

FIG. 17

```
   1 AGCATCCCTT GGGATTGTGA TnACTCACAT AAATTCTTGC GAAnGTTGA
  51 CATTCTAGTG ATTTGAGTTC CGTTCTAGTG TGCTAGTCAn TTGAGCTCAA
 101 GTCTTGGTTT TATGTGTGCG TATTCACTGT GATCTTTGTG TCGTGTGTGA
 151 GTTGTTGATC CTTCCCTTGC TCCGTGATTC TTTGTGAAAT CTTTTGAAAG
 201 GGCGAGAGGC TCCAAGCTGT GGAGATTCCT CGCAAGTGGG ATTAAGAAAA
 251 GCAAAGCAAC ACCGTGGTAT TCAAGTTGGT CTTTGGACCG CTTGAGAGGG
 301 GTTGATTGCA ACCCTCGTCC GTTGGACGC CACAACGTGG AGTAGGCAAG
 351 CGTTGGTCTT GGCCGAACCA CGGGATAACC ACCGTGCCAT CTCTGTGATT
 401 GATATCTCTT GGTTATTGTG TTGTGTTGAG ATCCTTCTCT AGCCACTTGG
 451 CAAATTACTG TGCTAACAAT TAATCAAGTT TTGTGGCTTA AGATTTTGAA
 501 GTATTACAGG ATCTGCATCA TGGTCTGTGT CTCCACAGCT ATGACACCCA
 551 CAGGAATTCA TGTGTTCCTT GGAGCCACTC TTGGATGACC TAAAGGAATT
 601 ATTTCTAACC GGCTTGTACA CATATGATGC ATCAAGAGAT GAGTGTTTTA
 651 CTATGCGAGG GGCCATGCTT ATGACCATAA GTAATCTTCC TGGTTTAGAA
 701 ATGCTTGCTT CTCATATGGT TCATGGGAAA TTCGCATGCC TCCTTGTGGT
 751 GAAAATGTCT GGACAAAACA GCTGAAGAAT GGTCGTAAAT CTTGTTTTAT
 801 GGGAAATCGC CAATATATTG ATCTTGATCA TTCTTATTGC TTGGATGCAG
 851 ACTCCGTTTG ATGGAACGAT AGACTTCGAA CAAAACCTAA AACCTATTAT
 901 GATCGTCCAA TTTTGGATGA AATCATCACA CTTGGTGATT TCAAGAACTC
 951 AAAAAyTTAC AGTTAATTGG ATATAGGAGG GnGCAAAAAC ACAGTAAGTT
1001 GGACATTCCA TAAGGGGATT TATTTTAGTT GACAATAAAG TAGATGGGCA
1051 TCATCCTGAG TTTnGTTTGG CATCGTGTCG TAGATTGAAA CTGTAAGGAT
1101 GGACATGGTA GnTAACAGGT TGAGATGAAT GATTCAACAG TTGAAGCGAA
1151 TGTACAATCT TTATGTGATG GTGGCTnTTA ATGCAGGTAA CTAGTTTTTT
1201 TTTATGCTTT ATTATTAATT AGTTGGATAA ATGGTTTnGA TTTnTGATTG
1251 TTAAAnTGCA ATGGCTCCAG TTGGATGGnA ACAGCCAnGT AATTTATGCA
1301 GAAGnAGnAG nTGGTGGTAC ACGGnTTCAG ATTGATGGAA AGAnATGTTT
1351 ATTGCAGGTA AATAnTCCCT TnTTCCTTTA TATTTTTGTT GTnTGATTGT
1401 ATAAnTTTGn TAGATTATTT GTATAATTTA TTATTGCATT TCACCCCACT
1451 AAnTTATTTT TAAAAGATGG GTTTTGTTGT TGnTTCAGC nGGCGACATC
1501 ACATAAGnAA ATTGTGATTA ATTTTTGTTT TTTTGCAGnA TGACCATGAT
1551 CCATCAAAGT TATTA
```

FIG. 18A

```
   1  ACATAAGCTG GGTTAGTAGT GGTGAATTAG TGGATTATTG ATCTGTTGTG
  51  GGCAAGGAGn TGGCTTGGTG TCGAGAAAAA ACATGGAaGT GTGTATTGCC
 101  AGTGcTTaTT yTrGGGATAT GAGGGAATTw AmATTAcATT TGTGAcTGGG
 151  CGGACTGTAG GATAGGAGTT ATCTTGyTcG ATTGGTATAC GGTGCATACA
 201  GskyTTGACC AGCTATTATT TTAACAGGgT TTTCTGCCCT GAACAAGTCC
 251  TTGGGCGGGA AGTGTACAGc TCCCACATGC AGCTTGGTGG TCCTAAGATC
 301  ATGGCGACCA ATGGTGTTGT CCACCTCACT GTTCCAGATG ACCTTGAAGG
 351  TGTTTCCAAT ATATTGAGGT GGCTCAGCTA TGTTCCTGCA AACATTGGTG
 401  GACCTcTTCC TATTACCAAA CCTCTGGACC CTCCAGACAG ACCTGTTGCT
 451  TACATCCCTG AGAACACATG CGATCCACGT GCAGCTATCT GTGGTGTAGA
 501  TGACAGCCAA GGGAAATGGT TGGGTGGTAT GTTTGACAAA GACAGCTTTG
 551  TGGAGACATT TGAAGGATGG GCAAAACAG TGGTTACTGG CAGAGCAAAG
 601  CTTGGAGGAA TTCCATGCAT CTTAATAAAC ACAGTTGGCC CTTAAAGCAA
 651  GTGAACTTCT TGAACAAACC AAACTAAGTG AACTCCGTGC AAGCGTTGCA
 701  AGAAGCCTTT CGGATCTGGG GATGCATAAG GGAGAAATGA GTATTAAGGA
 751  TAACATGGAA GATTTAGTCT CTGCCCCATT ACCTGTTGAA GATGCTCTGA
 801  TTTCTTTGTT TGATTACAGT GATCGAACTG TTCAGCAGAA AGTGATTGAG
 851  ACATACATAT CACGATTGTA CCAGGTATTA TATCAACTAA CTTAATGTCT
 901  TCCATAGTCT CACTAAGCAT ATCTGATATG tTTAGATACC CTACATGGAA
 951  TGCTCATCTT TTCATTTGAC ACAAAGAAAC ATTGAGAAAT GAGATGCTGA
1001  CGATTGGCTG AAATTAACTG GGTnTGAGAA ATTGTGATCT CCCAACTTGT
1051  TAATGCACAA TGTTCTGGCT AACTTGCCAA TATTTTTCA GCCTCATCTT
1101  GTTnAGGATA GCAnCCAAAT GAAATCCAAG GATCTGGTGC TATTACTTTT
1151  TGGGAATTTA TGAAGGGC
```

FIG. 18B

```
  1  CTCCCAATAT TGTCATGAGG CTTGCATCCC AGGTTAGTTT TTTTTCCTTT
 51  CTGAAATTTA TATTCCATAC CTTTTCACCT TTAGTTATCC TTGTATTTTC
101  TGGAAGCTTC ATCTGATGCA TTATTGACAA ATGCACTAAT GGTCATCATA
151  TTTGGAGATT AACATATTTA TCTTAATTGA TGGGAACTCT TGAAAATGAC
201  AATGGTTGAG CAGATAATTA ACAGTTTTTT AATAAAAAAA CATGCATTTC
251  TAGGAGTTGG ACTAAGCTTT TCTTAGTATG AAGTGCCATG TTTTACATGG
301  TCCATTTGTG TCAATTTACA GTCGGTATCA TGGAAAGGTT GTCATAATGG
351  CTGGAGANAA ACAACACATC TTGTTTCTCA ACACTTGTGG GAGAAGANGT
401  TTTACCTTTT TTCCTAAAAT TACTTTTGT ACTAAATTGT ATAATTTTC
451  CAATATTCTC CATGATTATT GAACTCTGCT GTGTTCAAAC AGCCAAAACA
501  TGTTTCCATA CTTTACACCT TTATTTTTA GATGGAACCT GGAATTGTGC
551  TCTGTTATCT GTATCATGCA TATATTGATC TTAAACCTAT CTCTATTGTA
601  GAATCCGCAC TTGAATTCAG TTGCTTGTGA TCAATATG
```

FIG. 18C

```
  1 GGTAACCACC ACACCCGCGG CGCTTAATGG CCGTACAGGG NGGTCCCATT
 51 CGCCATTCAG GTGCGCAACT GTTGGGAAGG GCGATCGGTG CGGGCTTCTT
101 CGNTATTACG CCAGCTGGCG AAAGGGGGAT GTGCTGCAAG GCGATTAAGT
151 TGGGTAACGC CAGGGTTTTC CCAGTCACGA CGTTGTAAAA CGACGGCCAG
201 TGAGCGCGCG TAATACGACT CACTATAGGG CGAATTGGGT ACCGGCCCC
251 CCCTCGAGGT CGACCTGCAG GTCAACGGAT CCTAGGGGGC CAACAGATTC
301 TTATCAAATG AATGGATTA TCAATGAAAC ACATAATGGA AGACATGCCT
351 CAGTGTCCAA GGTTGTTGAA TTTTGTGCGG CACTAGGTGG CAAAACACCA
401 ATTCACAGTA TATTAGTGGC CAACAATGGA ATGGCAGCAG CAAAATTTAT
451 GAGGAGTGTC CGGACATGGG CTAATGATAC TTTTGGATCT GAGAAGGCAA
501 TTCAACTCAT AGCTATGGCA ACTCCGGAAG ACATGAGGTA AATGCAGAAC
551 ACATTAGA
```

FIG. 18D

```
  1  GAATAATCTG CCTGCAGCTC AAGTTGCTGT TGGAATGGGC ATACCTCTTT
 51  GGCAGATTCC AGGTAATTAC CAATTTACCA ACTTATTTAG TTCCTTATTG
101  TTTTATTCTC TAATTTTCTA CTTATGTAgA AATCAGACGT TTCTATGGAA
151  TGGACTATGG AGGAGGGTAT GACATTTGGA GGAAAACAGC AGCTCTTGCT
201  ACACCATTTA ATTTTGATGA AGTAgATTcT CAATGGCCAA AGGGCCATTG
251  TGTAgCAGTT AGAATTACTA GTGAGGACCC AGATGATGGT TTCAAACcTA
301  CTGGTGGGAA AGTGAAGGTA AGTTTTCTAG ATGACATGTA TTATATATCG
351  TTCAAAgAgA TTAAGTTTGG TTAAATGAcT AGGTCTTGAT TTTTTATCTT
401  TCAGGAGATA AGTTTTAAAA GCAAGCCTAA TGTTTGGGCC TaCTTCTCAG
451  TAAAGGTaAC TTGTTAACTT TAGTACGCTG TCACATTATt ctTCsTTGTG
501  .AAAATAAtT TGAACGGTtC TCTTTGTATT TTaACCAtCC AtCgTCTCAT
551  TTAsCAgAgC ACACAAATAT TtGCACTGAC CCCCcTcCCC tTATCtGCtT
601  TCAgTCTGGT GGAgGCATtC AtGAATTtGC TGATTCTCAG TTCGGTATGT
651  GTAAACCAAG AGTATTCTTT GTAATTTATA TTGGTCCTCA ATTTTGAAAT
701  ATTGcTCTTT CCGTTACAGG ACAwGTTTTT GCATATGGGC TCTCTAGATC
751  AGCAGCAATA ACAAACATGA CTCTTGCATT AAAAnAGATT CAAATTCGTG
801  GAGAAATTCA TTCAAATGTT TGATTACACA GTTGATCTCT TAAATGTTAA
851  GAAATATTAA CCACCTTTTA AATCACATTT TCCATTATGT TTGATTCCAT
901  ATCATTAATT TTGATTTTCT ATTATGGCTA AACCTGTGGT GCTATTTTCC
951  TATTATCCCA GGCTTCGAC TTTAGA
```

FIG. 18E

```
                                        GGATCC TAgGGGGCCA
1401 ACAGATTCTT ATCAAATGrA aTGGGATTAT CAATGAAACA CATAATGGAA
1451 GACATGCCTC AGTGTCCAAG GTTGTTGAAT TTTGTGCGGC ACTAGGTGGC
1501 AAAACACCAA TTCACAGTAT ATTAGTGGCC AACAATGGAA TGGCAGCAgC
1551 aAAATTTATG AggAGTGTCC GGACATGGGC TAATGATACT TTTGGATCTG
1601 AGAAgGCAAT TCAACTCATA GCTATgGCAA CTCCGGAAGA CATGAGGATA
1651 AATGCAGAAC ACATTAGAAT TGCTGACCAA TTaCGTAgAr gTGcctgGTG
1701 gaacaaACAA tA.ATAActA cgCCaATGTT CAAcTcATAg TGGAaGTTAG
1751 CCTTGcTAAT CTGTTAgTTT ACTACTGgTC tGCtGTTtCC TTtATTtGtt
1801 GTaTAATGAT tGACaTATTt AagTAgAgAA atTTATAtTT CtCctCtgCt
1851 GTTGTGgAag TCCAatTGTC acCATtAACt GTgAAaTATt gCAgATGGca
1901 CaAAAACtAG gTgtTTCTgC TGTTTGGCCT gGTTGGGGTC ATGCTTCTGA
1951 GAATCcTGAA CTGCCAGATG CATTGACCGC AAAAGGGATC GTTTTTCTTG
2001 GCCCACCTGc ATCATCAATG AATGCTTTGG GAGATAAGGT CGGCTCAGCT
2051 CTCATTGCTC AAGCAGCCGG GGtCCCAACT CTTGCTTGGA GTGGATCACA
2101 TGTGAGTCTC ACTCTTTGAT TACTATCCGC CTGTCTCATT GCTCTCTCTT
2151 TCATATTCTA ATGACACTAA ATTTAGGTTG AAGTTCCATT AGAGTGCTGC
2201 TTAGACGCGA TACCTGAGGA GATGTATAGA AAAGCTT
```

FIG. 18F

```
  1  AATTCCTGTG GGTGTTATAG CTGTGGAGAC ACAGACCATG ATGCAGCTCA
 51  TCCCTGCTGA TCCAGGTCAA CTTGATTCCC ATGAGCGATG TGTTCCTCGG
101  GCTGGACAAG TGTGGTTCCC AGATNCTGCA ACCAAGACAG CTCAGGCATT
151  ATTAGACTTC AACCGTGAAG GATTGCCTCT GTTCATCCTG GCTAACTGGA
201  GAGGCTtCTC TGGGGgACAG AGAGATCTCT T
```

FIG. 19A

```
  1  AATTCATGCA TCTTAATAAA CACAGTTGGC CCTTAAAGCA AGTGAACTTC
 51  TTGAACAAAC CAAACTAAGT GAACTCTGTT CCAGCATTGC AAGAAGCCTT
101  TCAGATCTGG GGATGCATAA GGGAGAAATG ACTATTAAGG ATAGCATGGA
151  AGATTTAGTC TCTGNCCCAT TGCCTGTTGA AGATGCTCTT ATTTCTTTGT
201  TTGATTA
```

FIG. 19B

```
  1  ATAGACCTGT CGCATACATC CCTGAGAACA CATGCGATCC GCGTGCAGCC
 51  ATCCGTGGnG TAGATGACAG CCAAGGGAAA TGGTTGGGTG GTATGTTTGA
101  CAAAGACAGC TTTGTGGAGA CATTTGAAGG ATGGGCAAAA ACAGTGGTTA
151  CTGGTAGAGC AAAGCTTGGA GGAAGGAATT
```

FIG. 19C

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 2001 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:1:

```
AGAGATGAAG CTCGCATGCC AATGCGCCAC ACATTCCTCT GGTTGGATGA CAAGAGTTGT      60
TATGAAGAAG AGCAGATTCT CCGGCATGTG GAGCCTCCCC TCTCTACACT TCTTGAATTG     120
GATAAGTTGA AGGTGAAAGG ATACAATGAA ATGAAGTATA CTCCTTCGCG TGACCGCCAA     180
TGGCATATCT ACACACTAAG AAATACTGAA AACCCCAAAA TGTTGCATAG GGTGTTTTTC     240
CGAACTATTG TCAGGCAACC CAATGCAGGC AACAAGTTTA GATCGGCTCA GATCAGCGAC     300
GCNAAGGTAG GATGTCCCGA AGAATCTCTT TCATTTACAT CAAATAGCAT CTTAAGATCA     360
TTGATGACTG CTATTGAAGA ATTAGAGCTT CATGCAATTA GGACAGGTCA TTCTCACATG     420
TATTTGTGCA TACTGAAAGA GCAAAAGCTT CTTGACCTCA TTCCATTTTC AGGGAGTACA     480
ATTGTTGATG TTGGCCAAGA TGAAGCTACC GCTTGTTCAC TTTTAAAATC AATGGCTTTG     540
AAGATACATG AGCTTGTTGG TGCAAGGATG CATCATCTGT CTGTATGCCA GTGGGAGGTG     600
AAACTCAAGT TGGACTGTGA TGGCCCTGCA AGTGGTACCT GGAGAGTTGT AACTACAAAT     660
GTTACTGGTC ACACCTGCAC CATTGATATA TACCGAGAAG TGGAGGAAAT AGAATCACAG     720
AAGTTAGTGT ACCATTCAGC CAGTTCGTCA GCTGGACCAT TGCATGGTGT TGCACTGAAT     780
AATCCATATC AACCTTTGAG TGTGATTGAT CTAAAGCGCT GCTCTGCTAG GAACAACAGA     840
ACAACATATT GCTATGATTT TCCGCTGGCC TTTGAAACTG CACTGCAGAA GTCATGGCAG     900
TCCAATGGCT CTACTGTTTC TGAAGGCAAT GAAAATAGTA AATCCTACGT GAAGGCAACT     960
GAGCTAGTGT TTGCTGAAAA ACATGGGTCC TGGGGCACTC CTATAATTCC GATGGAACGC    1020
CCTGCTGGGC TCAACGACAT TGGTATGGTC GCTTGGATCA TGGAGATGTC AACACCTGAA    1080
TTTCCCAATG GCAGGCAGAT TATTGTTGTA GCAAATGATA TCACTTTCAG AGCTGGATCA    1140
TTTGGCCCAA GGGAAGATGC ATTTTTTGAA ACTGTCACTA ACCTGGCTTG CGAAAGGAAA    1200
CTTCCTCTTA TATACTTGGC AGCAAACTCT GGTGCTAGGA TTGGCATAGC TGATGAAGTA    1260
AAATCTTGCT TCCGTGTTGG ATGGTCTGAC GAAGGCAGTC CTGAACGAGG GTTTCAGTAC    1320
ATCTATCTGA CTGAAGAAGA CTATGCTCGC ATTAGCTCTT CTGTTATAGC ACATAAGCTG    1380
GAGCTAGATA GTGGTGAAAT TAGGTGGATT ATTGACTCTG TTGTGGGCAA GGAGGATGGG    1440
CTTGGTGTCG AGAACATACA TGGAAGTGCT GCTATTGCCA GTGCTTATTC TAGGGCATAT    1500
GAGGAGACAT TTACACTTAC ATTTGTGACT GGGCGGACTG TAGGAATAGG AGCTTATCTT    1560
```

```
GCTCGACTTG GTATACGGTG CATACAGCGT CTTGACCAGC CTATTATTTT AACAGGGTTT    1620

TCTGCCCTGA ACAAGCTCCT TGGGCGGGAA GTGTACAGCT CCCACATGCA GCTTGGTGGT    1680

CCTAAGATCA TGGCGACCAA TGGTGTTGTC CACCTCACTG TTCCAGATGT CCTTGAAGGT    1740

GTTTCCAATA TATTGAGGTG GCTCAGCTAT GTTCCTGCAA ACATTGGTGG ACCTCTTCCT    1800

ATTACCAAAC CTCTGGACCC TCCAGACAGA CCTGTTGCTT ACATCCCTGA GAACACATGC    1860

GATCCACGTG CAGCTATCTG TGGTGTAGAT GACAGCCAAG GGAAATGGTT GGGTGGTATG    1920

TTTGACAAAG ACAGCTTTGT GGAGACATTT GAAGGATGGG CAAAAACAGT GGTTACTGGC    1980

AGAGCAAAGC TTGGAGGAAT T                                              2001
```

(2) INFORMATION FOR SEQ ID NO:2:

(i) SEQUENCE CHARACTERISTICS:
        (A) LENGTH: 258 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:2:

```
GTTCCTGCAA ACATTGGTGG ACCTCTTCCT ATTACCAAAC CTCTGGACCC TCCAGACAGA      60

CCTGTTGCTT ACATCCCTGA GAACACATGC GATCCACGTG CAGCTATCTG TGGTGTAGAT     120

GACAGCCAAG GGAAATGGTT GGGTGGTATG TTTGACAAAG ACAGCTTTGT GGAGACATTT     180

GAAGGATGGG CAAAAACAGT GGTTACTGGC AGAGCAAAGC TTGGAGGAAT TCCTGTGGGC     240

GTCATAGCTG TGGAGACA                                                   258
```

(2) INFORMATION FOR SEQ ID NO:3:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:3:

```
Val Met Lys Met
 1
```

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:4:

GCCAGATTCC ACCAAAGCAT ATATCC                                          26

(2) INFORMATION FOR SEQ ID NO:5:

(i) SEQUENCE CHARACTERISTICS:
        (A) LENGTH: 7470 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:5:

GGTCTTCAAT TGTGCTGTCT GGGCCACGGA ACGACAATGT CACAGCTTGG ATTAGCCGCA      60

GCTGCCTCAA AGGCCTTGCC ACTACTCCCT AATCGCCAGA GAAGTTCAGC TGGGACTACA     120

TTCTCATCAT CTTCATTATC GAGGCCCTTA AACAGAAGGA AAAGCCATAC TCGTTCACTC     180

CGTGATGGCG GAGATGGGGT ATCAGATGCC AAAAAGCACA GCCAGTCTGT TCGTCAAGGT     240

CTTGCTGGCA TTATCGACCT CCCAAGTGAG GCACCTTCCG AAGTGGATAT TTCACATGGA     300

TCTGAGGATC CTAGGGGGCC AACAGATTCT TATCAAATGA ATGGGATTAT CAATGAAACA     360

CATAATGGAA GACATGCCTC AGTGTCCAAG GTTGTTGAAT TTTGTGCGGC ACTAGGTGGC     420

AAAACACCAA TTCACAGTAT ATTAGTGGCC AACAATGGAA TGGCAGCAGC AAAATTTATG     480

AGGAGTGTCC GGACATGGGC TAATGATACT TTTGGATCTG AGAAGGCAAT TCAACTCATA     540

GCTATGGCAA CTCCGGAAGA CATGAGGATA AATGCAGAAC ACATTAGAAT TGCTGACCAA     600

TTCGTAGAGG TGCCTGGTGG AACAAACAAT AATAACTACG CCAATGTTCA ACTCATAGTG     660

GGGATGGCAC AAAAACTAGG TGTTTCTGCT GTTTGGCCTG GTTGGGGTCA TGCTTCTGAG     720

AATCCTGAAC TGCCAGATGC ATTGACCGCA AAAGGGATCG TTTTTCTTGG CCCACCTGCA     780

TCATCAATGA ATGCTTTGGG AGATAAGGTC GGCTCAGCTC TCATTGCTCA AGCAGCCGGG     840

GTCCCAACTC TTGCTTGGAG TGGATCACAT GTTGAAGTTC CATTAGAGTG CTGCTTAGAC     900

GCGATACCTG AGGAGATGTA TAGAAAAGCT TGCGTTACTA CCACAGAGGA AGCAGTTGCA     960

AGTTGTCAAG TGGTTGGTTA TCCTGCCATG ATTAAGGCAT CCTGGGGAGG TGGTGGTAAA    1020

GGAATAAGAA AGGTTCATAA TGATGATGAG GTTAGAGCGC TGTTTAAGCA AGTACAAGGT    1080

GAAGTCCCTG GCTCCCCAAT ATTTGTCATG AGGCTTGCAT CCCAGAGTCG GCATCTTGAA    1140

GTTCAGTTGC TTTGTGATCA ATATGGTAAT GTAGCAGCAC TTCACAGTCG TGATTGCAGT    1200

GTGCAACGGC GACACCAGAA GATTATTGAA GAAGGTCCAG TTACTGTTGC TCCTCGTGAG    1260

-continued

```
ACAGTTAAAG CACTTGAGCA GGCAGCAAGG AGGCTTGCTA AGGCTGTGGG TTATGTTGGT    1320

GCTGCTACTG TTGAGTATCT TTACAGCATG GAAACTGGAG ACTACTATTT TCTGGAACTT    1380

AATCCCCGAC TACAGGTTGA GCATCCAGTC ACTGAGTGGA TAGCTGAAGT GAATCTGCCT    1440

GCAGCTCAAG TTGCTGTTGG AATGGGCATA CCTCTTTGGC AGATTCCAGA AATCAGACGT    1500

TTCTATGGAA TGGACTATGG AGGAGGGTAT GACATTTGGA GGAAAACAGC AGCTCTTGCT    1560

ACACCATTTA ATTTTGATGA AGTAGATTCT CAATGGCCAA AGGGCCATTG TGTAGCAGTT    1620

AGAATTACTA GTGAGGACCC AGATGATGGT TTCAAACCTA CTGGTGGGAA AGTGAAGGAG    1680

ATAAGTTTTA AAAGCAAGCC TAATGTTTGG GCCTACTTCT CAGTAAAGTC TGGTGGAGGC    1740

ATTCATGAAT TTGCTGATTC TCAGTTTGGA CATGCTTTTG CATATGGACT CTCTAGACCA    1800

GCAGCTATAA CAAACATGTC TCTTGCATTA AAAGAGATTC AGATTCGTGG AGAAATTCAT    1860

TCAAATGTTG ATTACACAGT TGACCTCTTA AACGCTTCAG ACTTCAGAGA AAACAAGATC    1920

CACACTGGTT GGCTGGATAC AAGAATAGCT ATGCGTGTTC AAGCTGAGAG GCCCCCATGG    1980

TATATCTCAG TGGTTGGAGG TGCTTTATAT AAAACAGTAA CCACCAATGC AGCCACTGTT    2040

TCTGAATATG TTAGTTATCT CACCAAGGGC CATATTCCAC CAAAGCATAT ATCCCTTGTC    2100

AATTCTACAG TTAATTTGAA TATAGAAGGG AGCAAATACA CAATTGAAAC TGTAAGGACT    2160

GGACATGGTA GCTACAGGTT GAGAATGAAT GATTCAACAG TTGAAGCGAA TGTACAATCT    2220

TTATGTGATG GTGGCCTCTT AATGCAGTTG GATGGAAACA GCCATGTAAT TTATGCAGAA    2280

GAAGAAGCTG GTGGTACACG GCTTCAGATT GATGGAAAGA CATGTTTATT GCAGAATGAC    2340

CATGATCCAT CGAAGTTATT AGCTGAGACA CCCTGCAAAC TTCTTCGTTT CTTGGTTGCT    2400

GATGGTGCTC ATGTTGATGC GGATGTACCA TACGCGGAAG TTGAGGTTAT GAAGATGTGC    2460

ATGCCTCTCT TGTCACCTGC TTCTGGTGTC ATTCATTGTA TGATGTCTGA GGGCCAGGCA    2520

TTGCAGGCTG GTGATCTTAT AGCAAGGTTG GATCTTGATG ACCCTTCTGC TGTGAAAAGA    2580

GCTGAGCCAT TTGATGGAAT ATTTCCACAA ATGGAGCTCC CTGTTGCTGT CTCTAGTCAA    2640

GTACACAAAA GATATGCTGC AAGTTTGAAT GCTGCTCGAA TGGTCCTTGC AGGATATAGG    2700

CACAATATTA TGAAGTCGT TCAAGATTTG GTATGCTGCC TGGACAACCC TGAGCTTCCT    2760

TTCCTACAGT GGGATGAACT TATGTCTGTT CTAGCAACGA GGCTTCCAAG AAATCTCAAG    2820

AGTGAGTTAG AGGATAAATA CAAGGAATAC AAGTTGAATT TTTACCATGG AAAAAACGAG    2880

GACTTTCCAT CCAAGTTGCT AAGAGACATC ATTGAGGAAA TCTTTCTTA TGGTTCAGAG    2940

AAGGAAAAGG CTACAAATGA GAGGCTTGTT GAGCCTCTTA TGAACCTACT GAAGTCATAT    3000

GAGGGTGGGA GAGAGAGCCA TGCACATTTT GTTGTCAAGT CTCTTTTCGA GGAGTATCTT    3060

ACAGTGGAAG AACTTTTTAG TGATGGCATT CAGTCTGACG TGATTGAAAC ATTGCGGCAT    3120

CAGCACAGTA AAGACCTGCA GAAGGTTGTA GACATTGTGT TGTCTCACCA GGGTGTGAGG    3180

AACAAAGCTA AGCTTGTAAC GGCACTTATG GAAAAGCTGG TTTATCCAAA TCCTGGTGGT    3240

TACAGGGATC TGTTAGTTCG CTTTTCTTCC CTCAATCATA AAAGATATTA TAAGTTGGCC    3300

CTTAAAGCAA GTGAACTTCT TGAACAAACC AAACTAAGTG AACTCCGTGC AAGCGTTGCA    3360

AGAAGCCTTT CGGATCTGGG GATGCATAAG GGAGAAATGA GTATTAAGGA TAACATGGAA    3420

GATTTAGTCT CTGCCCCATT ACCTGTTGAA GATGCTCTGA TTTCTTTGTT TGATTACAGT    3480

GATCGAACTG TTCAGCAGAA AGTGATTGAG ACATACATAT CACGATTGTA CCAGCCTCAT    3540

CTTGTAAAGG ATAGCATCCA AATGAAATTC AAGGAATCTG GTGCTATTAC TTTTTGGGAA    3600

TTTTATGAAG GCATGTTGA TACTAGAAAT GGACATGGGG CTATTATTGG TGGGAAGCGA    3660
```

```
TGGGGTGCCA TGGTCGTTCT CAAATCACTT GAATCTGCGT CAACAGCCAT TGTGGCTGCA   3720

TTAAAGGATT CGGCACAGTT CAACAGCTCT GAGGGCAACA TGATGCACAT TGCATTATTG   3780

AGTGCTGAAA ATGAAAGTAA TATAAGTGGA ATAAGCAGTG ATGATCAAGC TCAACATAAG   3840

ATGGAAAAGC TTAGCAAGAT ACTGAAGGAT ACTAGCGTTG CAAGTGATCT CCAAGCTGCT   3900

GGTTTGAAGG TTATAAGTTG CATTGTTCAA AGAGATGAAG CTCGCATGCC AATGCGCCAC   3960

ACATTCCTCT GGTTGGATGA CAAGAGTTGT TATGAAGAAG AGCAGATTCT CCGGCATGTG   4020

GAGCCTCCCC TCTCTACACT TCTTGAATTG GATAAGTTGA AGGTGAAAGG ATACAATGAA   4080

ATGAAGTATA CTCCTTCGCG TGACCGCCAA TGGCATATCT ACACACTAAG AAATACTGAA   4140

AACCCCAAAA TGTTGCATAG GGTGTTTTTC GAACTATTG TCAGGCAACC CAATGCAGGC    4200

AACAAGTTTA GATCGGCTCA GATCAGCGAC GCTGAGGTAG GATGTCCCGA AGAATCTCTT   4260

TCATTTACAT CAAATAGCAT CTTAAGATCA TTGATGACTG CTATTGAAGA ATTAGAGCTT   4320

CATGCAATTA GGACAGGTGA TTCTCACATG TATTTGTGCA TACTGAAAGA GCAAAAGCTT   4380

CTTGACCTCA TTCCATTTTC AGGGAGTACA ATTGTTGATG TTGGCCAAGA TGAAGCTACC   4440

GCTTGTTCAC TTTTAAAATC AATGGCTTTG AAGATACATG AGCTTGTTGG TGCAAGGATG   4500

CATCATCTGT CTGTATGCCA GTGGGAGGTG AAACTCAAGT TGGACTGTGA TGGCCCTGCA   4560

AGTGGTACCT GGAGAGTTGT AACTACAAAT GTTACTGGTC ACACCTGCAC CATTGATATA   4620

TACCGAGAAG TGGAGGAAAT AGAATCACAG AAGTTAGTGT ACCATTCAGC CAGTTCGTCA   4680

GCTGGACCAT TGCATGGTGT TGCACTGAAT AATCCATATC AACCTTTGAG TGTGATTGAT   4740

CTAAAGCGCT GCTCTGCTAG GAACAACAGA ACAACATATT GCTATGATTT TCCGCTGGCC   4800

TTTGAAACTG CACTGCAGAA GTCATGGCAG TCCAATGGCT CTACTGTTTC TGAAGGCAAT   4860

GAAAATAGTA AATCCTACGT GAAGGCAACT GAGCTAGTGT TTGCTGAAAA ACATGGGTCC   4920

TGGGCACTC CTATAATTCC GATGGAACGC CCTGCTGGGC TCAACGACAT TGGTATGGTC     4980

GCTTGGATCA TGGAGATGTC AACACCTGAA TTTCCCAATG GCAGGCAGAT TATTGTTGTA   5040

GCAAATGATA TCACTTTCAG AGCTGGATCA TTTGGCCCAA GGGAAGATGC ATTTTTTGAA   5100

ACTGTCACTA ACCTGGCTTG CGAAAGGAAA CTTCCTCTTA TATACTTGGC AGCAAACTCT   5160

GGTGCTAGGA TTGGCATAGC TGATGAAGTA AAATCTTGCT TCCGTGTTGG ATGGTCTGAC   5220

GAAGGCAGTC CTGAACGAGG GTTTCAGTAC ATCTATCTGA CTGAAGAAGA CTATGCTCGC   5280

ATTAGCTCTT CTGTTATAGC ACATAAGCTG GAGCTAGATA GTGGTGAAAT TAGGTGGATT   5340

ATTGACTCTG TTGTGGGCAA GGAGGATGGG CTTGGTGTCG AGAACATACA TGGAAGTGCT   5400

GCTATTGCCA GTGCTTATTC TAGGGCATAT GAGGAGACAT TTACACTTAC ATTTGTGACT   5460

GGGCGGACTG TAGGAATAGG AGCTTATCTT GCTCGACTTG GTATACGGTG CATACAGCGT   5520

CTTGACCAGC CTATTATTTT AACAGGGTTT TCTGCCCTGA ACAAGCTCCT TGGGCGGGAA   5580

GTGTACAGCT CCCACATGCA GCTTGGTGGT CCTAAGATCA TGGCGACCAA TGGTGTTGTC   5640

CACCTCACTG TTCCAGATGT CCTTGAAGGT GTTTCCAATA TATTGAGGTG GCTCAGCTAT   5700

GTTCCTGCAA ACATTGGTGG ACCTCTTCCT ATTACCAAAC CTCTGGACCC TCCAGACAGA   5760

CCTGTTGCTT ACATCCCTGA GAACACATGC GATCCACGTG CAGCTATCTG TGGTGTAGAT   5820

GACAGCCAAG GGAAATGGTT GGGTGGTATG TTTGACAAAG ACAGCTTTGT GGAGACATTT   5880

GAAGGATGGG CAAAAACAGT GGTTACTGGC AGAGCAAAGC TTGGAGGAAT TCCTGTGGGC   5940

GTCATAGCTG TGGAGACACA GACCATGATG CAGATCATCC CTGCTGATCC AGGTCAGCTT   6000
```

```
GATTCCCATG AGCGATCTGT CCCTCGTGCT GGACAAGTGT GGTTCCCAGA TTCTGCAACC      6060

AAGACCGCTC AGGCATTATT AGACTTCAAC CGTGAAGGAT TGCCTCTGTT CATCCTGGCT      6120

AATTGGAGAG GCTTCTCTGG TGGACAAAGA GATCTCTTTG AAGGAATTCT TCAGGCTGGG      6180

TCAACAATTG TCGAGAACCT TAGGACATAT AATCAGCCTG CTTTTGTGTA CATTCCTATG      6240

GCTGGAGAGC TTCGTGGAGG AGCTTGGGTT GTGGTCGATA GCAAAATAAA TCCAGACCGC      6300

ATTGAGTGTT ATGCTGAAAG GACTGCCAAA GGTAATGTTC TCGAACCTCA AGGGTTAATT      6360

GAAATCAAGT TCAGGTCAGA GGAACTCCAA GACTGTATGG GTAGGCTTGA CCCAGAGTTG      6420

ATAAATCTGA AAGCAAAACT CCAAGATGTA AATCATGGAA ATGGAAGTCT ACCAGACATA      6480

GAAGGGATTC GGAAGAGTAT AGAAGCACGT ACGAAACAGT TGCTGCCTTT ATATACCCAG      6540

ATTGCAATAC GGTTTGCTGA ATTGCATGAT ACTTCCCTAA GAATGGCAGC TAAAGGTGTG      6600

ATTAAGAAAG TTGTAGACTG GAAGAATCA CGCTCGTTCT TCTATAAAAG GCTACGGAGG      6660

AGGATCGCAG AAGATGTTCT TGCAAAAGAA ATAAGGCAGA TAGTCGGTGA TAAATTTACG      6720

CACCAATTAG CAATGGAGCT CATCAAGGAA TGGTACCTTG CTTCTCAGGC CACAACAGGA      6780

AGCACTGGAT GGGATGACGA TGATGCTTTT GTTGCCTGGA AGGACAGTCC TGAAAACTAC      6840

AAGGGGCATA TCCAAAAGCT TAGGGCTCAA AAAGTGTCTC ATTCGCTCTC TGATCTTGCT      6900

GACTCCAGTT CAGATCTGCA AGCATTCTCG CAGGGTCTTT CTACGCTATT AGATAAGATG      6960

GATCCCTCTC AGAGAGCGAA GTTTGTTCAG GAAGTCAAGA AGGTCCTTGA TTGATGATAC      7020

CAACACATCC AACACAATGT GTGCATGTCA CATCTTTTTG TTCTAGTACA TACATAGAAG      7080

GATATTGCTT GGTCTTGATT GATCATGTCT GATTTAAGTC GACTATTATT TCTTGGAATT      7140

TTCTTTTGGA CCTGGTGCTA TGGTTGATGG ATGTATATTG GATATGTGCG TTCTGCCAGG      7200

TGTAAGCACA AAGGTTTAGA CARAMMRARA RCAAGAGCGA GTGAACCTGT TCTGGTTTTG      7260

CAGTGGTTCA GTAAGGCAGA AAGTTGTTAA ACCGTAGTTC TGAGATGTAT TACCAGTGNC      7320

GCCATGCTGT ACTTTTAGGG TGTATAATGC GGATACAAAT AAACAATTTA GCGGTTCATT      7380

AAAGTTTGAA CTCAAATAAC ATGTTCTTTG TAAGCATATG TACCGTACCT CTACGTGAAA      7440

TAAAGTTGTT GAATTAGCAT TCGAAAAAAA                                      7470
```

(2) INFORMATION FOR SEQ ID NO:6:

(i) SEQUENCE CHARACTERISTICS:
        (A) LENGTH: 2325 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal and C-terminal (full length protein)

(vi) ORIGINAL SOURCE:

(xi) SEQUENCE DESCRIPTION: SEQ ID NO:6:

```
Met Ser Gln Leu Gly Leu Ala Ala Ala Ala Ser Lys Ala Leu Pro Leu
 1               5                  10                  15

Leu Pro Asn Arg Gln Arg Ser Ser Ala Gly Thr Thr Phe Ser Ser Ser
                20                  25                  30

Ser Leu Ser Arg Pro Leu Asn Arg Arg Lys Ser His Thr Arg Ser Leu
        35                  40                  45
```

-continued

```
Arg Asp Gly Gly Asp Gly Val Ser Asp Ala Lys Lys His Ser Gln Ser
 50                  55                  60
Val Arg Gln Gly Leu Ala Gly Ile Ile Asp Leu Pro Ser Glu Ala Pro
 65                  70                  75                  80
Ser Glu Val Asp Ile Ser His Gly Ser Glu Asp Pro Arg Gly Pro Thr
                     85                  90                  95
Asp Ser Tyr Gln Met Asn Gly Ile Ile Asn Glu Thr His Asn Gly Arg
                100                 105                 110
His Ala Ser Val Ser Lys Val Val Glu Phe Cys Ala Ala Leu Gly Gly
            115                 120                 125
Lys Thr Pro Ile His Ser Ile Leu Val Ala Asn Asn Gly Met Ala Ala
130                 135                 140
Ala Lys Phe Met Arg Ser Val Arg Thr Trp Ala Asn Asp Thr Phe Gly
145                 150                 155                 160
Ser Glu Lys Ala Ile Gln Leu Ile Ala Met Ala Thr Pro Glu Asp Met
                165                 170                 175
Arg Ile Asn Ala Glu His Ile Arg Ile Ala Asp Gln Phe Val Glu Val
            180                 185                 190
Pro Gly Gly Thr Asn Asn Asn Asn Tyr Ala Asn Val Gln Leu Ile Val
        195                 200                 205
Gly Met Ala Gln Lys Leu Gly Val Ser Ala Val Trp Pro Gly Trp Gly
210                 215                 220
His Ala Ser Glu Asn Pro Glu Leu Pro Asp Ala Leu Thr Ala Lys Gly
225                 230                 235                 240
Ile Val Phe Leu Gly Pro Pro Ala Ser Ser Met Asn Ala Leu Gly Asp
                245                 250                 255
Lys Val Gly Ser Ala Leu Ile Ala Gln Ala Ala Gly Val Pro Thr Leu
            260                 265                 270
Ala Trp Ser Gly Ser His Val Glu Val Pro Leu Glu Cys Cys Leu Asp
        275                 280                 285
Ala Ile Pro Glu Glu Met Tyr Arg Lys Ala Cys Val Thr Thr Thr Glu
290                 295                 300
Glu Ala Val Ala Ser Cys Gln Val Val Gly Tyr Pro Ala Met Ile Lys
305                 310                 315                 320
Ala Ser Trp Gly Gly Gly Gly Lys Gly Ile Arg Lys Val His Asn Asp
                325                 330                 335
Asp Glu Val Arg Ala Leu Phe Lys Gln Val Gln Gly Glu Val Pro Gly
            340                 345                 350
Ser Pro Ile Phe Val Met Arg Leu Ala Ser Gln Ser Arg His Leu Glu
        355                 360                 365
Val Gln Leu Leu Cys Asp Gln Tyr Gly Asn Val Ala Ala Leu His Ser
370                 375                 380
Arg Asp Cys Ser Val Gln Arg Arg His Gln Lys Ile Ile Glu Glu Gly
385                 390                 395                 400
Pro Val Thr Val Ala Pro Arg Glu Thr Val Lys Ala Leu Glu Gln Ala
                405                 410                 415
Ala Arg Arg Leu Ala Lys Ala Val Gly Tyr Val Gly Ala Ala Thr Val
            420                 425                 430
Glu Tyr Leu Tyr Ser Met Glu Thr Gly Asp Tyr Tyr Phe Leu Glu Leu
        435                 440                 445
Asn Pro Arg Leu Gln Val Glu His Pro Val Thr Glu Trp Ile Ala Glu
450                 455                 460
```

-continued

```
Val Asn Leu Pro Ala Ala Gln Val Ala Val Gly Met Gly Ile Pro Leu
465                 470                 475                 480

Trp Gln Ile Pro Glu Ile Arg Arg Phe Tyr Gly Met Asp Tyr Gly Gly
                485                 490                 495

Gly Tyr Asp Ile Trp Arg Lys Thr Ala Ala Leu Ala Thr Pro Phe Asn
            500                 505                 510

Phe Asp Glu Val Asp Ser Gln Trp Pro Lys Gly His Cys Val Ala Val
        515                 520                 525

Arg Ile Thr Ser Glu Asp Pro Asp Asp Gly Phe Lys Pro Thr Gly Gly
    530                 535                 540

Lys Val Lys Glu Ile Ser Phe Lys Ser Lys Pro Asn Val Trp Ala Tyr
545                 550                 555                 560

Phe Ser Val Lys Ser Gly Gly Ile His Glu Phe Ala Asp Ser Gln
                565                 570                 575

Phe Gly His Ala Phe Ala Tyr Gly Leu Ser Arg Pro Ala Ala Ile Thr
            580                 585                 590

Asn Met Ser Leu Ala Leu Lys Glu Ile Gln Ile Arg Gly Glu Ile His
            595                 600                 605

Ser Asn Val Asp Tyr Thr Val Asp Leu Leu Asn Ala Ser Asp Phe Arg
    610                 615                 620

Glu Asn Lys Ile His Thr Gly Trp Leu Asp Thr Arg Ile Ala Met Arg
625                 630                 635                 640

Val Gln Ala Glu Arg Pro Pro Trp Tyr Ile Ser Val Val Gly Gly Ala
                645                 650                 655

Leu Tyr Lys Thr Val Thr Thr Asn Ala Ala Thr Val Ser Glu Tyr Val
            660                 665                 670

Ser Tyr Leu Thr Lys Gly His Ile Pro Pro Lys His Ile Ser Leu Val
        675                 680                 685

Asn Ser Thr Val Asn Leu Asn Ile Glu Gly Ser Lys Tyr Thr Ile Glu
    690                 695                 700

Thr Val Arg Thr Gly His Gly Ser Tyr Arg Leu Arg Met Asn Asp Ser
705                 710                 715                 720

Thr Val Glu Ala Asn Val Gln Ser Leu Cys Asp Gly Gly Leu Leu Met
                725                 730                 735

Gln Leu Asp Gly Asn Ser His Val Ile Tyr Ala Glu Glu Ala Gly
            740                 745                 750

Gly Thr Arg Leu Gln Ile Asp Gly Lys Thr Cys Leu Leu Gln Asn Asp
        755                 760                 765

His Asp Pro Ser Lys Leu Leu Ala Glu Thr Pro Cys Lys Leu Leu Arg
    770                 775                 780

Phe Leu Val Ala Asp Gly Ala His Val Asp Ala Asp Val Pro Tyr Ala
785                 790                 795                 800

Glu Val Glu Val Met Lys Met Cys Met Pro Leu Leu Ser Pro Ala Ser
                805                 810                 815

Gly Val Ile His Cys Met Met Ser Glu Gly Gln Ala Leu Gln Ala Gly
            820                 825                 830

Asp Leu Ile Ala Arg Leu Asp Leu Asp Asp Pro Ser Ala Val Lys Arg
        835                 840                 845

Ala Glu Pro Phe Asp Gly Ile Phe Pro Gln Met Glu Leu Pro Val Ala
    850                 855                 860

Val Ser Ser Gln Val His Lys Arg Tyr Ala Ala Ser Leu Asn Ala Ala
865                 870                 875                 880

Arg Met Val Leu Ala Gly Tyr Glu His Asn Ile Asn Glu Val Val Gln
```

-continued

```
                885                 890                 895
Asp Leu Val Cys Cys Leu Asp Asn Pro Glu Leu Pro Phe Leu Gln Trp
                900                 905                 910
Asp Glu Leu Met Ser Val Leu Ala Thr Arg Leu Pro Arg Asn Leu Lys
                915                 920                 925
Ser Glu Leu Glu Asp Lys Tyr Lys Glu Tyr Lys Leu Asn Phe Tyr His
                930                 935                 940
Gly Lys Asn Glu Asp Phe Pro Ser Lys Leu Leu Arg Asp Ile Ile Glu
945                 950                 955                 960
Glu Asn Leu Ser Tyr Gly Ser Glu Lys Glu Lys Ala Thr Asn Glu Arg
                965                 970                 975
Leu Val Glu Pro Leu Met Asn Leu Leu Lys Ser Tyr Glu Gly Gly Arg
                980                 985                 990
Glu Ser His Ala His Phe Val Val Lys Ser Leu Phe Glu Glu Tyr Leu
                995                 1000                1005
Thr Val Glu Glu Leu Phe Ser Asp Gly Ile Gln Ser Asp Val Ile Glu
                1010                1015                1020
Thr Leu Arg His Gln His Ser Lys Asp Leu Gln Lys Val Val Asp Ile
1025                1030                1035                1040
Val Leu Ser His Gln Gly Val Arg Asn Lys Ala Lys Leu Val Thr Ala
                1045                1050                1055
Leu Met Glu Lys Leu Val Tyr Pro Asn Pro Gly Gly Tyr Arg Asp Leu
                1060                1065                1070
Leu Val Arg Phe Ser Ser Leu Asn His Lys Arg Tyr Tyr Lys Leu Ala
                1075                1080                1085
Leu Lys Ala Ser Glu Leu Leu Glu Gln Thr Lys Leu Ser Glu Leu Arg
                1090                1095                1100
Ala Ser Val Ala Arg Ser Leu Ser Asp Leu Gly Met His Lys Gly Glu
1105                1110                1115                1120
Met Ser Ile Lys Asp Asn Met Glu Asp Leu Val Ser Ala Pro Leu Pro
                1125                1130                1135
Val Glu Asp Ala Leu Ile Ser Leu Phe Asp Tyr Ser Asp Arg Thr Val
                1140                1145                1150
Gln Gln Lys Val Ile Glu Thr Tyr Ile Ser Arg Leu Tyr Gln Pro His
                1155                1160                1165
Leu Val Lys Asp Ser Ile Gln Met Lys Phe Lys Glu Ser Gly Ala Ile
                1170                1175                1180
Thr Phe Trp Glu Phe Tyr Glu Gly His Val Asp Thr Arg Asn Gly His
1185                1190                1195                1200
Gly Ala Ile Ile Gly Gly Lys Arg Trp Gly Ala Met Val Val Leu Lys
                1205                1210                1215
Ser Leu Glu Ser Ala Ser Thr Ala Ile Val Ala Ala Leu Lys Asp Ser
                1220                1225                1230
Ala Gln Phe Asn Ser Ser Glu Gly Asn Met Met His Ile Ala Leu Leu
                1235                1240                1245
Ser Ala Glu Asn Glu Ser Asn Ile Ser Gly Ile Ser Ser Asp Asp Gln
                1250                1255                1260
Ala Gln His Lys Met Glu Lys Leu Ser Lys Ile Leu Lys Asp Thr Ser
1265                1270                1275                1280
Val Ala Ser Asp Leu Gln Ala Ala Gly Leu Lys Val Ile Ser Cys Ile
                1285                1290                1295
Val Gln Arg Asp Glu Ala Arg Met Pro Met Arg His Thr Phe Leu Trp
                1300                1305                1310
```

-continued

```
Leu Asp Asp Lys Ser Cys Tyr Glu Glu Glu Gln Ile Leu Arg His Val
        1315                1320                1325

Glu Pro Pro Leu Ser Thr Leu Leu Glu Leu Asp Lys Leu Lys Val Lys
        1330                1335                1340

Gly Tyr Asn Glu Met Lys Tyr Thr Pro Ser Arg Asp Arg Gln Trp His
1345                1350                1355                1360

Ile Tyr Thr Leu Arg Asn Thr Glu Asn Pro Lys Met Leu His Arg Val
                1365                1370                1375

Phe Phe Arg Thr Ile Val Arg Gln Pro Asn Ala Gly Asn Lys Phe Arg
            1380                1385                1390

Ser Ala Gln Ile Ser Asp Ala Glu Val Gly Cys Pro Glu Glu Ser Leu
            1395                1400                1405

Ser Phe Thr Ser Asn Ser Ile Leu Arg Ser Leu Met Thr Ala Ile Glu
        1410                1415                1420

Glu Leu Glu Leu His Ala Ile Arg Thr Gly His Ser His Met Tyr Leu
1425                1430                1435                1440

Cys Ile Leu Lys Glu Gln Lys Leu Leu Asp Leu Ile Pro Phe Ser Gly
            1445                1450                1455

Ser Thr Ile Val Asp Val Gly Gln Asp Glu Ala Thr Ala Cys Ser Leu
            1460                1465                1470

Leu Lys Ser Met Ala Leu Lys Ile His Glu Leu Val Gly Ala Arg Met
        1475                1480                1485

His His Leu Ser Val Cys Gln Trp Glu Val Lys Leu Lys Leu Asp Cys
            1490                1495                1500

Asp Gly Pro Ala Ser Gly Thr Trp Arg Val Val Thr Thr Asn Val Thr
1505                1510                1515                1520

Gly His Thr Cys Thr Ile Asp Ile Tyr Arg Glu Val Glu Glu Ile Glu
            1525                1530                1535

Ser Gln Lys Leu Val Tyr His Ser Ala Ser Ser Ala Gly Pro Leu
            1540                1545                1550

His Gly Val Ala Leu Asn Asn Pro Tyr Gln Pro Leu Ser Val Ile Asp
            1555                1560                1565

Leu Lys Arg Cys Ser Ala Arg Asn Asn Arg Thr Thr Tyr Cys Tyr Asp
        1570                1575                1580

Phe Pro Leu Ala Phe Glu Thr Ala Leu Gln Lys Ser Trp Gln Ser Asn
1585                1590                1595                1600

Gly Ser Thr Val Ser Glu Gly Asn Glu Asn Ser Lys Ser Tyr Val Lys
                1605                1610                1615

Ala Thr Glu Leu Val Phe Ala Gly Lys His Gly Ser Trp Gly Thr Pro
            1620                1625                1630

Ile Ile Pro Met Glu Arg Pro Ala Gly Leu Asn Asp Ile Gly Met Val
        1635                1640                1645

Ala Trp Ile Met Glu Met Ser Thr Pro Glu Phe Pro Asn Gly Arg Gln
        1650                1655                1660

Ile Ile Val Val Ala Asn Asp Ile Thr Phe Arg Ala Gly Ser Phe Gly
1665                1670                1675                1680

Pro Arg Glu Asp Ala Phe Phe Glu Thr Val Thr Asn Leu Ala Cys Glu
            1685                1690                1695

Arg Lys Leu Pro Leu Ile Tyr Leu Ala Ala Asn Ser Gly Ala Arg Ile
            1700                1705                1710

Gly Ile Ala Asp Glu Val Lys Ser Cys Phe Arg Val Gly Trp Ser Asp
        1715                1720                1725
```

```
Glu Gly Ser Pro Glu Arg Gly Phe Gln Tyr Ile Tyr Leu Thr Glu Glu
    1730                1735                1740
Asp Tyr Ala Arg Ile Ser Ser Val Ile Ala His Lys Leu Glu Leu
1745                1750                1755                1760
Asp Ser Gly Glu Ile Arg Trp Ile Ile Asp Ser Val Val Gly Lys Glu
                1765                1770                1775
Asp Gly Leu Gly Val Glu Asn Ile His Gly Ser Ala Ala Ile Ala Ser
    1780                1785                1790
Ala Tyr Ser Arg Ala Tyr Glu Glu Thr Phe Thr Leu Thr Phe Val Thr
        1795                1800                1805
Gly Arg Thr Val Gly Ile Gly Ala Tyr Leu Ala Arg Leu Gly Ile Arg
    1810                1815                1820
Cys Ile Gln Arg Leu Asp Gln Pro Ile Ile Leu Thr Gly Phe Ser Ala
1825                1830                1835                1840
Leu Asn Lys Leu Leu Gly Arg Glu Val Tyr Ser Ser His Met Gln Leu
                1845                1850                1855
Gly Gly Pro Lys Ile Met Ala Thr Asn Gly Val Val His Leu Thr Val
            1860                1865                1870
Pro Asp Val Leu Glu Gly Val Ser Asn Ile Leu Arg Trp Leu Ser Tyr
    1875                1880                1885
Val Pro Ala Asn Ile Gly Gly Pro Leu Pro Ile Thr Lys Pro Leu Asp
    1890                1895                1900
Pro Pro Asp Arg Pro Val Ala Tyr Ile Pro Glu Asn Thr Cys Asp Pro
1905                1910                1915                1920
Arg Ala Ala Ile Cys Gly Val Asp Asp Ser Gln Gly Lys Trp Leu Gly
                1925                1930                1935
Gly Met Phe Asp Lys Asp Ser Phe Val Glu Thr Phe Glu Gly Trp Ala
                1940                1945                1950
Lys Thr Val Val Thr Gly Arg Ala Lys Leu Gly Gly Ile Pro Val Gly
                1955                1960                1965
Val Ile Ala Val Glu Thr Gln Thr Met Met Gln Ile Ile Pro Ala Asp
    1970                1975                1980
Pro Gly Gln Leu Asp Ser His Glu Arg Ser Val Pro Arg Ala Gly Gln
1985                1990                1995                2000
Val Trp Phe Pro Asp Ser Ala Thr Lys Thr Ala Gln Ala Leu Leu Asp
                2005                2010                2015
Phe Asn Arg Glu Gly Leu Pro Leu Phe Ile Leu Ala Asn Trp Arg Gly
                2020                2025                2030
Phe Ser Gly Gly Gln Arg Asp Leu Phe Glu Gly Ile Leu Gln Ala Gly
                2035                2040                2045
Ser Thr Ile Val Glu Asn Leu Arg Thr Tyr Asn Gln Pro Ala Phe Val
    2050                2055                2060
Tyr Ile Pro Met Ala Gly Glu Leu Arg Gly Gly Ala Trp Val Val Val
2065                2070                2075                2080
Asp Ser Lys Ile Asn Pro Asp Arg Ile Glu Cys Tyr Ala Glu Arg Thr
                2085                2090                2095
Ala Lys Gly Asn Val Leu Glu Pro Gln Gly Leu Ile Glu Ile Lys Phe
            2100                2105                2110
Arg Ser Glu Glu Leu Gln Asp Cys Met Gly Arg Leu Asp Pro Glu Leu
        2115                2120                2125
Ile Asn Leu Lys Ala Lys Leu Gln Asp Val Asn His Gly Asn Gly Ser
    2130                2135                2140
Leu Pro Asp Ile Glu Gly Ile Arg Lys Ser Ile Glu Ala Arg Thr Lys
```

```
                    2145               2150               2155                    2160

Gln Leu Leu Pro Leu Tyr Thr Gln Ile Ala Ile Arg Phe Ala Glu Leu
                    2165               2170               2175

His Asp Thr Ser Leu Arg Met Ala Ala Lys Gly Val Ile Lys Lys Val
                    2180               2185               2190

Val Asp Trp Glu Glu Ser Arg Ser Phe Phe Tyr Lys Arg Leu Arg Arg
                    2195               2200               2205

Arg Ile Ala Glu Asp Val Leu Ala Lys Glu Ile Arg Gln Ile Val Gly
                    2210               2215               2220

Asp Lys Phe Thr His Gln Leu Ala Met Glu Leu Ile Lys Glu Trp Tyr
2225               2230               2235                    2240

Leu Ala Ser Gln Ala Thr Thr Gly Ser Thr Gly Trp Asp Asp Asp
                    2245               2250               2255

Ala Phe Val Ala Trp Lys Asp Ser Pro Glu Asn Tyr Lys Gly His Ile
                    2260               2265               2270

Gln Lys Leu Arg Ala Gln Lys Val Ser His Ser Leu Ser Asp Leu Ala
                    2275               2280               2285

Asp Ser Ser Ser Asp Leu Gln Ala Phe Ser Gln Gly Leu Ser Thr Leu
                    2290               2295               2300

Leu Asp Lys Met Asp Pro Ser Gln Arg Ala Lys Phe Val Gln Glu Val
2305               2310               2315                    2320

Lys Lys Val Leu Asp
                    2325

(2) INFORMATION FOR SEQ ID NO:7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:7:

GGTCTTCAAT TGTGCTGTCT GG                                                      22

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:8:
```

```
CCTTGACGAA CAGACTGGCT GTGC                                          24
```

(2) INFORMATION FOR SEQ ID NO:9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:9:

```
CACAGCCAGT CTGTTCGTCA AGG                                           23
```

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:10:

```
CCTCTACGTA ATTGGTCAGC                                               20
```

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:11:

```
CATAGCTATG GCAACTCCGG                                               20
```

(2) INFORMATION FOR SEQ ID NO:12:

(i) SEQUENCE CHARACTERISTICS:
        (A) LENGTH: 3488 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:12:

| | | | | | |
|---|---|---|---|---|---|
| AAGCTTGGTA | TGGATTCGTC | AGCGCCAAGC | CGGGGTTTTG | CATGCGCCCG | ACTGGAARCS | 60 |
| GAATTCCGTG | AGCCCTGTAC | RRCAATGGCA | ACCCCASGGT | TACTGGGGTG | GCTGAATGGT | 120 |
| CTCSGCTTAC | GCAATTGTTT | GTGGCAGCWG | CGTGGGCTAA | ATGTARGTTG | TCTCTTGTTG | 180 |
| CACTGCARGA | TGGATGGGTA | GCCTCTGGGC | CGCCTCTGCT | ARTGTCTARC | GTTTGCTGAC | 240 |
| TGTGGTTTAT | TCAGGGATGC | CCATGCCCAT | GCTAGATTGA | TAGGTGCCAT | TCTAATGGTA | 300 |
| GGTGGCGGTA | AGGTTTATTA | AGCTGYAGYA | TCAGTAGGTA | ACCTCATGAA | TCAGGGTTTA | 360 |
| AGCACACCTT | TTCCTTTGTG | TGGGTGCATA | AGGAATGCAC | TTGGCTTCGT | TCCCTGATAG | 420 |
| TCTTTGSTCA | TGTGTCATTC | TACCAAGTGG | GTTACTGTAA | CATTGCACTC | TATGATGGTT | 480 |
| GGTGGTTGTG | CATCTTTYTG | CTYCCCCTGG | YTGTCTAATA | CCTGCATGTA | ACTGATGACC | 540 |
| YYCYTTTATG | TATCATATAG | ATTACATCCT | TTTGTTGTAC | ATCTCAATTC | TGAAAAAACA | 600 |
| ATGTTTTGCA | TTCTTAGCGC | TCTGTGCACA | AGGAAAAGGA | GGTTTTACCT | GCAACTTTTT | 660 |
| TTTTCGAGAA | AAAACAAACC | TTTCTGAAAG | GCAGTGATCA | TTTAGTATAA | AGAAAATTTG | 720 |
| ATTTACTTTC | TTCAGAGAGA | ATATKCCAAR | CAAACAATTT | TCTTACTGTC | TGAGCCACGA | 780 |
| AATTTGATCT | TGATCTTACT | TTCACAAGCC | ACATGAAGCC | TTATCATCGC | TCTGATAAAA | 840 |
| AARCCAAATA | GGTGATTCAT | AGAATGAGAR | AAAGAACCTG | TTGCCATTTG | GGGACCTTGT | 900 |
| TGTGTACTCA | TTATCCCCCC | TGCTCAGGTT | GAGGTTTCCT | TGCCACTGCC | ACCCCTTGGC | 960 |
| CCCTTCTTAT | ACAACCATCT | CCATTGAAAA | AGATTTTGCA | CTACATTTGG | GCTTCGTATG | 1020 |
| ACAAAAAAGG | AAAATAAAAC | TAAACAGCAG | AAACATAGTA | TAATTATAGG | TAAAAGGTTC | 1080 |
| TGGCAAGTTT | GAGTGGAAGA | GACCTTTGTA | TATTTGGACA | TATTTCACTA | GTAAATAGTT | 1140 |
| TTCTAAAATC | TTCATGAATG | GTGGCCAATA | AACTTGATAA | GATCTCAACA | TGGCAGGTTC | 1200 |
| CTTCMAAATG | AGAGGAAAAC | TGGAAACATC | ACAAATATTT | TTTAGCGAGT | GGCCTATAAA | 1260 |
| TTATAATGTT | GCTTTCATTT | CTTTGATATT | CAAAACTTCC | TAAGAGTATT | CTGCTAGAGC | 1320 |
| TCTGATGGTG | TCTTTTGCCT | CTGTCAGATT | TTCCAGGAGT | TTTCTTCCCT | TTTTATGGCA | 1380 |
| CTGTGCGTTT | GAGAAGGTCT | TCAATTGTGC | TGTCTGGGCC | ACGGAACGAC | AATGTCACAG | 1440 |
| CTTGGATTAG | CCGCAGCTGC | CTCAAAGGCC | TTGCCACTAC | TCCCTAATCG | CCAGAGAAGT | 1500 |
| TCAGCTGGGA | CTACATTCTC | ATCATCTTCA | TTATCGAGGC | CCTTAAACAG | AAGGAAAAGC | 1560 |
| CATACTCGTT | CACTCCGTGA | TGGCGGAGAT | GGGGTATCAG | ATGCCAAAAA | GCACAGCCAG | 1620 |
| TCTGTTCGTC | AAGGTACTGT | GAATATCTTT | TGATACAAGC | TAAAATTTTG | CTACAGAATA | 1680 |
| TATATTTAAA | GAGTTCTTTC | TTGGCTGGTG | TTGTTTATTT | GTTAACATS | CGAAAGGGCC | 1740 |
| TCTAGTTGGA | TTGGTTAGGT | GGSCTGAATA | CCACTCCTTA | AGGTCTTGAG | TTTGCTTTTC | 1800 |
| CCCNCGGAGC | GAATTTTAGG | CTAGGGTTAC | CCCCCCACCC | CCACCCGAAT | CTGCACAGYC | 1860 |
| CGGYCGYGGY | CGYCCTCATA | TAGGCTACGA | TGTCATTGTG | TATCGGCGGG | CCAGGGGTTT | 1920 |
| AAGAGTTTTC | TTGACCTTTG | TTAGAAGATC | TTAATAATAC | AATGTCCAAG | GGCTGTCTTA | 1980 |

-continued

| | |
|---|---|
| CCCTGTAGGT CGAGTTTTTA GTTGTTTTAA CATGGTAATG TTTGAAGCCT CATTCTAGGT | 2040 |
| RCCAATATAG ATATGCTCAC TGCTCAGTTT CAAATGTTTG TCTGCATGTA GGTCTTGCTG | 2100 |
| GCATTATCGA CCTCCCAAGT GAGGCACCTT CCGAAGTGGA TATTTCACAG TAAGGACTAC | 2160 |
| AATATTTTGC GTACGTTTGT TTTGGAAAAA GAAAATATTC TCAGCTTATT TATACTAGCT | 2220 |
| TCGCTAATAC TGAAATGCTG TCTTAATGTC CTGGTGCTGT ATGCTCAATC TTTCATAGTA | 2280 |
| AATGCTGCAA ATATGTGAT GTAACTGTTG CAACACAGCC AGGGACCTGT TATTTAGAGC | 2340 |
| ATGGTGAATG CTCTGGTTCA GTTATATGAT GTAGTTATAG CTCATGTTGA AGAATTAGTT | 2400 |
| GCAGTGTTTG CTGGACAATG GTCACTTATT ATAAATCATA TCTGCATACA CATTTGTGAC | 2460 |
| TTCTGTTGCT GTAAATGCCC GCATTTTTTG AGAAAAATTT AAATGCTTGG CCTAAATTGG | 2520 |
| ACATATATGA TAGACAAAGC TGATTTGAAC TTTGTTTATT TTTGACATCC ATGCATATTG | 2580 |
| TCAGTGTTGT GAAAACAATA CTAATCCTTT TTTTTTGTCT TTTTCCAGTG GATCTGAGGA | 2640 |
| TCCTAGGGGG CCAACAGATT CTTATCAAAT GAATGGGATT ATCAATGAAA CACATAATGG | 2700 |
| AAGACATGCC TCAGTGTCCA AGGTTGTTGA ATTTTGTGCG GCACTAGGTG GCAAAACACC | 2760 |
| AATTCACAGT ATATTAGTGG CCAACAATGG AATGGCAGCA CCCAAATTTA TGAGGAGTGT | 2820 |
| CCGGACATGG GCTAATGATA CTTTTGGATC TGAGAAGGCA ATTCAACTCA TAGCTATGGC | 2880 |
| AACTCCGGAA GACATGAGGA TAAATGCAGA ACACATTAGA ATTGCTGACC AATTACGTAG | 2940 |
| AGGTGCCTGG TGGAACAAAC AATAATAACT ACGCCAATGT TCAACTCATA GTGGAGGTTA | 3000 |
| GCCTTGCTAA TCTGTTAGTT TACTACTGGT CTGCTGTTTC CTTTATTTGT TGTATAATGA | 3060 |
| TTGACATATT TAAGTAGAGA AATTTATATT TCTCCTCTGC TGTTGTGGAA GTCCAATTGT | 3120 |
| CATCATTAAC TGTGAAATAT TGCAGATGGC ACAAAAACTA GGTGTTTCTG CTGTTTGGCC | 3180 |
| TGGTTGGGGT CATGCTTCTG AGAATCCTGA ACTGCCAGAT GCATTGACCG CAAAAGGGAT | 3240 |
| CGTTTTTCTT GGCCCACCTG SATCATCAAT GAATGCTTTG GGAGATAAGG TCGGCTCAGC | 3300 |
| TCTCATTGCT CAAGCAGCCG GGGNCCCAAC TCTTGCTTGG AGTGGATCAC ATGTGAGTCT | 3360 |
| CACTCTTTGA TTACTATCCG CCTGTCTCAT TGCTCTCTCT TTCATATTCT AATGACACTA | 3420 |
| AATTTAGGTT GAAGTTCCAT TAGAGTGCTG CTTAGACGCG ATACCTGAGG AGATGTATAG | 3480 |
| AAAAGCTT | 3488 |

(2) INFORMATION FOR SEQ ID NO:13:

(i) SEQUENCE CHARACTERISTICS:
        (A) LENGTH: 1328 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:13:

| | |
|---|---|
| GAATTCCGTG AGCCCTGTAC GGCAATGGCA ACCCCAGGGT TACTGGGGTG GCTGAATGGT | 60 |
| CTCGGCTTAC GCAATTGTTT GTGGCAGCTG CGTGGGCTAA ATGTAGGTTG TCTCTTGTTG | 120 |
| CACTGCAGGA TGGATGGGTA GCCTCTGGGC CGCCTCTGCT AGTGTCTAGC GTTGCTGACT | 180 |

```
GTGGTTTATT CAGGGATGCC CATGCCCATG CTAGATTGAT AGGTCATAGG TGCCATTCTA      240

ATGGTAGGTG GCGGTAAGGT TTATTAAGCT GTCGTATCAG TAGGTAACCT CATGAATCAG      300

GGTTTAAGCC CACCTTCTCC TTTGTGTGGG TGCATAAGGA ATGCACTTGG CTTCGTTCCC      360

TGCTAGTCTT TGCTCATGTG TCATTCTACC AAGTGGGTTA CTGTAACATT GCACTCTATG      420

ATGGTTGGTG GTTGTGCATC TTTTTGCTTC CCCTGGTTGT CTAATACCTG CATGTAACTG      480

ATGACCTTCT TTTATGTATC ATATAGATTA CATCTTTTGT TGTACATCTC AATTCTGAAA      540

AACAATGTTT TGCATTCTTA GCGCTCTGTG CACAAGGAAA AGGAGGTTTT ACCTGCAACT      600

TTTTTTTTCG AGAAAAAACA AACCTTTCTG AAAGGCAGTG ATCATTTAGT ATAAAGAAAA      660

TTTGATTTAC TTTCTTCAGA GAGAATATTC CAAACAAACA ATTTTCTTAC AGTCTGAGCC      720

ACGAAATTTG ATCTTGATCT TACTTTCACA AGCCACATGA AGCCTTATCA TCGCTCTGAT      780

AAAAAAACCA AATAGGTGAT TCATAGAATG AGAAAAAGAA CCTGTTGCCA TTTGGGGACC      840

TTGTTGTGTA CTCATTATCC CCCTGCTCA GGTTGAGGTT TCCTTGCCAC TGCCACCCCT      900

TGGCCCCTTC TTATACAACC ATCTCCATTG AAAAAGATTT TGCACTACAT TTGGGCTTCG      960

TATAACAAAA AAGGAAAATA AAACTAAACA GCAGAAACAT AGTATAATTA TAGGTAAAAG     1020

GTTNTGGCAA GTTTGAGTGG TAGAGACCTT TGTATATTTG GACATATTTC ACTAGTAAAT     1080

AGTTTTCTAA AATGTTCATG AATGGTGGCC AATAAACTTG ATAAGATCTC AACATGGCAG     1140

GTTCCTTCAA AATGAGAGGA AAACTGGAAA CATCACAAAT ATTTTTTAGC GAGTGGCCTA     1200

TAAATTATAA TGTTGCTTTC ATTTCTTTGA TATTCAAAAC TTCCTAAGAG TATTCTGCTA     1260

GAGCTCTGAT GGTGTCTTTT GCCTCTGTCA GATTTTCCAG GAGTTTTCTT CCCTTTTTAT     1320

GGCACTGT                                                              1328

(2) INFORMATION FOR SEQ ID NO:14:

(i) SEQUENCE CHARACTERISTICS:
        (A) LENGTH: 1565 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:14:

AGCATCCCTT GGGATTGTGA TNACTCACAT AAATTCTTGC GAANTGTTGA CATTCTAGTG       60

ATTTGAGTTC CGTTCTAGTG TGCTAGTCAN TTGAGCTCAA GTCTTGGTTT TATGTGTGCG      120

TATTCACTGT GATCTTTGTG TCGTGTGTGA GTTGTTGATC CTTCCCTTGC TCCGTGATTC      180

TTTGTGAAAT CTTTTGAAAG GGCGAGAGGC TCCAAGCTGT GGAGATTCCT CGCAAGTGGG      240

ATTAAGAAAA GCAAAGCAAC ACCGTGGTAT TCAAGTTGGT CTTTGGACCG CTTGAGAGGG      300

GTTGATTGCA ACCCTCGTCC GTTGGGACGC ACAACGTGG AGTAGGCAAG CGTTGGTCTT      360

GGCCGAACCA CGGGATAACC ACCGTGCCAT CTCTGTGATT GATATCTCTT GGTTATTGTG      420

TTGTGTTGAG ATCCTTCTCT AGCCACTTGG CAAATTACTG TGCTAACAAT TAATCAAGTT      480

TTGTGGCTTA AGATTTTGAA GTATTACAGG ATCTGCATCA TGGTCTGTGT CTCCACAGCT      540
```

-continued

```
ATGACACCCA CAGGAATTCA TGTGTTCCTT GGAGCCACTC TTGGATGACC TAAAGGAATT      600

ATTTCTAACC GGCTTGTACA CATATGATGC ATCAAGAGAT GAGTGTTTTA CTATGCGAGG      660

GGCCATGCTT ATGACCATAA GTAATCTTCC TGGTTTAGAA ATGCTTGCTT CTCATATGGT      720

TCATGGAAAA TTCGCATGCC TCCTTGTGGT GAAAATGTCT GGACAAAACA GCTGAAGAAT      780

GGTCGTAAAT CTTGTTTTAT GGAAATCGC CAATATATTG ATCTTGATCA TTCTTATTGC       840

TTGGATGCAG ACTCCGTTTG ATGGAACGAT AGACTTCGAA CAAAACCTAA AACCTATTAT      900

GATCGTCCAA TTTTGGATGA AATCATCACA CTTGGTGATT TCAAGAACTC AAAAAYTTAC      960

AGTTAATTGG ATATAGGAGG GNGCAAAAAC ACAGTAAGTT GGACATTCCA TAAGGGGATT     1020

TATTTTAGTT GACAATAAAG TAGATGGGCA TCATCCTGAG TTTNGTTTGG CATCGTGTCG     1080

TAGATTGAAA CTGTAAGGAT GGACATGGTA GNTAACAGGT TGAGATGAAT GATTCAACAG     1140

TTGAAGCGAA TGTACAATCT TTATGTGATG GTGGCTNTTA ATGCAGGTAA CTAGTTTTTT    1200

TTTATGCTTT ATTATTAATT AGTTGGATAA ATGGTTTNGA TTTNTGATTG TTAAANTGCA     1260

ATGGCTCCAG TTGGATGGNA ACAGCCANGT AATTTATGCA GAAGNAGNAG NTGGTGGTAC     1320

ACGGNTTCAG ATTGATGGAA AGANATGTTT ATTGCAGGTA AATANTCCCT TNTTCCTTTA     1380

TATTTTTGTT GTNTGATTGT ATAANTTTGN TAGATTATTT GTATAATTTA TTATTGCATT     1440

TCACCCCACT AANTTATTTT TAAAAGATGG GTTTTGTTGT TTGNTTCAGC NGGCGACATC     1500

ACATAAGNAA ATTGTGATTA ATTTTTGTTT TTTTGCAGNA TGACCATGAT CCATCAAAGT     1560

TATTA                                                                 1565
```

(2) INFORMATION FOR SEQ ID NO:15:

(i) SEQUENCE CHARACTERISTICS:
        (A) LENGTH: 1168 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:15:

```
ACATAAGCTG GGTTAGTAGT GGTGAATTAG TGGATTATTG ATCTGTTGTG GGCAAGGAGN       60

TGGCTTGGTG TCGAGAAAAA ACATGGAAGT GTGTATTGCC AGTGCTTATT YTRGGGATAT      120

GAGGGAATTW AMATTACATT TGTGACTGGG CGGACTGTAG GATAGGAGTT ATCTTGYTCG      180

ATTGGTATAC GGTGCATACA GSKYTTGACC AGCTATTATT TTAACAGGGT TTTCTGCCCT      240

GAACAAGTCC TTGGGCGGGA AGTGTACAGC TCCCACATGC AGCTTGGTGG TCCTAAGATC      300

ATGGCGACCA ATGGTGTTGT CCACCTCACT GTTCCAGATG ACCTTGAAGG TGTTTCCAAT      360

ATATTGAGGT GGCTCAGCTA TGTTCCTGCA ACATTGGTG GACCTCTTCC TATTACCAAA       420

CCTCTGGACC CTCCAGACAG ACCTGTTGCT TACATCCCTG AGAACACATG CGATCCACGT     480

GCAGCTATCT GTGGTGTAGA TGACAGCCAA GGGAAATGGT TGGGTGGTAT GTTTGACAAA     540

GACAGCTTTG TGGAGACATT TGAAGGATGG GCAAAAACAG TGGTTACTGG CAGAGCAAAG     600

CTTGGAGGAA TTCCATGCAT CTTAATAAAC ACAGTTGGCC CTTAAAGCAA GTGAACTTCT     660
```

```
TGAACAAACC AAACTAAGTG AACTCCGTGC AAGCGTTGCA AGAAGCCTTT CGGATCTGGG      720

GATGCATAAG GGAGAAATGA GTATTAAGGA TAACATGGAA GATTTAGTCT CTGCCCCATT      780

ACCTGTTGAA GATGCTCTGA TTTCTTTGTT TGATTACAGT GATCGAACTG TTCAGCAGAA      840

AGTGATTGAG ACATACATAT CACGATTGTA CCAGGTATTA TATCAACTAA CTTAATGTCT      900

TCCATAGTCT CACTAAGCAT ATCTGATATG TTTAGATACC CTACATGGAA TGCTCATCTT      960

TTCATTTGAC ACAAAGAAAC ATTGAGAAAT GAGATGCTGA CGATTGGCTG AAATTAACTG     1020

GGTNTGAGAA ATTGTGATCT CCCAACTTGT TAATGCACAA TGTTCTGGCT AACTTGCCAA     1080

TATTTTTTCA GCCTCATCTT GTTNAGGATA GCANCCAAAT GAAATCCAAG GATCTGGTGC     1140

TATTACTTTT TGGGAATTTA TGAAGGGC                                        1168
```

(2) INFORMATION FOR SEQ ID NO:16:

(i) SEQUENCE CHARACTERISTICS:
        (A) LENGTH: 638 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:16:

```
CTCCCAATAT TGTCATGAGG CTTGCATCCC AGGTTAGTTT TTTTTCCTTT CTGAAATTTA       60

TATTCCATAC CTTTTCACCT TTAGTTATCC TTGTATTTTC TGGAAGCTTC ATCTGATGCA      120

TTATTGACAA ATGCACTAAT GGTCATCATA TTTGGAGATT AACATATTTA TCTTAATTGA      180

TGGGAACTCT TGAAAATGAC AATGGTTGAG CAGATAATTA ACAGTTTTTT AATAAAAAAA      240

CATGCATTTC TAGGAGTTGG ACTAAGCTTT TCTTAGTATG AAGTGCCATG TTTTACATGG      300

TCCATTTGTG TCAATTTACA GTCGGTATCA TGGAAAGGTT GTCATAATGG CTGGAGANAA      360

ACAACACATC TTGTTTCTCA ACACTTGTGG GAGAAGANGT TTTACCTTTT TTCCTAAAAT      420

TACTTTTTGT ACTAAATTGT ATAATTTTTC CAATATTCTC CATGATTATT GAACTCTGCT      480

GTGTTCAAAC AGCCAAAACA TGTTTCCATA CTTTACACCT TTATTTTTTA GATGGAACCT      540

GGAATTGTGC TCTGTTATCT GTATCATGCA TATATTGATC TTAAACCTAT CTCTATTGTA      600

GAATCCGCAC TTGAATTCAG TTGCTTGTGA TCAATATG                              638
```

(2) INFORMATION FOR SEQ ID NO:17:

(i) SEQUENCE CHARACTERISTICS:
        (A) LENGTH: 558 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:17:

```
GGTAACCACC ACACCCGCGG CGCTTAATGG CCGTACAGGG NGGTCCCATT CGCCATTCAG     60
GTGCGCAACT GTTGGGAAGG GCGATCGGTG CGGGCTTCTT CGNTATTACG CCAGCTGGCG    120
AAAGGGGGAT GTGCTGCAAG GCGATTAAGT TGGGTAACGC CAGGGTTTTC CCAGTCACGA    180
CGTTGTAAAA CGACGGCCAG TGAGCGCGCG TAATACGACT CACTATAGGG CGAATTGGGT    240
ACCGGGCCCC CCCTCGAGGT CGACCTGCAG GTCAACGGAT CCTAGGGGGC CAACAGATTC    300
TTATCAAATG AATGGGATTA TCAATGAAAC ACATAATGGA AGACATGCCT CAGTGTCCAA    360
GGTTGTTGAA TTTTGTGCGG CACTAGGTGG CAAAACACCA ATTCACAGTA TATTAGTGGC    420
CAACAATGGA ATGGCAGCAG CAAAATTTAT GAGGAGTGTC CGGACATGGG CTAATGATAC    480
TTTTGGATCT GAGAAGGCAA TTCAACTCAT AGCTATGGCA ACTCCGGAAG ACATGAGGTA    540
AATGCAGAAC ACATTAGA                                                 558
```

(2) INFORMATION FOR SEQ ID NO:18:

(i) SEQUENCE CHARACTERISTICS:
        (A) LENGTH: 975 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:18:

```
GAATAATCTG CCTGCAGCTC AAGTTGCTGT TGGAATGGGC ATACCTCTTT GGCAGATTCC     60
AGGTAATTAC CAATTTACCA ACTTATTTAG TTCCTTATTG TTTTATTCTC TAATTTTCTA    120
CTTATGTAGA AATCAGACGT TTCTATGGAA TGGACTATGG AGGAGGGTAT GACATTTGGA    180
GGAAAACAGC AGCTCTTGCT ACACCATTTA ATTTTGATGA AGTAGATTCT CAATGGCCAA    240
AGGGCCATTG TGTAGCAGTT AGAATTACTA GTGAGGACCC AGATGATGGT TTCAAACCTA    300
CTGGTGGGAA AGTGAAGGTA AGTTTTCTAG ATGACATGTA TTATATATCG TTCAAAGAGA    360
TTAAGTTTGG TTAAATGACT AGGTCTTGAT TTTTTATCTT TCAGGAGATA AGTTTTAAAA    420
GCAAGCCTAA TGTTTGGGCC TACTTCTCAG TAAAGGTAAC TTGTTAACTT TAGTACGCTG    480
TCACATTATT CTTCSTTGTG AAAATAATTT GAACGGTTCT CTTTGTATTT TAACCATCCA    540
TCGTCTCATT TASCAGAGCA CACAAATATT TGCACTGACC CCCCTCCCCT TATCTGCTTT    600
CAGTCTGGTG GAGGCATTCA TGAATTTGCT GATTCTCAGT TCGGTATGTG TAAACCAAGA    660
GTATTCTTTG TAATTTATAT TGGTCCTCAA TTTTGAAATA TTGCTCTTTC CGTTACAGGA    720
CAWGTTTTTG CATATGGGCT CTCTAGATCA GCAGCAATAA CAAACATGAC TCTTGCATTA    780
AAANAGATTC AAATTCGTGG AGAAATTCAT TCAAATGTTT GATTACACAG TTGATCTCTT    840
AAATGTTAAG AAATATTAAC CACCTTTTAA ATCACATTTT CCATTATGTT TGATTCCATA    900
TCATTAATTT TGATTTTCTA TTATGGCTAA ACCTGTGGTG CTATTTTCCT ATTATCCCAG    960
GCTTCCGACT TTAGA                                                    975
```

(2) INFORMATION FOR SEQ ID NO:19:

(i) SEQUENCE CHARACTERISTICS:
        (A) LENGTH: 852 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:19:

```
GGATCCTAGG GGGCCAACAG ATTCTTATCA AATGRAATGG GATTATCAAT GAAACACATA      60
ATGGAAGACA TGCCTCAGTG TCCAAGGTTG TTGAATTTTG TGCGGCACTA GGTGGCAAAA     120
CACCAATTCA CAGTATATTA GTGGCCAACA ATGGAATGGC AGCAGCAAAA TTTATGAGGA     180
GTGTCCGGAC ATGGGCTAAT GATACTTTTG GATCTGAGAA GGCAATTCAA CTCATAGCTA     240
TGCAACTCC GGAAGACATG AGGATAAATG CAGAACACAT TAGAATTGCT GACCAATTAC      300
GTAGARGTGC CTGGTGGAAC AAACAATAAT AACTACGCCA ATGTTCAACT CATAGTGGAA     360
GTTAGCCTTG CTAATCTGTT AGTTTACTAC TGGTCTGCTG TTTCCTTTAT TTGTTGTATA     420
ATGATTGACA TATTTAAGTA GAGAAATTTA TATTTCTCCT CTGCTGTTGT GGAAGTCCAA     480
TTGTCACCAT TAACTGTGAA ATATTGCAGA TGGCACAAAA ACTAGGTGTT TCTGCTGTTT     540
GGCCTGGTTG GGGTCATGCT TCTGAGAATC CTGAACTGCC AGATGCATTG ACCGCAAAAG     600
GGATCGTTTT TCTTGGCCCA CCTGCATCAT CAATGAATGC TTTGGGAGAT AAGGTCGGCT     660
CAGCTCTCAT TGCTCAAGCA GCCGGGGTCC CAACTCTTGC TTGGAGTGGA TCACATGTGA     720
GTCTCACTCT TTGATTACTA TCCGCCTGTC TCATTGCTCT CTCTTTCATA TTCTAATGAC     780
ACTAAATTTA GGTTGAAGTT CCATTAGAGT GCTGCTTAGA CGCGATACCT GAGGAGATGT     840
ATAGAAAAGC TT                                                         852
```

(2) INFORMATION FOR SEQ ID NO:20:

(i) SEQUENCE CHARACTERISTICS:
        (A) LENGTH: 231 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:20:

```
AATTCCTGTG GGTGTTATAG CTGTGGAGAC ACAGACCATG ATGCAGCTCA TCCCTGCTGA      60
TCCAGGTCAA CTTGATTCCC ATGAGCGATG TGTTCCTCGG GCTGGACAAG TGTGGTTCCC     120
AGATNCTGCA ACCAAGACAG CTCAGGCATT ATTAGACTTC AACCGTGAAG GATTGCCTCT     180
GTTCATCCTG GCTAACTGGA GAGGCTTCTC TGGGGACAG AGAGATCTCT T               231
```

(2) INFORMATION FOR SEQ ID NO:21:

(i) SEQUENCE CHARACTERISTICS:
        (A) LENGTH: 207 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:21:

```
AATTCATGCA TCTTAATAAA CACAGTTGGC CCTTAAAGCA AGTGAACTTC TTGAACAAAC      60

CAAACTAAGT GAACTCTGTT CCAGCATTGC AAGAAGCCTT TCAGATCTGG GGATGCATAA     120

GGGAGAAATG ACTATTAAGG ATAGCATGGA AGATTTAGTC TCTGNCCCAT TGCCTGTTGA     180

AGATGCTCTT ATTTCTTTGT TTGATTA                                         207
```

(2) INFORMATION FOR SEQ ID NO:22:

(i) SEQUENCE CHARACTERISTICS:
        (A) LENGTH: 180 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:22:

```
ATAGACCTGT CGCATACATC CCTGAGAACA CATGCGATCC GCGTGCAGCC ATCCGTGGNG      60

TAGATGACAG CCAAGGGAAA TGGTTGGGTG GTATGTTTGA CAAAGACAGC TTTGTGGAGA     120

CATTTGAAGG ATGGGCAAAA ACAGTGGTTA CTGGTAGAGC AAAGCTTGGA GGAAGGAATT     180
```

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:23:

```
ACTGTGCGTT TGAGAAGGTC                                                  20
```

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:24:

CCTCTACGTA ATTGGTCAGC                          20

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:25:

CCTTTTTATG GCACTGTGCG                          20

(2) INFORMATION FOR SEQ ID NO:26:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:26:

CATCGTAGCC TATATGAGGA CG                       22

TRANSGENIC PLANTS EXPRESSING MAIZE ACETYL CoA CARBOXYLASE GENE AND METHOD OF ALTERING OIL CONTENT

This application is a national stage filing of PCT/US96/04625, filed Apr. 4, 1996, which is a continuation-in-part of U.S. application Ser. No. 08/417,089, filed Apr. 5, 1995, now U.S. Pat. No. 6,069,298 which is a continuation-in-part of U.S. application Ser. No. 08/014,326, filed Feb. 5, 1993, now U.S. Pat. No. 5,498,544.

BACKGROUND OF THE INVENTION

Acetyl CoA carboxylase (ACCase) is an enzyme involved in many important metabolic pathways in plant, animal and bacterial cells. The enzyme is especially important in fatty acid synthesis in plants and is sensitive to inhibition by some types of herbicides. Structurally, ACCases are biotinylated and are quite large enzymes consisting of one or more subunits. For example, most ACCases of animals, higher plants, and yeast are dimers of 420 to 700 kD native MW and contain subunits of 200 to 280 kD. Diatom and algal ACCases are 700 to 740 kD tetramers of 160 to 180 kD subunits. Bacterial ACCase consists of three dissociable proteins, biotin carboxylase (51 kD), biotin carboxyl carrier protein (22.5 kD), and biotin transcarboxylase (130 kD).

Acetyl CoA Carboxylase (ACCase) catalyzes the formation of malonyl-CoA from acetyl-CoA and bicarbonate in animal, plant, and bacterial cells. Malonyl-CoA is an essential substrate for (i) de novo fatty acid (FA) synthesis, (ii) fatty acid elongation, (iii) synthesis of secondary metabolites such as flavonoids and anthocyanins, and (iv) malonylation of some amino acids and secondary metabolites. Synthesis of malonyl-CoA is the first committed step of flavonoid and fatty acid synthesis and current evidence suggests that ACCase catalyzes the rate-limiting step of fatty acid synthesis. Formation of malonyl-CoA by ACCase occurs via two partial reactions and requires a biotin prosthetic group:

(i) E-biotin+ATP+$HCO_3$→E-biotin-$CO_2$+ADP+Pi (ii) E-biotin-$CO_2$+Acetyl-CoA —>E-biotin+malonyl-CoA (NET)Acetyl-CoA+ATP+$HCO_2$→malonyl-CoA+ADP+Pi In *E. coli*, these reactions are catalyzed by three distinct components; biotin carboxylase, biotin transcarboxylase, and biotin carboxyl carrier protein, which can be separated and yet retain partial activity. Plant and animal ACCases contain all three activities on a single polypeptide.

In plants, most ACCase activity is located in plastids of green and non-green plant tissues including leaves and oil seeds. Leaf ACCase activity is primarily located in mesophyll cells, but lesser amounts have been found in C-4 bundle sheath cells and in epidermal cells. The subcellular location of ACCase activity in epidermal cells is unknown, but since synthesis of very long-chain fatty acids (VLCFA) for formation of waxes, cutin, and suberin occurs on the endoplasmic reticulum (ER), malonyl-CoA might also be derived from a cytosolic ACCase. In contrast, rat ACCase is primarily cytosolic or associated with the outer mitochondrial membrane.

De novo fatty acid synthesis in chloroplasts involves successive 2-carbon additions to acetate, using malonate as the 2-C donor. All intermediates are attached to acyl carrier protein (ACP). Synthesis in plastids resembles that in *E. coli* in that the fatty acid synthesis complex can be dissociated into separate enzymes: β-ketoacyl-ACP synthase (KAS), β-ketoacyl-ACP reductase, β-hydroxyl-ACP dehydratase, and enoyl-ACP reductase, acetyl-CoA:ACP transacylase, and malonyl-CoA:ACP transacylase. A highly active KASIII isozyme catalyzes the condensation of acetyl-CoA and malonyl-ACP. Successive additions of malonyl-CoA to acy-1-ACPs catalyzed by KAS I form C16 acyl-ACP, some of which is converted to C18 acyl-ACP by KAS II and then to C18:1-ACP. Fatty acid inetabolisni then diverges; de-esterification allows movement to the cytoplasm (eukaryootic path) where fatty acids may be further unsaturated and/or elongated by additions of malonyl-CoA in the ER. Alternatively, fatty acids are linked to glycerol-3-phosphate (prokaryotic path), further unsaturated, and used for synthesis of chloroplast lipids. A portion of cytoplasmic lipids returns to the chloroplast. The relative contributions of these two paths are species-specific but appear to be relatively flexible in mutants blocked in either path. In oil-storing organs such as cotyledons and monocot embryos the triacylglycerides are stored in cytoplasmic oil bodies surrounded by a single unit membrane.

Condensation of malonyl-CoA with phenylpropionyl-CoAs or acetyl-CoA leads to synthesis of flavonoids, anthocyanins, or to polyacetates. Condensation is increased by light, elicitors, or pathogens and may be the rate-limiting step in synthesis of some phytoalexins. In addition to the secondary metabolites derived by de novo synthesis, malonyl conjugates of flavonoid glycosides, formed by malonyl-CoA:flavonoid glycoside malonyltransferase, D-amino acids and 1-amino-carboxyl-cyclopropane (ethylene precursor) are found in plants. Malonylated compounds accumulate in vacuoles, probably after synthesis in the cytoplasm.

An important property of ACCase is the central role it plays in fatty acid synthesis and accumulation in plants and seeds. Available evidence supports the idea that ACCase activity is the rate-limiting step for de novo fatty acid synthesis in plants. High rates of ACCase activity in vitro parallel or slightly precede high rates of lipid deposition or [$^{14}$C] acetate incorporation into lipids in developing leaves and oil seeds. Significant changes in plant ACCase activity occur during chloroplast development and increase in ACCase activity correlates with lipid deposition in developing oil seeds. Turnham et al., *Biochem. J.* 212:223 (1883); and Beittenmiller et al., *Plant Physiol.,* 100:923 (1992).

Among other properties, ACCase in most monocots is also inhibited by several herbicides. [$^{14}$C]acetate incorporation into maize lipids is strongly inhibited by fluazifop and sethoxydim due to inhibition of plastid ACCase. In barley however, fluazifop had little effect on [$^{14}$C]acetate incorporation into very long-chain fatty acids. Since synthesis of very long-chain fatty acids occurs in the cytosol on the ER, and de novo fatty acid synthesis occurs in the plastids, cytosolic malonyl-CoA might be supplied by a herbicide insensitive ACCase isozyme.

There are three general mechanisms by which plants may be resistant to, or tolerant of, herbicides. These mechanisms include insensitivity at the site of action of the herbicide (usually an enzyme), rapid metabolism (conjugation or degradation) of the herbicide, or poor uptake and translocation of the herbicide. Altering the herbicide site of action from a sensitive to an insensitive form is the preferred method of conferring tolerance on a sensitive plant species. This is because tolerance of this nature is likely to be a dominant trait encoded by a single gene, and is likely to encompass whole families of compounds that share a single site of action, not just individual chemicals.

Therefore, detailed information concerning the biochemical site and mechanism of herbicide action is of great importance and can be applied in two ways. First, the information can be used to develop cell selection strategies for the efficient identification and isolation of appropriate herbicide-tolerant variants. Second, it can be used to characterize the variant cell lines and regenerated plants that result from the selections.

Tissue culture methods have been used to select for resistance (or tolerance) using a variety of herbicides and plant species (see review by Meredith and Carlson, 1982, in *Herbicide Resistance in Plants*, eds. Lebaron and Gressel, pp. 275–291, John Wiley and Sons, NY). For example, P. C. Anderson et al., in U.S. Pat. No. 4,761,373, disclose the use of tissue culture methods to produce maize plants resistant to herbicidal imidazolidones and sulfonamides.

The resistance is due to the presence of altered acetohydroxy acid synthase which is resistant to deactivation by these herbicides.

Certain 1,3-cyclohexanediones exhibit general and selective herbicidal activity against plants. One such cyclohexanedione is sethoxydim {2-[1-(ethoxyimino)-butyl]-5-[2-(ethylthio)propyl]-3-hydroxy-2-cyclohexen-1-one}. Sethoxydim is commercially available from BASF (Parsippany, N.J.) under the designation POAST™.

Other herbicidal cyclohexanediones include clethodim, (E,E)-(±)-2-[1-[[(3-chloro-2-propenyl)oxy]imino]propyl]-5-[2-(ethylthio)propyl]-3-hydroxy-2-cyclohexen-1-one; available as SELECT™ from Chevron Chemical (Valent) (Fresno, Calif.); cloproxydim, (E,E)-2-[1-[[(3-chloro-2-propenyl)oxy]imino]butyl]-5-[2-(ethylthio)propyl]-3-hydroxy-2-cyclohexen-1-one: available as SELECTONE™ from Chevron Chemical (Valent) (Fresno, Calif.); and tralkoxydim, 2-[1-(ethoxyimino)propyl]-3-hydroxy-5-mesitylcyclohex-2-enone, available as GRASP™ from Dow Chemical USA (Midland. Mich.).

For purposes of reference in the present specification, the herbicides described in the two preceding paragraphs and other structurally related herbicidal compounds, are collectively referred to as the cyclohexanedione family of herbicides.

Certain aryloxyphenoxypropanoic acids exhibit general and selective herbicidal activity against plants. In these compounds, the aryloxy group may be phenoxy, pyridinyloxy or quinoxalinyl. One such herbicidal aryloxyphenoxypropanoic acid is haloxyfop, {2-[4-[[3-chloro-5-(trifluoromethyl)-2-pyridinyl]oxy]phenoxy]-propanoic acid}, which is available as VERDICT™ from Dow Chemical USA (Midland, Mich.). Another is diclofop, {(±)-2-[4-(2,4-dichlorophenoxy)-phenoxy]propanoic acid}, available as HOELON™ from Hoechst-Roussel Agri-Vet Company (Somerville. N.J).

Other members of this family of herbicides include fenoxyaprop, (±)-2-[4-[(6-chloro-2-benzoxazolyl)oxy] phenoxy]propanoic acid; available as WHIP™ from Hoechst-Roussel Agri-Vet Company (Somerville, N.J.); fluazifop, (±)-2-[4-[[5-(trifluoromethyl)-2-pyridinyl]oxy] phenoxy]propanoic acid; available as FUSILADE™ from ICI Americas (Wilmington. Del.); fluazifop-P, (R)-2-[4-[[5-(trifluoromethyl)-2-pyridinyl]oxy]phenoxy]propanoic acid; available as FUSILADE 2000™ from ICI Americas (Wilmington. Del.): and quizalofop, (±)-2-[4[(6-chloro-2-quinoxalinyl)oxy]phenoxy]propanoic acid; available as ASSURE™ from E. I. DuPont de Nemours (Wilmington, Del.).

For purposes of reference in the present specification, the herbicides referred to in the two preceding paragraphs and other structurally related herbicidal compounds, are collectively referred to as herbicidal aryloxyphenoxypropanoic acids.

Thus, there is a need for methods to develop plants that are resistant or tolerant to herbicides. There is also a need to increase the oil and/or fatty acid content of the plants and seeds, as well as for methods to increase their resistance to herbicides. Moreover, there is a need to identify and clone genes important in conferring herbicide tolerance and in increasing the oil content of plants.

SUMMARY OF THE INVENTION

The present invention provides an isolated and purified DNA molecule comprising a DNA segment encoding a maize acetyl CoA carboxylase gene and methods for conferring herbicide tolerance and/or altering the oil content of plants by introducing and expressing a plant acetyl CoA carboxylase gene in the plant cells. The DNA molecule encoding a plant acetyl CoA carboxylase can encode an unaltered plant acetyl CoA carboxylase or an altered plant acetyl CoA carboxylase substantially tolerant to inhibition by cyclohexanedione or aryloxyphenoxypropanoic acid herbicides as well as encoding an antisense DNA sequence that is substantially complementary to a plant acetyl CoA carboxylase gene or to a portion thereof. A DNA molecule of the invention can also further comprise an amino terminal plant chloroplast transit peptide sequence operably linked to the maize acetyl CoA carboxylase gene.

The method of imparting cyclohexanedione or aryloxyphenoxypropanoic acid herbicide tolerance to a plant includes the steps of introducing a chimeric DNA molecule comprising a gene coding for a plant acetyl CoA carboxylase or an altered or a functional mutant thereof operably linked to a promoter functional in a plant cell into cells of a susceptible plant, and regenerating the transformed plant cells to provide a differentiated plant. The promoter can be an inducible or tissue specific promoter or provide for overexpression of at least about a 2-fold amount of a native plant acetyl CoA carboxylase. The functional linkage of a promoter to the chimeric DNA molecule results in an expression cassette. Expression of the chimeric DNA molecule is in an amount effective to render the acetyl CoA carboxylase and/or the plant tissue substantially tolerant to the herbicides relative to the native acetyl CoA carboxylase present in said plant. Herbicide tolerance can be achieved in the plants by at least two methods, including increasing the level of gene expression of a native or unaltered acetyl CoA carboxylase, or by introducing an altered gene coding for an acetyl CoA carboxylase that is less sensitive to herbicide inhibition. The level of gene expression can be increased by either combining a plant acetyl CoA carboxylase gene with a promoter that provides for a high level of gene expression, such as a 35S cauliflower mosaic virus promoter (CaMV), or by introducing multiple copies of the gene into the cell so that the multiple copies of the gene are integrated into the genome of transformed plant cells. The preferred plant cells into which to introduce the expression cassette of the invention, to achieve herbicide tolerance, are monocot plant cells. Once transformed cells exhibiting herbicide tolerance are obtained, transgenic plants and seeds can then be regenerated therefrom, and evaluated for stability of the inheritance of the herbicide tolerance trait.

The invention also provides a method for altering, preferably raising, the oil content in a plant. The method includes the steps of introducing a chimeric DNA molecule comprising a gene coding for a plant acetyl CoA carboxylase or an altered or a functional mutant thereof operably linked to a promoter functional in a plant cell into the cells of plant tissue and expressing the gene in an amount effective to alter the oil content of the plant cell. An alteration in oil content can include a change in total oil content over that normally present in that type of plant cell or a change in the type of oil present in the cell. An alteration in oil content in the plant cell, according to the method of the invention can be achieved by at least two methods including:

(1) an increase or decrease in expression of an altered plant acetyl CoA carboxylase gene; or (2) by introducing an altered or functional mutant plant acetyl CoA carboxylase gene.

The level of gene expression of an unaltered plant acetyl CoA carboxylase gene can be increased by either combining an unaltered plant acetyl CoA carboxylase with a promoter that provides for a high level of gene expression, or by introducing multiple copies of an expression cassette into cells so that multiple copies of the gene are integrated into the genome. When an altered or a functional mutant plant acetyl CoA carboxylase gene codes for an enzyme that exhibits an increase in specific activity, it can lead to an increase in total oil content of the plant cell. When an altered or a functional mutant acetyl CoA carboxylase gene codes for an enzyme having a decrease in specific activity, it may lead to a decrease in the total oil content of the plant cell. Preferably, the expression cassette is introduced into dicot plants such as soybeans, canola, and sunflower. In an especially preferred version, transformed cells exhibiting about a 1.2- to 5-fold increase in total oil content and/or expression or specific activity of acetyl CoA carboxylase are selected for and used to generate transgenic plants and seeds exhibiting a substantial increase in oil content. A substantial increase in oil content depends on the oil content normally present in the plant or seed and can range from about a 1.2 to a 20-fold increase.

The invention also provides for a method of producing plant acetyl CoA carboxylase in a host cell. The method includes the steps of introducing an expression cassette comprising a chimeric gene encoding a plant acetyl CoA carboxylase or an altered or a functional plant acetyl CoA carboxylase operably linked to a promoter into a host cell and expressing the gene in an amount sufficient to permit crystallization of the plant acetyl CoA carboxylase. An expression cassette can include a promoter that is functional in either a eukaryotic or a prokaryotic cell. Preferably, the expression cassette is introduced into a prokaryotic cell, such as E. coli, that is routinely used for production of recombinantly produced proteins. Recombinantly produced and crystallized plant acetyl CoA carboxylase can then be used to identify other herbicides and that bind to and inhibit acetyl CoA carboxylase in plants. In addition, the availability of large amounts of purified enzyme can permit the screening of the efficacy of such herbicides in terms of their ability to bind to, or otherwise inhibit, the activity of the enzyme.

The present invention also provides an isolated and purified DNA molecule of at least seven nucleotide bases which hybridizes under high stringency conditions to a DNA molecule comprising) a DNA segment encoding a plant acetyl CoA carboxylase and provides a hybridization probe comprising an isolated and purified DNA molecule of at least seven nucleotide bases, which is detectably labeled or which binds to a detectable label, which DNA molecule hybridizes under high stringency conditions to the non-coding strand of a DNA molecule comprising a DNA segment encoding a plant acetyl CoA carboxylase.

High stringency conditions are defined as: hybridization at 65° C. for at least 16 hours in 5×SSC, 1×Denhardt's solution, 50 mM Tris-HCl, pH 8, 0.2% SDS, 10 mM EDTA, 0.1 mg/ml salmon sperm DNA, followed by washing twice for 5 minutes in 2×SSC, 0.5% SDS at 25° C., once for 10 minutes in 0.2×SSC, 0.1% SDS at 25° C. and twice for 30 minutes in 0.2×SSC, 0.1% SDS at 65° C.

The present invention also provides a method of introducing an exogenous plant acetyl CoA carboxylase gene into a host cell comprising transforming host cells in vitro with an expression cassette comprising a chimeric DNA molecule encoding a plant acetyl CoA carboxylase gene operably linked to a promoter functional in the host cell, expanding the transformed host cells in vitro, and identifying a transformed host cell which expresses the chimeric DNA molecule.

The term "consists essentially of" as used with respect to the present DNA molecules is defined to mean that a major portion of the nucleotide sequence encodes an ACCase, and that nucleotide sequences are not present which encode proteins other than ACCase or functional equivalents thereof.

BRIEF DESCRIPTION OF THE FIGURES

FIGS. 10A–10B: DNA sequence (SEQ ID NO. I) of a 2 kb EcoRI fragment of lambda clone #15-14 including a portion of a maize ACCase gene located at bases 2883 to 83 from the 3' stop codon.

FIGS. 13A–13E: DNA sequence (SEQ ID NO:5) of a 7470 base pair cDNA of a maize ACCase gene. (Genbank Accession No. U19183).

FIGS. 14A–14B: Predicted amino acid sequence of the complete ACCase gene of maize (SEQ ID NO:6).

FIGS. 16A–16B: Partial nucleotide sequence of a Type A1 ACCase genomic clone (SEQ ID NO:12).

FIG. 17: Partial nucleotide sequence of clone 5A, a Type A ACCase genomic clone (SEQ ID NO:13).

FIGS. 18A–18F: Partial nucleotide sequence of six Type A, ACCase genomic clones (SEQ ID NOs 14,15, 16. 17, 18. and 19).

FIGS. 19A–19C: Partial nucleotide sequence of three Type B ACCase clones (SEQ ID NOs 20, 21 and 22).

DETAILED DESCRIPTION OF THE INVENTION

Figure 1:
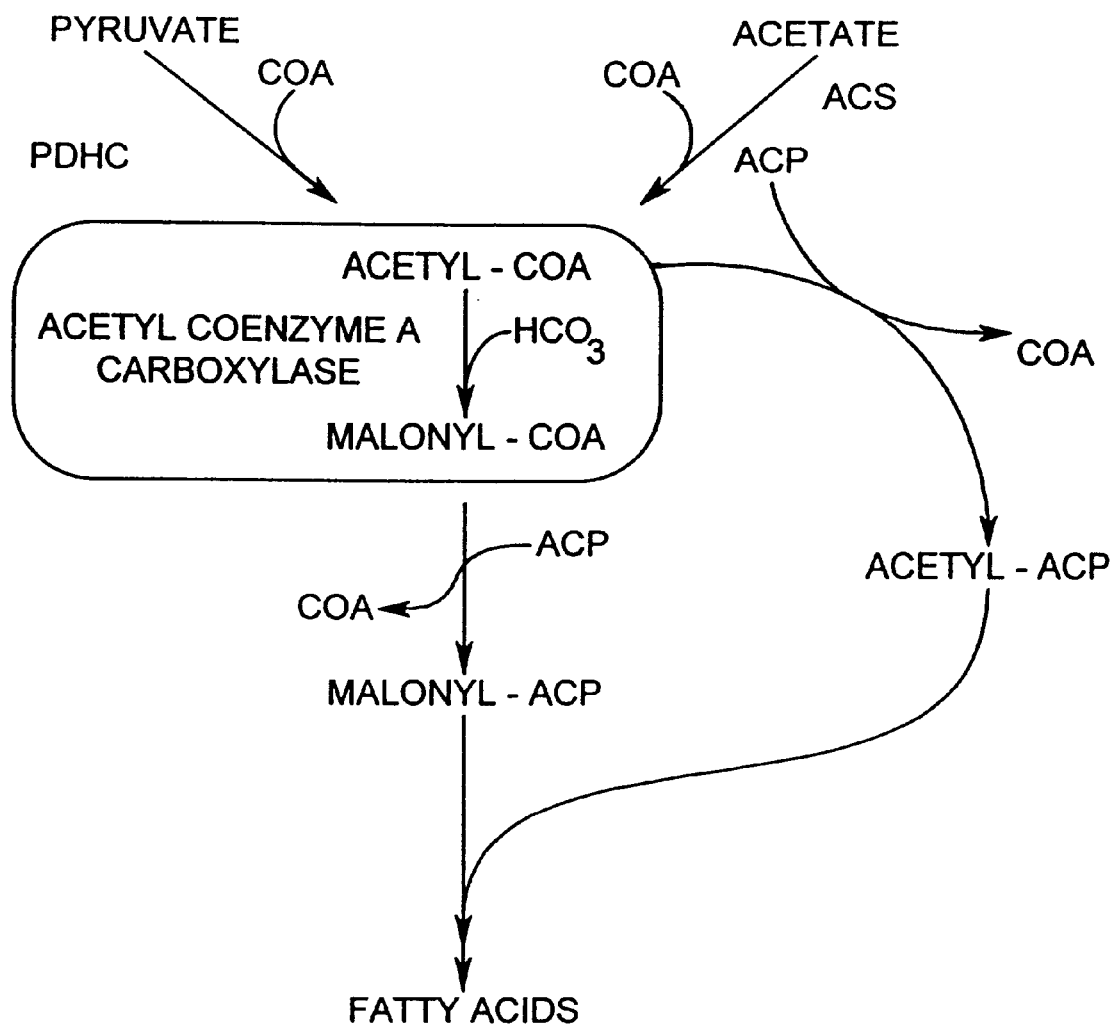
FIG. 1 is a schematic depiction of the fatty acid biosynthesis pathway in plants.

The present invention provides a DNA molecule encoding a plant acetyl CoA carboxylase gene and methods for conferring herbicide tolerance and/or altering the oil content of plants by introducing and expressing a plant acetyl CoA carboxylase gene in the plant cells. In plants, acetyl CoA carboxylase plays a central role in regulating fatty acid synthesis and in the sensitivity of monocots to cyclohexanedione or aryloxyphenoxypropanoic acid herbicides.

In accord with the present invention, a plant acetyl CoA carboxylase gene is identified, isolated and combined with a promoter functional in a plant cell to provide a recombinant expression cassette. A plant acetyl CoA carboxylase gene can be introduced and expressed in a plant cell. Depending on the type of plant cell, the level of gene expression, and the activity of the enzyme encoded by the gene, introduction of a plant acetyl CoA carboxylase gene into the plant cell can confer herbicide tolerance and/or alteration of the oil of the plant cell.

In monocots, an exogenously introduced plant acetyl CoA carboxylase gene can be expressed at a level effective to render the cells of the plant tissue substantially tolerant to cyclohexanedione or aryloxyphenoxypropanoic acid herbicide levels which normally inhibit a native or endogenous acetyl CoA carboxylase. A native acetyl CoA carboxylase i-i an enzyme that is normally encoded and expressed in the plant cell prior to transformation. An exogenously introduced plant acetyl CoA carboxylase gene is a gene which has been isolated and amplified from either the same or different type of cell. Exogenous introduction and expression of a plant acetyl CoA carboxylase gene in both monocots and dicots can result in alteration of the oil content and quality of plant tissue and seeds. Exogenous introduction and expression in a host cell, such as a bacteria, can provide for sufficient amounts of plant acetyl CoA carboxylase to allow for crystallization and isolation of the enzyme. Crystallized plant acetyl CoA carboxylase is useful to identify other herbicides that bind to and can inhibit plant acetyl CoA carboxylases. The enzyme could also be used to screen potential herbicidal compounds for efficacy.

A. Formation of an Expression Cassette

An expression cassette of the invention can comprise a chimeric DNA molecule encoding a plant acetyl CoA carboxylase gene or an altered or functional mutant thereof operably linked to a promoter functional in a plant cell. The gene can code for a plant acetyl CoA carboxylase that is substantially tolerant to herbicides, preferably cyclohexanedione and/or aryloxyphenoxypropanoic acid herbicides. An expression cassette of the invention can also include an antisense DNA sequence that is substantially complementary to an acetyl CoA carboxylase gene or a portion thereof operably linked to a promoter functional in a plant cell.

1. Isolation and Identification of a Gene Coding for a Plant Acetyl CoA Carboxylase A gene encoding a plant acetyl CoA carboxylase can be identified and isolated by standard methods, as described by Sambrook et al., *Guide to Molecular Cloning: A Laboratory Manual*, Cold Spring Harbor, N.Y. (1989). The gene can be obtained either from monocot or dicot plant cells. When the gene encoding a plant acetyl CoA carboxylase is obtained from a dicot plant, the enzyme encoded by the gene exhibits tolerance to cyclohexanedione or aryloxyphenoxypropanoic acid herbicides. The gene can also be obtained from herbicide-tolerant maize cell lines, prepared as described in U.S. Pat. No. 5,162,602.

A gene encoding a plant acetyl CoA carboxylase can be identified by screening of a DNA or cDNA library generated from plant cells. Screening for DNA fragments that encode all or a portion of the gene encoding a plant acetyl CoA carboxylase can be accomplished by complementation of an auxotrophic mutant of acetyl CoA carboxylase in *E. coli* (fabE) (Bachman, *Microbiological Reviews*, 47:180 (1983)) or veast (acc1) (Michionada, *Eur. J. Biochem.*, 111:79 (1980)) or by screening of plaques for binding to antibodies that specifically recognize a plant acetyl CoA carboxylase. DNA fragments that can restore ACCase activity in *E. coli* or yeast and/or plaques carrying DNA fragments that are immunoreactive with antibodies to a plant ACCase can be subcloned into a vector and sequenced and/or used as probes to identify other cDNA or genomic sequences encoding all or a portion of a plant acetyl CoA carboxylase gene.

Specific examples of cDNA sequences encoding a portion of a plant acetyl CoA carboxylase gene include DNA fragments that include a DNA sequence that substantially corresponds to the coding sequence for the transcarboxylase active site of a plant acetyl CoA carboxylase, DNA fragments that include a DNA sequence that substantially corresponds to a coding sequence for the biotin binding site of a plant acetyl CoA carboxylase, a DNA fragment encoding the 5' transcriptional start sequence of a plant acetyl CoA carboxylase gene, and a DNA fragment encoding the 3' transcriptional stop sequence for the acetyl CoA carboxylase gene. Substantially corresponding DNA sequences share about 90% to about 100% DNA sequence homology. Especially preferred cDNA probes can be obtained from lambda clone #18-5 which include DNA sequences corresponding to the transcarboxylase active site domain and the biotin binding site domain. Lambda clone #18-5 includes EcoRI subclones of 3.9 kb, 1.2 kb, or 0.23 kb. Lambda subclone #18-5I is an 3.9 kb EcoRI subclone. The lambda subclone #18-5I has been deposited with the American Type Culture Collection, Rockville, Md., and given Accession No. 69236.

In a preferred version, a plant acetyl CoA carboxylase gene is identified and isolated from an herbicide tolerant maize cell line prepared as described in Example II. A cDNA library can be prepared by oligo dT priming. Plaques containing DNA fragments can be screened with antibodies specific for maize acetyl CoA carboxylase. DNA fragments encoding a portion of an acetyl CoA carboxylase gene can be subcloned and sequenced and used as probes to identify a genomic acetyl CoA carboxylase gene. DNA fragments encoding a portion of a maize acetyl CoA carboxylase can be verified by, determining sequence homology with other known acetyl CoA carboxylases, such as chicken or yeast acetyl CoA carboxylase, or by hybridization to acetyl CoA carboxylase specific messenger RNA. Once DNA fragments encoding portions of the 5', middle and 3' ends as well as the transcarboxylase active site or biotin binding site of a plant acetyl CoA carboxylase are obtained, they can be used to identify and clone a complete genomic copy of a maize acetyl CoA carboxylase gene.

To isolate a complete copy of a maize acetyl CoA carboxylase gene, a maize genomic library can then be probed with cDNA probes prepared as described above. Portions of the genomic copy or copies of a plant acetyl CoA carboxylase gene can be sequenced and the 5' end of the gene are identified by standard methods including either DNA sequence homology to other acetyl CoA carboxylase genes or by RNAase protection analysis, as described by Sambrook et al., Molecular Cloning: A Laboratory Manual, Cold Spring Harbor Press, Cold Spring Harbor, N.Y. (1989). Once portions of the 5' end of the gene are identified, complete copies of a plant acetyl CoA carboxylase gene can be obtained by standard methods, including by cloning or by polymerase chain reaction (PCR) synthesis using oligonucleotide primers complementary to the DNA sequence at the 5' end of the gene. The presence of an isolated full-length copy of a plant acetyl CoA carboxylase gene can be verified by hybridization, partial sequence analysis, or by expression of a plant acetyl CoA carboxylase enzyme. The maize acetyl CoA carboxylase gene cloned and expressed from a maize herbicide tolerant cell line can be assessed for tolerance to cyclohexanedione or aryloxyphenoxypropanoic acid herbicides by standard methods, as described in Example I.

An expression cassette of the invention can also contain an antisense DNA sequence. A antisense DNA sequence is a sequence that is substantially complementary to all or a portion of a coding sequence of a plant acetyl CoA carboxylase gene. A substantially complementary sequence has about 90% to about 100% DNA sequence homology with that of the coding sequence of all or a portion of a plant acetyl CoA carboxylase. The antisense DNA sequence when expressed can act to inhibit the synthesis and expression of a native plant acetyl CoA carboxylase. Antisense sequences are preferably about 200 to 1000 nucleotides long in order to provide sufficient inhibition of synthesis and/or expression of a native acetyl CoA carboxylase. The inhibition of acetyl CoA carboxylase synthesis and gene expression by antisense DNA sequences can be confirmed in a transformed plant cell by standard methods for measuring the presence and/or activity of the enzyme such as described in Examples I and V.

An expression cassette of the invention can also include a functional mutant of a plant acetyl CoA carboxylase gene. Mutants of a plant acetyl CoA carboxylase gene are substantially homologous to a plant acetyl CoA carboxylase gene and are functional if the acetyl CoA carboxylase expressed retains significant enzyme activity. A mutant substantially homologous to a plant acetyl CoA carboxylase can share about 90% to 99.99% DNA sequence with that gene. For example, a mutant acetyl CoA carboxylase gene can code for a herbicide tolerant acetyl CoA carboxylase, or for an acetyl CoA carboxylase with altered substrate specificity so that the total amount of oil content in the plants or seeds is increased, or for an enzyme with an altered substrate specificity so that synthesis of secondary metabolites such as flavonoids or anthocyanins is decreased. A preferred mutant is a gene coding for an acetyl CoA carboxylase that is substantially tolerant to cyclohexanedione or aryloxyphenoxypropanoic acid herbicide.

Altered or functional mutants of a gene coding for a plant acetyl CoA carboxylase can be obtained by several methods. The alteration or mutation of the ACCase gene can be accomplished by a variety of means including, but not limited to, the following methods.

1. spontaneous variation and direct mutant selection in cultures;
2. direct or indirect mutagenesis procedures on tissue culture of all cell types, seeds or plants; and
3. mutation of the cloned acetyl CoA carboxylase gene by methods such as site specific mutagenesis (Sambrook et al., cited supra), transposon mediated mutagenesis (Berg et al., *Biotechnology*, 1:417 (1983)) and deletion mutagenesis (Mitra et al., *Molec. Gen. Genetic.*, 215:294 (1989)).

Mutants can be identified by a change in a functional activity of the enzyme. encoded by the gene or by detecting a change in the DNA sequence using restriction enzyme mapping or partial sequence analysis.

In a preferred version, a functional mutant gene encoding for a plant acetyl CoA carboxylase tolerant to cyclohexanedione and/or aryloxyphenoxypropanoic acid herbicides is isolated from a maize herbicide tolerant cell line. The maize herbicide tolerant cell line was obtained as described in U.S. Pat. No. 5,162,602, issued Nov. 10, 1992, the disclosure of which is incorporated in Examples I–III. Briefly, partially differentiated cell cultures are grown and subcultured with continuous exposures to low herbicide levels. Herbicide concentrations are then gradually increased over several subculture intervals. Maize cells or tissues growing in the presence of normally toxic herbicide levels are repeatedly subcultured in the presence of the herbicide and characterized. Stability of the herbicide tolerance trait of the cultured cells may be evaluated by growing the selected cell lines in the absence of herbicides for various periods of time and then analyzing growth after exposing the tissue to herbicide.

Maize cell lines which are tolerant by virtue of having an altered acetyl CoA carboxylase enzyme can be selected by identifying cell lines having enzyme activity in the presence of normally toxic levels of sethoxydim or haloxyfop. The tolerant maize cells can be further evaluated for whether acetyl CoA carboxylase is altered to a less sensitive form or increased in its level of expression.

Maize cell lines with a acetyl CoA carboxylase less sensitive to herbicide inhibition can be used to isolate a functional mutant gene of a plant acetyl CoA carboxylase. A DNA library from a maize cell line tolerant to herbicides can be generated and DNA fragments encoding all or a portion of an acetyl CoA carboxylase gene can be identified by hybridization to a cDNA probe encoding a portion of the maize ACCase gene. A complete copy of the altered gene can be obtained either by cloning and ligation or by PCR synthesis using appropriate primers. The isolation of the altered gene coding for acetyl CoA carboxylase can be confirmed in transformed plant cells by determining whether the acetyl CoA carboxylase being expressed retains enzyme activity when exposed to normally toxic levels of herbicides.

2. Promoters

Once a plant acetyl CoA carboxylase gene or functional mutant thereof or an antisense DNA sequence is obtained and amplified, it is combined with a promoter functional in a plant cell to form an expression cassette.

Most genes have regions of DNA sequence that are known as promoters and which regulate gene expression. Promoter regions are typically found in the flanking DNA sequence upstream from the coding sequence in both procaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous genes, that is a gene different from the native or homologous gene. Promoter sequences are also known to be strong or weak or inducible. A strong promoter provides for a high level of gene expression, whereas a weak promoter provides for a very low level of gene expression. An inducible promoter is a promoter that provides for turning on and off of gene expression in response to an exogenously added agent or to an environmental or developmental stimulus. Promoters can also provide for tissue specific or developmental regulation. An isolated promoter sequence that is a strong promoter for heterologous genes is advantageous because it provides for a sufficient level of gene expression to allow for easy detection and selection of transformed cells and provides for a high level of gene expression when desired.

The promoter in an expression cassette of the invention can provide for overexpression of acetyl CoA of a plant acetyl CoA carboxylase gene or functional mutant thereof. Overexpression of the gene is that amount of gene expression that results in an increase in tolerance of the plant cells to an herbicide or that results in an increase in the total oil content of the cells. Overexpression of an acetyl CoA carboxylase gene is preferably about a 2- to 20-fold increase in expression of an acetyl CoA carboxylase over the expression level of the native acetyl CoA carboxylase. The promoter can also be inducible so that gene expression can be turned on or off by an exogenously added agent. For example a bacterial promoter such as the $P_{tac}$ promoter can be induced to varying levels of gene expression depending on the level of isothiopropylgalactoside added to the transformed bacterial cells. It may also be preferable to combine the gene with a promoter that provides tissue specific expression or developmentally regulated gene expression in plants.

Specific promoters functional in plant cells include the 35S cauliflower mosaic virus promoter, nopaline synthase (NOS) promoter and the like. Currently, a preferred promoter for expression in monocots is the 35S cauliflower mosaic virus promoter.

An acetyl CoA carboxylase gene can be combined with the promoter by standard methods as described in Sambrook cited supra. Briefly, a plasmid containing a promoter such as the 35S cauliflower mosaic virus promoter can be constructed as described in Jefferson, *Plant Molecular Biology Reporter,* 5,387 (1987) or obtained from Clontech Lab in Palo Alto, Calif. (e.g. pBI121 or pBI221). Typically these plasmids are constructed to provide for multiple cloning sites having specificity for different restriction enzymes downstream from the promoter. A gene for plant acetyl CoA carboxylase can be subcloned downstream from the promoter using restriction enzymes to ensure that the gene is inserted in proper orientation with respect to the promoter so that the gene can be expressed, In a preferred version, a maize acetyl CoA carboxylase is operably linked to a 35 S CaMV promoter in a plasmid such as pBI121 or pBI221. Once a plant acetyl CoA carboxylase gene is operably linked to a promoter and the plasmid, the expression cassette so formed can be subcloned into other plasmids or vectors.

3. Optional Sequences in the Expression Cassette

The expression cassette can also optionally contain other DNA sequences. The expression cassette can further be comprised of a chloroplast transit peptide sequence operably linked between a promoter and a plant acetyl CoA carboxylase gene. If the expression cassette is to be introduced into a plant cell, the expression cassette can also contain plant transcriptional termination and polyadenylation signals and translational signals linked to the 3' terminus of a plant acetyl CoA carboxylase gene. The expression cassette can also optionally be further comprised of a plasmid.

Because one site of action for biosynthetic pathways involving plant acetyl CoA carboxylase is the chloroplast, an expression cassette of the invention can be combined with an exogenous DNA sequence coding for a chloroplast transit peptide, if necessary. An exogenous chloroplast transit peptide is one which is not encoded within the plant acetyl CoA carboxylase gene. A chloroplast transit peptide is typically 40 to 70 amino acids in length and functions post-translationally to direct the protein to the chloroplast. The transit peptide is cleaved either during or just after import into the chloroplast to yield the mature protein. The complete copy of a gene encoding a plant acetyl CoA carboxylase may contain a chloroplast transit peptide sequence. In that case, it may not be necessary to combine an exogenously obtained chloroplast transit peptide sequence into the expression cassette.

Exogenous chloroplast transit peptide encoding sequences can be obtained from a variety of plant nuclear genes, so long as the products of the genes are expressed as preproteins comprising an amino terminal transit peptide and transported into chloroplast. Examples of plant gene products known to include such transit peptide sequences are the small subunit of ribulose biphosphate carboxylase, ferredoxin chlorophyll a/b binding, protein, chloroplast ribosomal proteins encoded by nuclear genes, certain heatshock proteins, amino acid biosynthetic enzymes such as acetohydroxy acid synthase, 3-enolpyruvylphosphoshikimate synthase, dihydrodipicolinate synthase, and the like. Alternatively, the DNA fragment coding for the transit peptide may be chemically synthesized either wholly or in part from the known sequences of transit peptides such as those listed above.

Regardless of the source of the DNA fragment coding for the transit peptide, it should include a translation initiation codon and an amino acid sequence that is recognized by and will function properly in chloroplasts of the host plant. Attention should also be given to the amino acid sequence at the junction between the transit peptide and the plant acetyl CoA carboxylase enzyme where it is cleaved to yield the mature enzyme. Certain conserved amino acid sequences have been identified and may serve as a guideline. Precise fusion of the transit peptide coding sequence with the acetyl CoA carboxylase coding sequence may require manipulation of one or both DNA sequences to introduce, for example, a convenient restriction site. This may be accomplished by methods including site directed mutagenesis, insertion of chemically synthesized oligonucleotide linkers and the like.

Once obtained, the chloroplast transit peptide sequence can be appropriately linked to the promoter and a plant acetyl CoA carboxylase gene in an expression cassette using standard methods. Briefly, a plasmid containing a promoter functional in plant cells and having multiple cloning sites downstream can be constructed as described in Jefferson cited supra. The chloroplast transit peptide sequence can be inserted downstream from the promoter using restriction enzymes. A plant acetyl CoA carboxylase gene can then be inserted immediately downstream from and in frame with the 3' terminus of the chloroplast transit peptide sequence so that the chloroplast transit peptide is linked to the amino terminus of the plant acetyl CoA carboxylase. Once formed, the expression cassette can be subcloned into other plasmids or vectors.

When the expression cassette is to be introduced into a plant cell, the expression cassette can also optionally include 3' nontranslated plant regulatory DNA sequences. The 3' nontranslated regulatory DNA sequence preferably includes from about 300 to 1,000 nucleotide base pairs and contains plant transcriptional and translational termination sequence. Specific examples of 3' nontranslated regulatory DNA sequences functional in plant cells include about 500 base pairs of the 3' flanking DNA sequence of the pea ribulose biphosphate carboxylase small subunit E9 gene, the 3' flanking DNA sequence of the octopine synthase gene, and the 3' flanking(DNA sequence of the nopaline synthase gene. These 3' nontranslated regulatory sequences can be obtained as described in An, *Methods in Enzymology*, 153:292 (1987) or are already present in plasmids available from commercial sources such as Clontech, Palo Alto, Calif. The 3' nontranslated regulatory sequences can be operably linked to the 3' terminus of a plant acetyl CoA carboxylase gene by standard methods.

An expression cassette of the invention can also be further comprised of a plasmid. Plasmid vectors included additional DNA sequences that provide for easy selection, amplification and transformation of the expression cassette in procaryotic and eukaryotic cells. The additional DNA sequences include origins of replication to provide for autonomous replication of the vector, selectable marker genes, preferably encoding antibiotic resistance, unique multiple cloning sites providing for multiple sites to insert DNA sequences or genes encoded in the expression cassette, and sequences that enhance transformation of prokaryotic and eukaryotic cells. The preferred vectors of the invention are plasmid vectors. The especially preferred vector is the pBI121 or pBI221 vector formed as described by Jefferson cited supra.

Another vector that is useful for expression in both plant and procaryotic cells is the binary Ti vector PGA582. This binary Ti vector has been previously characterized by An, cited supra., and is available from Dr. An. This binary Ti vector can be replicated in procaryotic bacteria such as *E. coli* and Agrobacterium. The Agrobacterium plasmid vectors can be used to transfer the expression cassette to plant cells. The binary Ti vectors preferably include the nopaline T DNA right and left borders to provide for efficient plant cell transformation, a selectable marker gene, unique multiple cloning sites in the T border regions the colE1 replication of origin and a wide host range replicon. The binary Ti vectors carrying an expression cassette of the invention can be used to transform both prokaryotic and eukaryotic cells, but is preferably used to transform plant cells.

B. Method for Screening for Expression and/or Overexpression of a Plant Acetyl CoA Carboxylase Gene A method for screening for expression or overexpression of a plant acetyl CoA carboxylase gene is also provided by the invention. Once formed, an expression cassette comprising an acetyl CoA carboxylase gene can be subcloned into a known expression vector. The screening method in the invention includes the steps of introducing an expression vector into a host cell and detecting and/or quantitating expression of a plant acetyl CoA carboxylase gene. This method of screening is useful to identify expression cassettes providing for an overexpression of a plant acetyl CoA carboxylase gene, antisense molecules that effectively inhibit acetyl CoA carboxylase synthesis, and expression of an acetyl CoA carboxylase in the chloroplast of a transformed plant cell.

Suitable known expression vectors include plasmids that autonomously replicate in prokaryotic and eukaryotic cells. Specific examples include plasmids such as the pBI121 or pBI221 plasmid constructed as described by Jefferson cited supra, a binary Ti vector such as PG582 as described by An cited supra, PUC119, or PBR322. The preferred expression system is a pBI121 or pBI221 plasmid.

An expression cassette of the invention can be subcloned into an expression vector by standard methods. The expression vector can then be introduced into prokaryotic or eukaryotic cells by standard methods including protoplast transformation, Agrobacterium mediated transformation, electroporation, microprojectiles and liposomes. The expression vector can be introduced into plant cells such as tobacco, Brassica, Black Mexican sweet corn, and Arabidopsis cells. The vector can also be introduced into procaryotic cells such as *E. coli* or Agrobacterium. Transformed cells can be selected typically using a selection marker encoded on the expression vector.

Transient expression of a plant acetyl CoA carboxylase gene can be detected and quantitated in the transformed cells. Gene expression can be quantitated by a quantitative Western blot using antibodies specific for the cloned acetyl CoA carboxylase or by detecting an increase in specific activity of the enzyme. The tissue and subcellular location of the cloned acetyl CoA carboxylase can be determined by immunochemical staining methods using antibodies specific for the cloned acetyl CoA carboxylase. Sensitivity of the cloned acetyl CoA carboxylase to herbicides can also be assessed. Expression cassettes providing for overexpression of a plant acetyl CoA carboxylase or acetyl CoA carboxylase tolerant to herbicides can then be used to transform monocot and/or dicot plant tissue cells and to regenerate transformed plants and seeds.

C. Method of Imparting Cyclohexanedione or Aryloxyphenoxypropanoic Acid Herbicide Tolerance to a Plant The invention provides a method of conferring cyclohexanedione or aryloxyphenoxypropanoic acid herbicide tolerance to a plant. The method includes the steps of introducing an expression cassette comprising a gene coding for a plant acetyl CoA carboxylase or a functional mutant thereof operably linked to a promoter into the cells of plant tissue and expressing the gene in an amount effective to render the cells of the plant tissue substantially tolerant to herbicides. An effective amount of gene expression to render the cells of the plant tissue substantially tolerant to the herbicide depends on whether the gene codes for an unaltered acetyl CoA carboxylase gene or a mutant or altered form of the gene that is less sensitive to the herbicides. Expression of an unaltered plant acetyl CoA carboxylase gene in an effective amount is that amount that provides for a 2- to 50-fold increase in herbicide tolerance and preferably increases the amount of acetyl CoA carboxylase from at least about 2-to 20-fold over that amount of the native enzyme. An altered form of the enzyme can be expressed at levels comparable to that of the native enzyme or less if the altered form of the enzyme has higher specific activity. Acetyl CoA carboxylase substantially tolerant to herbicides is an enzyme that is tolerant of levels of herbicide which normally inhibit a native acetyl CoA carboxylase and preferably can function in concentrations of herbicide of about 2- to 20-fold greater than are toxic to the native enzyme.

Herbicide tolerance can be achieved by at least two methods including: 1) by increasing the level of gene expression of a native or unaltered acetyl CoA carboxylase gene; or 2) by introducing an altered gene coding for an acetyl CoA carboxylase that is less sensitive to herbicide inhibition. The level of gene expression can be increased by either combining a plant acetyl CoA carboxylase gene with a promoter that provides for a high level of gene expression such as the 35S CaMV promoter or by introducing the gene into the cells so that multiple copies of the gene are integrated into the genome of the transformed plant cell. Formation of an expression cassette comprised of a plant acetyl CoA carboxylase gene operably linked to a promoter that can be expressed in an effective amount to confer herbicide tolerance has been described previously.

Most monocots, but not dicots, are sensitive to cyclohexanedione and/or aryloxyphenoxypropanoic acid herbicides. The preferred plant cells for introducing an expression cassette of the invention to achieve herbicide tolerance for the plant cells then are monocot plants. Monocot plants include corn, wheat, barley, sorghum, rice, and others. An expression cassette of the invention can be introduced by methods of transformation, especially effective for monocots including biolistic transformation of Type II embryogenic suspension cells as described by W. J. Gordon-Kamm et al., *Plant Cell,* 2, 603–618 (1990), M. E. Fromm et al., *Bio/Technology,* 8, 833–839 (1990) and D. A. Walters et al., *Plant Molecular Biology,* 18, 189–200 (1992) or by electroporation of type I embryogenic calluses described by D'Hafluin et al., *The Plant Cell,* 4, 1495 (1992). Transformed cells can be selected for the presence of a selectable marker gene. Transient expression of a plant acetyl CoA carboxylase gene can be detected in the transgenic embryogenic calli using antibodies specific for the cloned plant acetyl CoA carboxylase. Transformed embryogenic calli can be used to generate transgenic plants that exhibit stable inheritance of either the altered acetyl CoA carboxylase gene or overexpression of the acetyl CoA carboxylase gene. Maize cell lines exhibiting satisfactory levels of tolerance to herbicide are put through a plant regeneration protocol to obtain mature maize plants and seeds expressing the tolerance traits such as described in D'Hafluin. cited supra., or An, cited supra. The plant regeneration protocol allows the development of somatic embryos and the subsequent growth of roots and shoots. To determine that the herbicide-tolerance trait is expressed in differentiated organs of the plant, and not solely in undifferentiated cell culture, regenerated plants are exposed to herbicide levels which will normally inhibit shoot and root formation and growth.

Mature maize plants are then obtained from maize cell lines that are known to express the trait. If possible, the regenerated plants are self-pollinated. Otherwise, pollen obtained from the regenerated plants is crossed to seed-grown plants of agronomically important inbred lines. Conversely, pollen from plants of these inbred lines is used to pollinate regenerated plants. The genetics of the trait are then characterized by evaluating the segregation of the trait in the first and later generation progeny. Stable inheritance of overexpression of a plant acetyl CoA carboxylase or a functional mutant of a plant acetyl CoA carboxylase conferring herbicide tolerance to the plant is achieved if the plants maintain herbicide tolerance for at least about three to six generations.

Seed from transformed monocot plants regenerated from transformed tissue cultures is grown in the field and self-pollinated to generate true breeding plants. Progenies from these plants become true breeding lines which are evaluated for herbicide tolerance in the field under a range of environmental conditions. Herbicide tolerance must be sufficient to protect the monocot plants at the maximum labeled delivery rate under field conditions which cause herbicides to be most active. Appropriate herbicide concentrations and methods of application are those which are known and have been developed for the cyclohexanedione and/or aryloxyphenoxypropanoic acid herbicides in question.

In a preferred version, an expression cassette comprised of a maize acetyl CoA carboxylase gene isolated from a maize cell line tolerant to sethoxydim and haloxyfop and linked to the 35S CaMV promoter is introduced into an herbicide sensitive monocot tissue using biolistic transformation. Transformed calli are selected and used to generate transgenic plants. Transformed calli and transgenic plants can be evaluated for tolerance to sethoxydim and haloxyfop and for stable inheritance of the tolerance trait.

D. Method for Altering the Oil Content in a Plant

The invention also provides a method of altering the oil content in a plant. The method include the steps of introducing an expression cassette comprising a gene coding for plant acetyl CoA carboxylase or functional mutant thereof operably linked to a promoter functional in a plant cell into the cells of plant tissue and expressing the gene in an amount effective to alter the oil content of the plant cell. An alteration in the oil content of a plant cell can include a change in the total oil content over that normally present in that type of plant cell, or a change in the type of oil from that normally present in the plant cell. Expression of the gene in an amount effective to alter the oil content of the gene depends on whether the gene codes for an unaltered acetyl CoA carboxylase or a mutant or altered form of the gene. Expression of an unaltered plant acetyl CoA carboxylase gene in an effective amount is that amount that may provide a change in the oil content of the cell from about 1.2- to 20-fold over that normally present in that plant cell, and preferably increases the amount of acetyl CoA carboxylase about 2- to 20-fold over that amount of the enzyme normally present in that plant cell. An altered form of the enzyme can be expressed at levels comparable to that of the native enzyme or less if the altered form of the enzyme has higher specific activity.

An alteration in oil content of the plant cells according to the method of the invention can be achieved in at least two ways including:

(1) an increase or decrease in expression of an unaltered plant acetyl CoA carboxylase gene; or (2) by introducing an altered or functional mutant plant acetyl CoA carboxylase gene coding for an enzyme that exhibits a change in specific activity.

The level of gene expression of an unaltered plant acetyl CoA carboxylase gene can be increased by either combining an unaltered plant acetyl CoA carboxylase gene with a promoter that provides for a high level of gene expression, such as the 35S cauliflower mosaic virus or by introducing the expression cassette and/or selecting for plant cells having multiple copies of a plant acetyl CoA carboxylase gene integrated into the genome. A decrease in expression of an unaltered acetyl CoA carboxylase can be achieved by transformation with an ACCase antisense gene containing an expression cassette. When an altered or functional mutant plant acetyl CoA carboxylase gene codes for an enzyme that has an increase in specific activity, it may lead to an increase in total oil content of a plant cell even if the level of gene expression is comparable to that of the native enzyme. When an altered or functional mutant acetyl CoA carboxylase gene codes for an enzyme having a decrease in specific activity, it may lead to a decrease in the total oil content of the plant cell compared to that normally present.

An expression cassette as described above can be introduced into either monocots or dicots. Preferably, the expression cassette is introduced into dicot plants such as soybean, canola, and sunflower. An expression cassette can be introduced by standard methods including protoplast transformation, Agrobacterium-mediated transformation, microprojectiles, electroporation, and the like. Transformed cells or tissues can be selected for the presence of a selectable marker gene.

Transient expression of a plant acetyl CoA carboxylase gene can be detected in transformed cells or tissues by immunoreactivity with antibodies specific for the cloned acetyl CoA carboxylase. Overexpression of a plant acetyl CoA carboxylase can be detected by quantitative Western blots. A change in specific activity of the enzyme can be detected by measuring enzyme activity in the transformed cells. A change in total oil content can also be examined by standard methods, as described in Clark & Snyder, *JACS*, 66:1316 (1989).

Transgenic plants and seeds can be generated from transformed cells and tissues showing a change in oil content or in the amount or specific activity of a plant acetyl CoA carboxylase using standard methods. It is especially preferred that the oil content of the leaves, seeds, or fruits is increased.

In a preferred version a maize acetyl CoA carboxylase gene is combined with a 35S cauliflower mosaic virus promoter in a vector such as pBI121 or pBI221 and introduced into soybean cells using the microprojectile method. Transformed soybean cells showing an increase in expression of acetyl CoA carboxylase of at least about 2-fold or at least a 1.2-fold increase in oil content are selected. Transformed soybean cells exhibiting overexpression of acetyl CoA carboxylase or showing an increase in total oil content are used to generate transgenic plants and seeds.

E. Method of Producing Plant Acetyl CoA Carboxylase

The invention also provides a method of producing plant acetyl CoA carboxylase in a host cell. The method includes the steps of introducing an expression cassette comprised of a gene encoding a plant acetyl CoA carboxylase or functional mutant thereof into a host cell and expressing the gene in an amount sufficient to allow for crystallization of the plant acetyl CoA carboxylase. An amount sufficient to allow for crystallization of a plant acetyl CoA carboxylase is about 20- to 100-fold increase over the amount of plant acetyl CoA carboxylase that can normally be purified from plant cells, preferably about 2 to 10 mg protein. Crystallized plant acetyl CoA carboxylase can be used to identify other herbicides that can bind to and inhibit acetyl CoA carboxylase function. In addition, the availability of large amounts of purified enzyme provides for screening of the efficacy of such herbicides.

An expression cassette can include a promoter that is functional in either a eukaryotic or prokaryotic cell. The expression cassette can be introduced into a prokaryotic cell such as *E. coli*, or a eukaryotic cell such as a plant or yeast. The preferred cell is a prokaryotic cell used routinely in producing recombinant proteins such as *E. coli*. The expression cassette can be introduced and transformed cells selected by standard methods.

The plant acetyl CoA carboxylase gene can be expressed in an prokaryotic cell until sufficient amount of the enzyme is produced so that it can be crystallized. Plant acetyl CoA carboxylase can be isolated from bacterial cells using standard methods, including those described in Example V. The purified acetyl CoA carboxylase can then be crystallized and characterized by standard methods.

EXAMPLE I

Identification of Herbicide Mechanism and Site of Action

The objective of this Example was to identify the mechanism whereby sethoxydim and/or haloxyfop inhibit fatty acid synthesis in maize. The results, reported in J. D. Burton et al., *Biochem. Biophys. Res. Comm.*, 148, 1039 (Nov. 13, 1987), show that both sethoxydim and haloxyfop inhibit acetyl-coenzyme A carboxylase (ACCase) (EC 6.4.1.2) in maize chloroplasts.

A. Chemicals

Buffers and cofactors were purchased from Sigma Chemical Company (St. Louis, Missouri); [2-$^{14}$C]acetate was purchased from Research Products International; [2-$^{14}$C] pyruvate and [$^{14}$C]NaHCO$_3$ were purchased from New England Nuclear; and [2-$^{14}$C]malonyl coenzyme A was purchased from Amersham. Sethoxydim was a gift from BASF (Parsippany, N.J.), and haloxyfop was provided by Dow Chemical USA (Midland, Mich.).

B. Plant Growth Conditions

Corn (*Z. mays L.*, 'B37xOh43') seeds were germinated in darkness for 96 hours in vermiculite in an incubation chamber maintained at 30° C., 80% RH. Seedlings were then transferred to a growth chamber with a 16 hour light (25° C.) and an 8 hour dark (20° C.) cycle, 90% relative humidity (RE). After greening 48 hours, seedlings were returned to the dark incubation chamber for 12 hours to deplete chloroplast starch reserves. Seedlings were harvested 6 days after planting. Pea (*P. sativum L.*, 'PI 9901-C') seedlings were grown in vermiculite in a growth chamber with a 16 hour light (21° C.) and 8 hour dark (16° C.) cycle, 80% RH. Peas were harvested 10 to 13 days after planting. Black Mexican Sweet (BMS) corn suspension cultures ware maintained in a supplemented Murashige-Skoog (MS) medium (C. E. Green. *Hort. Sci.*, 12. 7–10 (1977)), and subcultured weekly by 20-fold dilution of the suspension culture into fresh medium.

C. Chloroplast Isolation

Chloroplasts from corn and pea seedlings there isolated at 4° C. (K. Cline et al., *J. Biol. Chem.*, 260, 3691–3696 (1985)). Seedlings (50 g of shoots) were homogenized in 200 ml buffer A (50 mM HEPES-NaOH pH 7.5, 330 mM sorbitol, 0.1% w/v BSA, 1 mM MgCl$_2$, 1 mM MnCl$_2$, 2 mM EDTA, 5 mM isoascorbate, 1.3 mM glutathione) in an omnimixer (five. 3-second bursts at full speed). The homogenate was filtered through six layers of cheesecloth and two layers of miracloth, and then centrifuged at 3000 g for 3 minutes with hand-braking. The pellet was gently resuspended in buffer A and layered onto a preformed linear Percoll gradient (50 mM HEPES-NaOH pH 7.5, 330 mM sorbitol, 1.9 mM isoascorbate, 1.08 mM glutathione, 0.1% w/v BSA, 50% Percoll) which was centrifuged at 3000 g for 20 minutes in a Sorvall HB-4 rotor. The lower band in the gradient, containing intact chloroplasts, was washed twice by gently resuspending it in 20 ml of buffer B (50 mM HEPES-NaOH, pH 7.5, and 330 mM sorbitol) followed by repelleting (3000 g, 5 minutes). The final pellet, consisting of intact chloroplasts, was resuspended in 2 to 3 ml of buffer B and stored on ice in the dark until use.

D. Fatty Acid Synthesis

[$^{14}$C]acetate and [$^{14}$C]pyruvate were used as precursors to measure fatty acid biosynthesis in isolated chloroplasts (B. Liedvogel et al., *Planta*, 169, 481–489 (1986)). [$^{14}$C]acetate incorporation was assayed in a 0.5 ml-volume containing: 50 mM HEPES-NaOH (pH 7.5), 330 mM sorbitol, 5 mM $KH_2PO_4$, 10 mM $NaHCO_3$, 1 mM $MgCl_2$, 1 mM ATP, 0.1 mM CoA, 0.15 mM [$^{14}$C]acetate (3.33 mCi/mmol), and chloroplasts (20 to 50 µg chlorophyll). [$^{14}$C]pyruvate incorporation into fatty acids was assayed in the same medium except that it included 2 mM TPP, 1 mM $NAD^-$. 0.15 mM [$^{14}$C]-pyruvate (1.33 mCi/mmol), but no acetate. Assay suspensions were illuminated with 1400 µE/m$^2$·second PAR at 25° C. Assays were initiated by the addition of the labeled substrate and stopped by the addition of 0.5 ml ol 40% KOH. To determine the incorporation of radiolabel into a non-polar (fatty acid) fraction, each treatment was saponified at 90° C. for 30 minutes in capped vials (P. B. Hoj et al., *Carlsberg Res. Commun.*, 47, 119–141 (1982)). The vials were acidified with 0.5 ml 40% $H_2SO_4$, and carrier fatty acids (20 µg each of C 14:0, C 16:0, and C 18:0) were added. The assay mixture was extracted twice with 4 ml hexane. The extracts were combined, dried under $N_2$, and redissolved in 0.3 ml hexane. Aliquots (50 µl) were counted for radioactivity by liquid scintillation spectrometry.

Incorporation of [$^{14}$C]malonyl-Coenzyme A into fatty acids (P. B. Hoj et al., supra; and J. B. Ohlrogge et al., *Proc. Natl. Acad. Sci. USA*, 76, 1194–1198 (1979)) was assayed using cell-free preparations from BMS tissue culture. Cells harvested during logarithmic growth phase were frozen in liquid nitrogen, ground with a mortar and pestle, and thawed in a medium containing: 0.1 M HEPES-KOH, pH 7.5; 0.3 M glycerol, and 5 mM DTT (buffer:tissue, 2:1, v/w). The homogenate was centrifuged at 12,000 g for 20 minutes. The supernatant was filtered through miracloth and centrifuged (125,000 g) for 60 minutes and then filtered through miracloth and assayed. Assays were conducted at 25° C. in a 0.4 ml volume containing: 1.0 mM ATP, 0.32 mM NADPH, 0.38 mM NADH, 25 µM CoA, 10 µM acetyl-CoA, 25 µg acyl-carrier protein, and 12 µM malonyl-CoA (11.54 µCi/µmol). Reactions were initiated by addition of [$^{14}$C]malonyl CoA and stopped by addition of 0.4 ml 40% KOH. Label incorporation into fatty acids was determined as above. Chlorophyll (D. I. Arnon, *Plant Physiol.*, 24, 1–15 (1949)) and protein (P. K. Smith et al., *Anal. Biochem.*, 150, 76–85 (1985)) were determined as described therein.

E. Acetyl-Coenzyme A Carboxylase (ACCase) Activity

Maize chloroplasts, isolated as described above, were suspended in buffer C (0.1 M Tricine-KOH, pH 8.0; 0.3 M glycerol, and 1 mM DTT) and homogenized in a glass tissue homogenizer. The disrupted chloroplast fraction was centrifuged at 16,000 g for 15 minutes. The supernatant was desalted on a Sephadex G-25 column (1.5×5 cm equilibrated with 0.1 M Tricine-KOH, pH 8.0: and 0.3 M glycerol) and assayed directly. ACCase activity (B. J. Nikolau et al., *Arch. Biochem. Biophys.*, 211, 605–612 (1981)) was assayed at 30° C. in a 0.2 ml volume which contained 1 mM ATP, 3 mM acetyl coenzyme A, 2.5 mM $MgCl_2$, 50 mM KCl, 0.5 mM DTT, and 15 mM [$^{14}$C]$NaHCO_3$ (0.17 mCi/mmol). Reactions were initiated by addition of acetyl coenzyme A and stopped by addition of 25 µl of 12 N HCl. Product formation was determined by the radioactivity found in an acid stable fraction by liquid scintillation spectrometry. Enzyme activity was linear for 15 minutes.

F. Results

To probe for the site of herbicidal activity of sethoxydim and haloxyfop, labeled acetate, pyruvate, and malonyl-CoA were used individually as precursors for fatty acid synthesis. Isolated chloroplasts from corn seedlings incorporated [$^{14}$C] acetate and [$^{14}$C]pyruvate into a non-polar fraction (fatty acids). Acetate incorporation was linear for 30 min after a 5 min lag period, and dependent upon the addition of free acetyl coenzyme A. Addition of either 10 µM sethoxydim or 1 µM haloxyfop inhibited [$^{14}$C]acetate incorporation into fatty acids by 90% and 89%, respectively, as shown in Table I, below. Sethoxydim (10 µM) and haloxyfop (1 µM) also inhibited the incorporation of [$^{14}$C]pyruvate into fatty acids by 98% and 99%, respectively.

TABLE I

Inhibition of [$^{14}$C]acetate and [$^{14}$C]pyruvate Incorporation into Fatty Acids in Corn Seedling Chloroplasts by Sethoxydim (10 µM) and Haloxyfop (1 µM), 10 minute assay time

|  | Acetate | Pyruvate |
|---|---|---|
|  | Activity (nmol/mg chl · min) | |
| Control | 4.4 ± 0.4[1] | 10.8 ± 2.3 |
|  | % Inhibition | |
| Sethoxydim | 90 ± 2.5 | 98 ± 1.1 |
| Haloxyfop | 89 ± 3.1 | 99 ± 0.3 |

[1]Results are expressed as mean of two experiments ± standard error.

The effect of 10 µM sethoxydim and 1 µM haloxyfop on [$^{14}$C]malonyl-CoA incorporation into fatty acids was determined using cell-free extracts from corn suspension cultures. Neither sethoxydim (10 µM) nor haloxyfop (1µM) inhibited fatty acid synthetase activity. Thus, both herbicides inhibited fatty acid synthesis in intact chloroplasts from corn seedlings with either acetate or pyruvate as a precursor, but did not inhibit incorporation of malonyl-CoA into fatty acids. This suggests that ACCase which catalyzes the formation of malonyl-CoA is the site of action of these herbicides.

EXAMPLE II

Selection and Characterization of Herbicide-tolerant Cell Lines

A selection protocol to identify and isolate herbicide-tolerant maize cells was developed to minimize the adverse effects of high herbicide concentrations on somatic embryo development and plant regeneration capacity. The procedure involved exposing tissue to gradually increasing concentrations of herbicide beginning with a sethoxydim concentration representing ⅟₂₀th of lethal dose and doubling the herbicide concentration at approximately two-week intervals until the lethal dose (10 µM sethoxydim) was reached. In this way, the herbicide was allowed to take effect slowly with continuous selection pressure, thus permitting herbicide-tolerant cells to accumulate over time while not affecting the potential for plant regeneration.

A. Selection of a Sethoxydim-Tolerant Cell Line

Many selections were carried out utilizing the selection protocol described in the preceding paragraph. The selection of one such sethoxydim-tolerant cell line that was identified and characterized is described below in detail.

Approximately 100 grams of vigorously growing regenerable, friable, embryogenic maize callus tissue established from an $F_1$ immature embryo resulting from the cross A188×B73 were transferred to agar-solidified maintenance medium (Armstrong and Green, Planta. 164. 207 (1985)) in petri plates containing 0.5 $\mu$M sethoxydim (BASF) (Parsippany, N.J.). This callus line was designated 2167-9/2160-154. Forty plates were prepared and five clumps of callus tissue weighing about 0.5 grams each were placed on each plate. The 0.5 $\mu$M sethoxydim concentration was chosen from growth inhibition studies to provide less than 10–20% growth inhibition during the first two weeks of herbicide exposure. After 14 days, 0.25–0.5 gram pieces of tissue showing vigorous growth rate and retention of embryogenic morphology (i.e., presence of somatic embryos) were subcultured on fresh medium containing 1.0 $\mu$M sethoxydim. Eighty plates containing five pieces of tissue per plate were prepared. For each subsequent transfer, all callus tissue showing growth and somatic embryo forming ability was placed on fresh media containing a two-fold increased sethoxydim concentration. Therefore, callus was transferred at two-week intervals to petri plates containing 0.5, 1.0, 2.0, 5.0 and 10.0 $\mu$M sethoxydim. During the course of the selection process, the total number of lines decreased as the herbicide-mediated growth inhibition became more intense. Cell lines exhibiting growth on 10 $\mu$M sethoxydim were designated as herbicide-tolerant and given an identification number. Two sethoxydim-tolerant lines were recovered that exhibited uninhibited growth at 10 $\mu$M sethoxydim. These lines were designated 2167-9/2160-154 S-1 and 2167-9/2160-154 S-2.

B. Characterization of Herbicide-Tolerant Maize Cell Line 2167-9/2160-154 S-2

Figure 2:
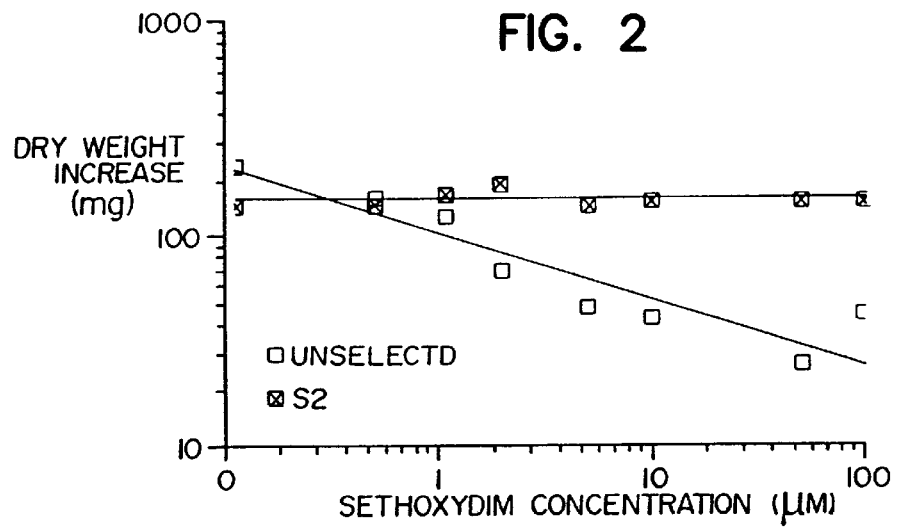
FIG. 2 is a graph depicting the effect of sethoxydim on the growth of mutant maize callus.

Tolerant cell line 2167-9/2160-154 S-2 ("S-2") was characterized to evaluate: (1) the magnitude of sethoxydim tolerance; (2) cross-tolerance of haloxyfop: and (3) the biochemical basis for the tolerance. Callus tissue from S-2 that had been maintained on 10 $\mu$M sethoxydim was transferred to media containing up to 100 $\mu$M sethoxydim. One-half gram of S-2 tissue was plated on a 7 cm filter paper as a lawn overlaying 50 ml agar-solidified culture medium containing 0. 0.5. 1.0, 2.0, 5.0, 10.0, 50.0 and 100 $\mu$M sethoxydim, and cultured for two weeks. Control cell line 2167-9/2160-154 was plated similarly on medium containing the same levels of sethoxydim. The results of this study are summarized in FIG. 2. The control cell line growth after two weeks was inhibited 50% at 1 $\mu$M sethoxydim. Growth of S-2 was not inhibited at 100 $\mu$M sethoxydim, indicating that S-2 was at least 100-fold more tolerant than the control callus line.

Growth of S-2 was inhibited with 0.65 $\mu$M haloxyfop, whereas the control cell line was inhibited 50% with 0.02 $\mu$M, indicating approximately a 30-fold increase in tolerance.

C. Acetyl-Coenzyme A Carboxylase (ACCase) Activity of Maize Cell Line S-2

Assays were conducted to determine if ACCase extracted from cell line S-2 was altered with respect to herbicide activity. ACCase activity of control tissue was 50% inhibited either by 1.5 $\mu$M sethoxydim, or by 0.25 $\mu$M haloxyfop. ACCase activity of S-2 tissue was inhibited 50% either by 70 $\mu$M sethoxydim, or by 1.8 $\mu$M haloxyfop, indicating at least 40-fold and 7-fold decreases in herbicide sensitivity on concentration basis, respectively.

EXAMPLE III

Plant Regeneration and Production of Herbicide-Tolerant Seed

A. Plant Regeneration Protocol

Sixteen ca. 150 mg clumps of S-2 callus were transferred per 25×100 mm petri plate containing agar-solidified N6 basal salts and 6% sucrose and incubated 7–14 days in low light (20 $\mu$E m$^{-2}$ s$^{-1}$). Several plates containing callus on plant regeneration medium were prepared. Callus was transferred to agar-solidified Murashige-Skoog (MS) medium without hormones and incubated in high intensity light (200 $\mu$E m-2 s$^{-1}$) for shoot elongation. Developing plants (I-3 cm long) were isolated from the callus surface and transferred to magenta boxes containing agar-solidified MS salts, 2% sucrose with no hormones for two weeks of further growth. When plants reached the 2–3 leaf stage, they were transplanted to peat pots containing potting soil, and were incubated in the growth room until growing stably. Surviving plants were transferred to soil in 4" diameter plastic pots and grown in the greenhouse.

Figure 3:
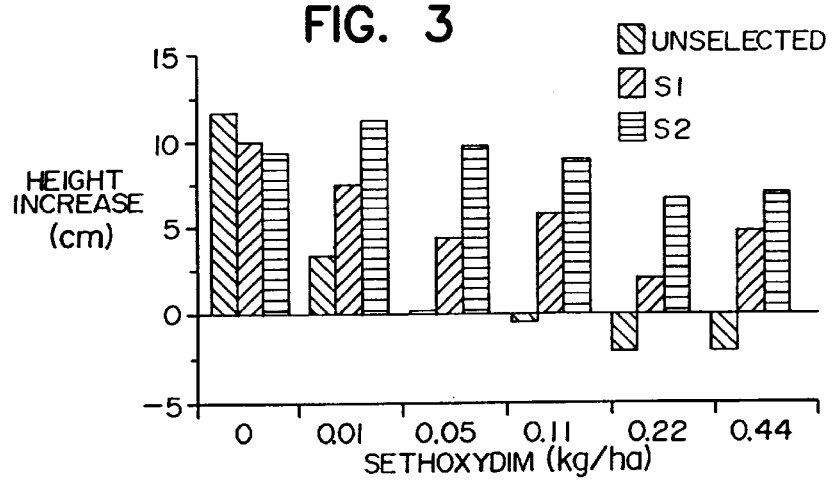
FIG. 3 is a graph depicting the shoot length growth of maize seedlings seven days after treatment with sethoxydim.
Figure 4:
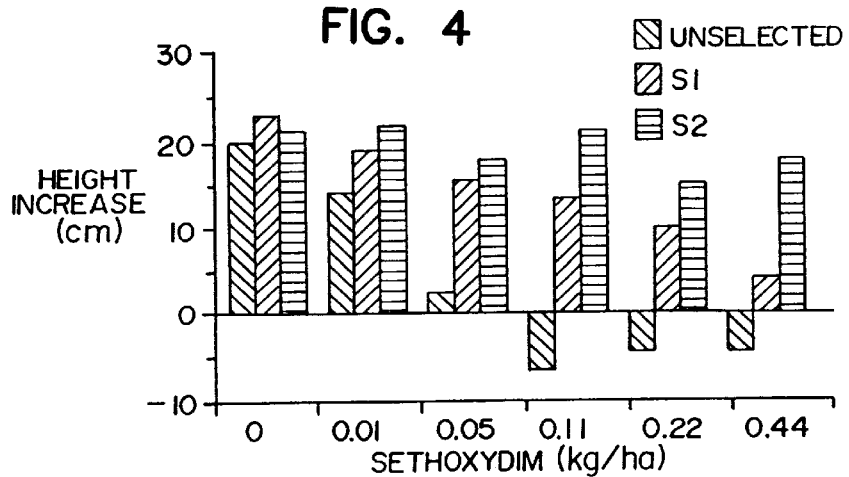
FIG. 4 is a graph depicting the shoot length growth of maize seedlings fourteen days after treatment with sethoxydim.

B. Expression of Herbicide Tolerance in Plants Regenerated from S-2 Callus Tissue Groups of eight control (2167-9/2160-154 unselected) and eight S-2 plants were sprayed with either 0.0, 0.01. 0.05, 0.11, 0.22 or 0.44 kg/ha sethoxydim to determine whole plant sethoxydim-tolerance of greenhouse-grown plants. Control plants were killed by 0.05 kg/ha or more sethoxydim. Plants regenerated from the S-2 cell line survived the 0.44 kg/ha sethoxydim treatment, indicating that S-2 plants exhibit at least 20-fold more tolerance of sethoxydim than control. FIG. 3 shows the growth response of the regenerated plants seven days after treatment with 0.44 kg/ha sethoxydim. As shown in FIG. 4, shoot height of regenerated S-2 plants was only slightly reduced 14 days after treatment with 0.44 kg/ha sethoxydim.

C. Seed Production from S-2 Plants

Plants surviving sethoxydim treatments of up to 0.44 kg/ha were transplanted to the genetics plot on the University of Minnesota campus, St. Paul, Minnesota. Additional S-2 plants were transplanted to the field that had not been sprayed. Sixty-five 2167-9/2160-154 control plants and ninety-five S-2 plants were grown to maturity in the field. Plants were either self-pollinated or cross-pollinated to inbred maize lines A188, A619, A641. A661, A665, B37, B73, R806, and W153R. Control seed were produced by selfing 2167-9/2160-154 regenerated plants, or by crossing them with the inbreds listed above.

D. Expression of Herbicide Tolerance in Progeny of Regenerated Plants

Seeds obtained by the crossing procedure described above were viable and germinated normally. Seeds from thirty S-2 selfed plants and fifteen 2167-9/2160-154 control plants were planted in 25×50 cm trays of soil (28 seeds from each plant in one tray) and grown in the greenhouse. Seedlings at the 3–4 leaf stage were treated with 0.1, 0.44, and 1.1 kg/ha sethoxydim and evaluated for visual herbicide damage and shoot height. Based on visual rating of herbicide damage two weeks after treatment, selfed progeny of S-2 plants segregated approximately 1:2:1 for healthy, uninjured plants: to plants showing partial injury: to dead plants, respectively at 0.44 and 1.1 kg/ha sethoxydim treatments. All control progeny of 2167-9/2160-154 control plants were killed by 0.1 kg/ha and greater levels of sethoxydim. These results demonstrate dominant expression of sethoxydim tolerance indicating that sethoxydin tolerance in S-2 plants is a heritable trait. Similar tests were conducted on progeny of S-2 plants crossed to the other inbreds. In all cases, these test cross progeny treated with 0.44 kg/ha sethoxydim segregated 1:1 for growing shoots versus dead shoots whether S-2 plants were used as male or female parents. These results confirm that sethoxydim tolerance is controlled by, a single dominant nuclear gene. In all cases, control plants crossed to the other inbreds were killed and therefore sethoxydim-sensitive.

E. Method for Obtaining Uniform Herbicide-Tolerant Seed

Progeny of S-2 plants surviving sethoxydim treatments of 0.44 and 1.1 kg/ha and showing no herbicide injury were transferred to the greenhouse and grown to maturity. These plants may be selfed and their progeny evaluated for sethoxydim and haloxyfop tolerance to identify pure breeding herbicide-tolerant maize lines.

Progeny of S-2 plants crossed to inbred lines and exhibiting sethoxydim tolerance may be recurrently backcrossed to the same inbreds. Progeny of each cross may be screened for sethoxydim-tolerance, and tolerant plants grown to maturity and again crossed to the recurrent parent. After six or seven cycles of backcrossing, sethoxydim-tolerant plants may be selfed and progeny screened for tolerance to produce homozygous sethoxydim tolerant maize inbreds.

EXAMPLE IV

Selection of Additional Herbicide-Tolerant Maize Cell Lines

One primarily sethoxydim-tolerant maize cell line, 2167-9/2160-154 S-1. and two haloxyfop-tolerant maize cell lines. 2167-9/2160-154 H-1 and 2167-9/2160-154 H-2. were selected and characterized as follows:

A. Selection of Maize Cell Line 2167-9/2160-154 S-1

Maize cell line 2167-9/2160-154 S-1 was selected from maize cell culture using the protocol described in detail above for the selection of Line 2167-9/2160-154 S-2. Approximately 70 plants were regenerated from Line 2167-9/2160-154 S-1. and either self-pollinated or cross-pollinated to the inbred maize lines A188. A619, A641, A661, A665, B37, B73. R806. and W153R.

B. Selection of Maize Cell Line 2167-9/2160-154 H-1

Line 2167-9/2160-154 H-1 was selected from maize cell culture using a similar protocol described in detail above except maize callus tissue was selected using the herbicide haloxyfop. Maize callus tissue was initially plated on 0.01 µM haloxyfop. At two-week intervals, surviving tissue was subcultured onto 0.05, 0.10 and 0.20 µM haloxyfop. Approximately 50 plants were regenerated from Line 2167-9/2160-154 H-1, and were self-pollinated.

C. Selection of Maize Cell Line 2167-9/2160-154 H-2

Line 2167-9/2160-154 H-2 was selected from maize cell culture using a similar protocol described in detail for line 2167-9/2160-154 H-1. No plants have been successfully regenerated from this line.

D. Characterization of Lines 2167-9/2160-154 S-1, H-1 and H-2

The tolerant callus cultures were characterized to determine the magnitude of sethoxydim and haloxyfop tolerance. Callus tissue from these lines was evaluated in experiments as described above in the characterization of line 2167-9/2160-154 S-2. Table II summarizes the results of these studies. Line 2167-9/2160-154 S-1 and Line 2167-9/2160-154 H-2 showed a four-fold increase in haloxyfop tolerance, while Line 2167-9/2160-154 H-1 exhibited approximately a 60-fold increase in haloxyfop tolerance. Neither haloxyfop selected line showed a significant degree of sethoxydim tolerance, while the sethoxydim selected line S-1 exhibited approximately a 100-fold increase in sethoxydim tolerance.

TABLE II

Herbicide Tolerance of Cell Lines S-1, H-1 and H-2

| Cell Line | Herbicide | |
|---|---|---|
| | Haloxyfop | Sethoxydim |
| 2167-9/2160-154 S-1 | 4[1] | 100 |
| 2167-9/2160-154 H-1 | 61 | 0 |
| 2167-9/2160-154 H-2 | 4 | 0 |

[1]The numbers represent the fold increase in herbicide concentration that results in a 50% reduction in growth of the selected cell lines compared to the unselected control cell line 2167-9/2160-154.

E. Herbicide Inhibition of Acetyl Coenzyme A Carboxylase of Maize Cell Lines S-1, H-1 and H-2

Acetyl Coenzyme A Carboxylase (ACCase) was extracted from cell lines S-1, H-1 and H-2 and assayed as described in detail for maize cell line S-2, above. Table III below summarizes the results of these studies. The ACCase from line S-1 was more tolerant of both sethoxydim and haloxyfop, while the ACCase from line H-1 was more tolerant of haloxyfop, but not of sethoxydim. The ACCase from line H-2 showed no difference from the unselected parent line 2167-9/2160-154 in sensitivity to either herbicide.

However, cell line H-2 exhibited approximately a five-fold higher level of ACCase activity as compared to the unselected parent line 2167-9/21 60-154. Thus, selection for sethoxydim or haloxyfop tolerance resulted in a less sensitive ACCase in cell line S-1 and H-1. as well as a higher level of ACCase activity in cell line H-2.

TABLE III

Herbicide Inhibition of ACCase of Maize Cell Lines S-1, H-1 and H-2

| Cell Line | Herbicide | |
|---|---|---|
| | Haloxyfop | Sethoxydim |
| 2167-9/2160-154 S-1 | 3 | 4 |
| 2167-9/2160-154 H-1 | 7 | 0 |
| 2167-9/2160-154 H-2 | 0 | 0 |

[1]The numbers represent the fold increase in herbicide concentration that inhibits ACCase activity of the selected cell lines by 50% compared to the unselected parent cell line 2167-9/2160-154.

Deposit of Seeds

Seeds from representative S-2 plants (Ex. III (B)) and H-1 plants (Ex. IV(B)) have been deposited with the American Type Culture Collection, 12301 Parklawn Drive, Rockville, Md. 20852 USA on October 25. 1988 and assigned accession numbers ATCC 40507, and ATCC 40508, respectively.

EXAMPLE V

Formation of cDNA Clones Encoding ACCase

A. ACCase Purification

The acetyl CoA carboxylase enzyme was isolated and purified from plant tissues and characterized. The purified enzyme was used to generate antibody reagents useful in identifying cDNA clones encoding the gene or portions of the gene for ACCase.

ACCase was extracted from frozen shoots of 7-d-old maize (*Zea Mays* L. inbred A619 or B73) seedlings grown in a growth chamber (24° C., 90% RH, 16-h daylength at 210 µE m$^{-2}$ s$^{-1}$). The outermost leaf and blade were removed and the remainder of the shoot was frozen in liquid N$_2$. Embryos and endosperm tissue from developing kernels were harvested from field-grown ears at 36 to 40 days after pollination (DAP). Black Mexican Sweet corn (BMS) maize suspension cells were obtained from cultures as previously described (W. B. Parker et al., *Plant Physiol.*, 99, 1220–1225 (1990)). Tissues were stored in liquid N, until used.

Extraction and purification steps were performed at 0 to 4° C. Crude extracts of leaf, bundle sheath strands, embryo, endosperm, and BMS cells were prepared from frozen tissue as described by W. B. Parker et al., *Proc. Nat'l Acad. Sci. USA*, 87. 7175–7179 (1990), except that extraction buffer contained 0.1 M Tricine-KOH, pH 8.3, 0.3 M glycerol, 5 mM DTT. 2 mM Na$_2$EDTA, and 0.5 mM phenyl methonyl sulfonyl fluoride (PMSF). Triton X-100 (0.01% v/v) was added to bundle sheath strand extracts and to some whole leaf extracts. For some experiments, additional protease inhibitors (leupeptin, 2 µg mL; pepstatin A, 100 µg mL$^{-1}$; benzamidine, 1 mM; P-amino-n-caproic acid, 5 mM; and soybean trypsin inhibitor. 10 µg mL$^{-1}$) were included. Filtered homogenates were centrifuged 20 minutes at 30,000 g. A portion of the crude supernatant fraction was immediately boiled 5 minutes in 1 volume of SDS sample buffer (W. B. Parker et al., *Plant Physiol.*, 92, 1220–1225 (1990)) for SDS-PAGE analysis; the remainder was desalted on a 10-mL Sephadex G-25 column into extraction buffer minus PMSF.

ACCase was purified from the crude extract supernatant in four steps. This fraction was brought to 30% saturation with solid (NH$_4$)$_2$SO$_4$, stirred 15 minutes, and centrifuged 20 minute at 20,000 g. The supernatant was then brought to 40% saturation with (NH$_4$)$_2$SO$_4$ solution, stirred 30 minutes, and centrifuged. The pellet was dissolved in 5 mL extraction buffer, microfuged 5 minutes, and the resulting supernatant was applied to a Sephacryl S-300 gel filtration column (Pharmacia; 2.5×46 cm) equilibrated with S-300 buffer (0.1 M Tricine-KOH, pH 8.3, 0.5 M glycerol, 0.5 mM DTT, 2 mM NaSO mM KCl). In later experiments a Sephacryl S-400 column was used. Fractions (2.5 mL) were eluted at 0.75 mL min$^{-1}$. ACCase activity eluted shortly after the void A$_{280}$ peak (V$_0$=75 mL). Active fractions were pooled, brought to 4.25 mM MgCl$_2$ (from a 0.5 M solution), and applied at 0.2 mL min$^{-1}$ to a Blue Sepharose CL-6B (Pharmacia; 1.5×15 cm) equilibrated with Blue sepharose buffer (S-300 buffer containing 4.25 mM MgCl$_2$ and 10 mM NaHCO$_3$). The column was washed overnight with 150 mL buffer (0.45 mL min$^{-1}$). ACCase activity was then eluted with 50 mL buffer plus 10 mM ATP (0.45 mL min$^{-1}$). Active fractions were pooled and applied to an FPLC Mono-Q HR 5/5 anion-exchange column (Pharmacia) equilibrated with S-300 buffer minus KCl. The column was washed with 30 mL S-300 buffer minus KCl and then with a 48-mL. 0 to 500 mM KCl gradient in S-300 buffer (0.25 mL min$^{-1}$). Fractions (1 mL) from the two peaks of ACCase activity were pooled separately. All purification fractions were. desalted into S-300 buffer and assayed for ACCase activity and protein.

ACCase was also analyzed from mesophyll chloroplasts and bundle sheath strands. Mesophyll chloroplasts from homogenates of 7- to 8-day-old seedlings that were kept in the dark 24 hours prior to harvesting were isolated on a linear Percoll gradient according to J. D. Burton et al., *Pesticide Biochemistry and Physiology*, 34, 76–85 (1989), except that buffers contained 0.6 M sorbitol and centrifugation g-forces were reduced by 25%. Intact chloroplasts were taken from the discrete lower green band present after Percoll gradient centrifugation (G. Morioux et al., *Plant Physiol.*, 67, 470–473 (1981)). Pelleted chloroplasts were lysed by resuspending them in ACCase extraction buffer plus PMSF and 0.01% (v/v) Triton X-100. Bundle sheath strands were obtained from the original leaf homogenate material retained on a 70-µm filter after re-homogenizing the retentate five times in a total of 2 L buffer. Triton X-treated, desalted leaf, mesophyll chloroplast, and bundle sheath strand extracts were assayed for activities of Rubisco (G. Zhu et al., *Plant Physiol.*, 97, 1348–1353 (1991)), NADP-dependent malate dehydrogenase (M. D. Hatch et al., *Biochem. Biophys. Res. Commun.*, 34, 589–593 (1969)), phosphoenolpyruvate carboxylase (R. C. Leegood et al., "Isolation of Membranes and Organelles from Plant Cells," Academic Press, New York, 185–210(1983)), catalase (Worthington Biochemicals, 1972), and fumarase (R. L. Hill et al., *Methods Enzymol.*, 13, 91–99 (1969)), and for total chlorophyll (D. E. Arnon, *Plant Physiol.*, 24, 1–5 (1949)). Mesophyll chloroplast preparations were judged to be relatively free of contamination by bundle sheath chloroplasts because they contained 3-fold greater NADP-dependent malate dehydrogenase and one-tenth as much Rubisco activity (mg-1 chlorophyll) than bundle sheath strand extracts. Mesophyll chloroplast preparations also contained ≦2.6% as much catalase, fumarase, and phosphoenolpyruvate carboxylase activities (mg$^{-1}$ chlorophyll) as did whole-leaf extracts, indicating they were relatively free of peroxisomal, mitochondrial, or cytoplasmic components.

ACCase activity as measured by acetyl-CoA-dependent H$^{14}$CO (ICN. 2.07 GBq mmol$^{-1}$) incorporation into acid-stable product previously shown to be malonyl-CoA (J. D. Burton et al., *Pesticide Biochemistry and Physiology*, 34, 76–85 (1989)). Assays of desalted purification fractions or crude, desalted tissue extracts contained up to 50 and 25% (v/v) enzyme, respectively. In some experiments methylcrotonyl-CoA or propionyl-CoA were substituted for acetyl-CoA (E. S. Wurtele et al., *Archives of Biochemistry and Biophysics*, 278, 179–186 (1990)). Avidin (10 U mL$^{-1}$) was included in some assays. Herbicide inhibition assays contained 1% (v/v) ethanol plus or minus 1 µM haloxyfop (2-[4-[[3-chloro-5-(trifluoromethyl)-2-pyridinyl]oxy]phenoxy]propanoic acid, Dow Chemical Co. analytical grade racemic mixture) or 10 µM sethoxydim (2-[1 [(ethoxylmino)butyl]-5-[2-(ethylthio)-propyl]-3-hydroxy-2-cyclohexene-1-one, Li salt, BASF Corp. technical grade). Data are means plus standard error of three assays.

Protein concentrations were determined in duplicate with the Bio-Rad Coomassie blue dye-binding assay as described by the manufacturer, using BSA as the standard.

Centrifuged crude extracts and proteins in purification fractions and immunoprecipitation supernatants were separated by SDS-PAGE in 6 or 7.5% gels as previously described (W. B. Parker et al., *Plant Physiol.*, 92 1220–1225 (1990)). Purification fractions were precipitated in 10% (v/v) TCA, washed with 80% (v/v) acetone, and air-dried 10 minutes prior to electrophoresis. Proteins in gels were stained with silver (J. Heukeshoven et al., *Electrophoresis*, 6 103–112 (1985)). High molecular weight protein standards for SDS-PAGE (Pharmacia) were used to estimate polypeptide masses.

The four-step purification procedure shown in Table IV typically yielded 30 to 190 µg of highly purified ACCase from 50 grams (fresh weight) of maize inbred A619 or B73 seedling leaves. ACCase activity in the crude supernatant fraction precipitated between 30 and 40% saturation with (NH$_4$)$_2$SO$_4$, which appeared to increase total ACCase activity approximately 38%. Crude a extract components might have depressed the reaction rate shown in Table IV because the assay mixture contained 50% enzyme (v/v). In tests of fractions from another purification, enzyme velocity was proportional to enzyme concentration in assay mixtures containing up to 25% (v/v) crude extract, but 50% (v/v) mixtures were not tested. ACCase activity eluted from the Sephacryl S-300 gel filtration column slightly after the green void peak. Approximately 56% of the S-300 fraction ACCase activity was recovered from the Blue Sepharose column, primarily in the initial ATP-containing fractions (12.5 mL). Both 10 mM $NaHCO_3$ and 4.25 mM $MgCl_2$ (1- and 0.85-fold standard assay concentrations, respectively) were included in the Blue Sepharose buffer because they improved the total and specific ACCase activity remaining after batch absorption to Blue Sepharose beads, elution with ATP, and desalting into extraction buffer minus PMSF. Neither $NaHCO_3$ nor $MgCl_2$ improved enzyme stability of crude extracts. Mono-Q anion-exchange chromatography resulted in separation of two ACCase activity peaks which eluted at approximately 210 mM (designated ACCase II) and 250 mM KCl (designated ACCase I), as previously observed for a hybrid maize variety (J. L. Howard et al., *FEBS Lett.*, 261, 261–264 (1990)). ACCase I comprised about 85% of the total activity recovered from the column (29% of the original crude extract activity) and had high specific activity (Table IV). The specific activity of ACCase II was less than 30% that of ACCase I. Both activities were inhibited >90% by avidin, as previously reported (J. L. Howard et al., *FEBS Lett.*, 261, 261–264 (1990)). The mass of native ACCase I was estimated to be approximately 490 kD by gel filtration on Superose 6.

TABLE IV

Purification of AC Case I From
Maize Inbred A619 Seedling Leaves[a]
All fractions were desalted into S-300 buffer and assayed
for protein and acetyl CoA dependent incorporation of
[$^{14}C$]$HCO_3^-$ into acid-stable products

| Step | Protein mg | Activity units[b] | Specific Activity units/mg | Fold Purification | Activity Yield |
|---|---|---|---|---|---|
| Crude extract | 215 | 2.45 | 0.0114 | 1 | 100 |
| 30–40% $(NH_4)_2SO_4$ | 45.1 | 3.37 | 0.0748 | 6.56 | 138 |
| S-300 | 10.7 | 3.35 | 0.313 | 27.5 | 137 |
| Blue Sepharose | 1.50 | 1.86 | 1.24 | 109 | 76 |
| Mono-Q (ACCase I) | 0.130 | 0.720 | 5.54 | 486 | 29 |

[a]Data are from one purification experiment starting with 50 g fresh weight of tissue and are representative of data obtained for eight purifications.
[b]Unit = 1 μmol acid-stable product $min^{-1}$.

B. Formation and Specificity of Antibodies to ACCase

Antibodies are sensitive reagents that allow for the identification of gene products from cDNA and other cloned genes. Antibodies to purified ACCase were prepared and used to screen for cDNA clones encoding all or a portion of a gene for ACCase.

Antiserum to maize ACCase was obtained by immunizing a female New Zealand White rabbit (Egli et al., *Plant Physiol.*, 101, 499 (1993)). An intramuscular injection of 100 μg of Mono-Q-purified, SDS-denatured ACCase I in Freund's complete adjuvant was followed by subcutaneous injections of 20 to 100 μg of gel-purified ACCase I polypeptide in acrylamide plus incomplete adjuvant every 4 to 6 weeks, for a total of six injections. Serum was stored at −20° C. in 0.02% (w/v) $NaN_3$.

For Western blots, proteins in SDS gels were electrophoretically transferred to Immobilon (W. B. Parker et al., *Plant Physiol.*, 92, 1220–1225 (1990)) for 1 hour at 20 V in a Bio-Rad Transphor semi-dry blotter and then stained with Ponceau S (E. Harlow et al., "Antibodies—A Laboratory Manual, Cold Spring Harbor Laboratory, Cold Spring Harbor, N.Y. (1988)). Destained blots were blocked with Tris-buffered saline plus 0.5% (v/v) Tween-20 (Bio-Rad), and 10% (w/v) bovine serum (for antiserum blots only). ACCase and biotinylated proteins were detected with immune serum (1/10.000) plus goat anti-rabbit IgG-alkaline phosphatase conjugate or with avidin-alkaline phosphatase (W. B. Parker et al., *Plant Physiol.*, 92, 1220–1225 (1990)). Blots were repeated at least three times.

For immunoprecipitations, equal ACCase activities (0.58 nmol $min^{-1}$) in crude extracts were desalted into S-300 buffer containing 0.1 M KCl and incubated 1 hour at 25° C. with 16 μL buffer or with 16 μL serum consisting of 0 to 100% ACCase antiserum in preimmune serum. Immune complexes were incubated 1 hour at 25° C. with a 2-fold (IgG binding) excess of Protein A-agarose and then microfuged 5 minutes to obtain immunoprecipitation supernatant fractions. ACCase activity of supernatants was expressed as a percent of the 100% preimmune serum control. Data are means plus SE of three replicate assays for each of two sets of extracts.

Figure 5:
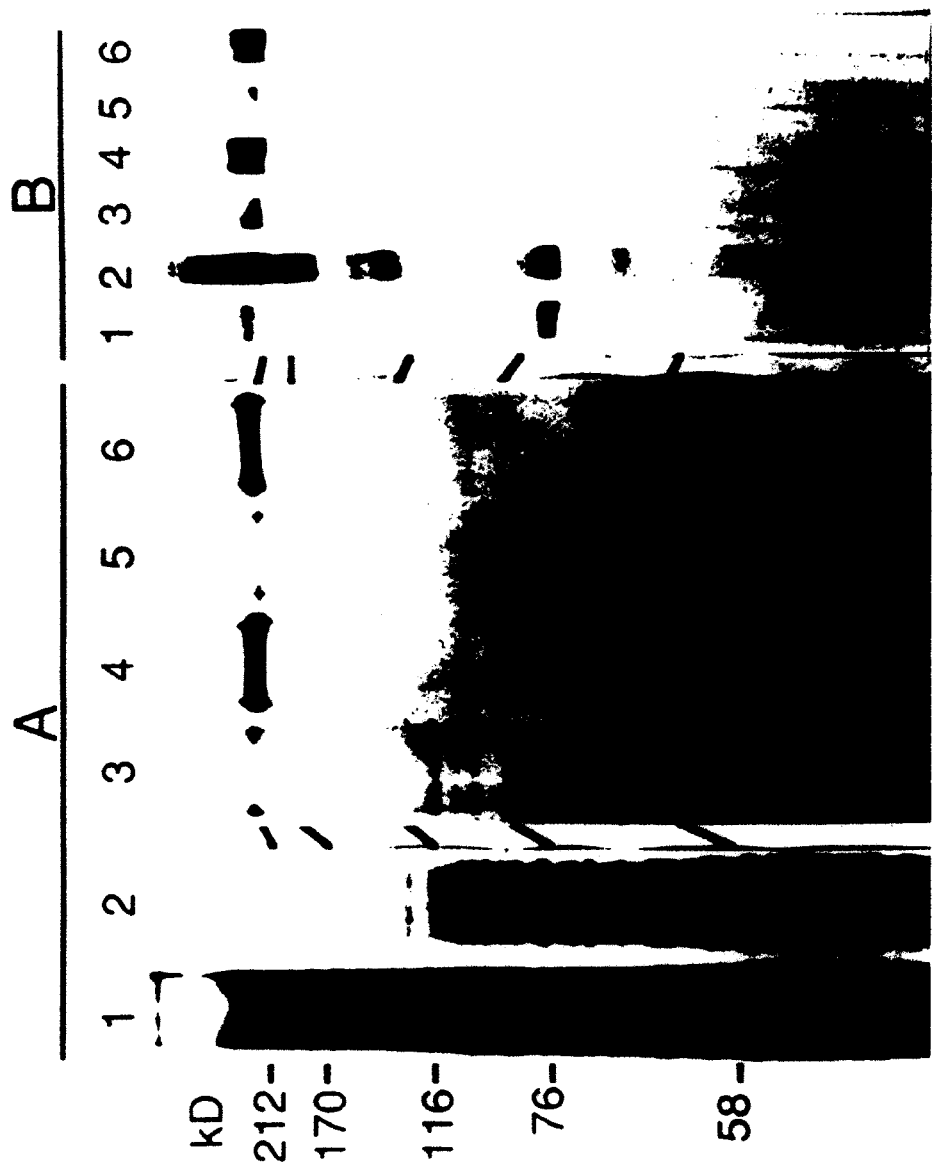
FIG. 5: Total soluble and biotinylated polypeptides in ACCase purification fractions from seedling leaves of maize inbred A619. Proteins were separated by SDS-PAGE in 7.5% gels and then silver-stained (Panel A). An identical gel was Western-blotted and a longitudinal section of each lane was probed with avidin (Panel B). Lanes were 1: crude (10 µg); 2: $(NH_4)_2SO_4$ (10 µg); 3: S-300 (5 µg); 4: Blue Sepharose (2 µg); 5: Mono-Q ACCase II (5 µg); and 6: Mono-Q ACCase I (5 µg). Diagonal lines between lanes indicate position of molecular weight markers shown on the left.

Western blots and silver-stained gels of purification fractions separated by 7.5% SDS-PAGE showed that neither ACCase I nor ACCase II Mono-Q fractions contained biotinylated polypeptides smaller than 212 kD. A polypeptide >212 kD was the primary protein component of the ACCase I Mono-Q fragment (FIG. 5). The ACCase II fraction contained a biotinylated polypeptide >212 kD and a large amount of a 55 kD non-biotinylated polypeptide. Fractions from earlier purification steps contained additional biotinylated proteins of approximately 74, 75, and 125 kD (FIG. 5).

To better compare the biotinylated polypeptides >212 kD in ACCase fractions I and II, we used 6% SDS-PAGE, which showed that the mass of ACCase II was approximately 8 kD less than that of ACCase I. Molecular masses were estimated to be 219 kD (ACCase II) and 227 kD (ACCase I), based on comparisons with polypeptide standards and the observation (N. R. Palosaari, *Plant Physiol.*, 99(S), 359 (1992)) that, on Phastgels (Pharmacia), ACCase I polypeptide was slightly smaller than dodecameric horse spleen ferritin (238 kD; M. Heusterspreute et al., *FEBS Lett.*, 129, 322–327 (1981)). All purification fractions through the Blue Sepharose step contained both ACCase I and II polypeptides. Rapid extraction of leaves in buffer containing five additional protease inhibitors, or a 4 hour incubation of extracts at 25° C., had little or no effect on the relative amounts of the two polypeptides, suggesting that ACCase II is not a breakdown product of ACCase I.

Antiserum to ACCase I strongly recognized the ACCase I polypeptide in crude extracts and showed little or no recognition of ACCase II polypeptides. No bands were recognized by preimmune serum. Assuming that avidin binds similarly to ACCase I and II polypeptides, it appears that the amount of ACCase II on the Western blot was slightly less than the amount of ACCase I. However, the relative staining with antibody compared to avidin indicated that the antibody had significantly less affinity for ACCase II than ACCase I.

To determine whether the same ACCase polypeptides were expressed in different maize cell types, proteins in mesophyll chloroplasts and crude extracts of leaves, endosperm tissue, embryos, and BMS cells were separated by SDS-PAGE. All preparations contained a predominant biotinylated polypeptide of approximately 227 kD (ACCase I) that was strongly recognized by ACCase antiserum or avidin. Similar 227 kD band densities were observed when gel lanes were probed with either avidin or ACCase antiserum. The 219 kD ACCase II polypeptide was readily detected in leaves only by avidin binding, but was in low abundance or not detected in extracts from other tissues. Only the 227 kD ACCase I polypeptide was detected in purified mesophyll chloroplasts, however, suggesting that the 219 kD ACCase II polypeptide is localized elsewhere in mesophyll cells or in other cell types of young leaves. ACCase activity and a >212 kD biotinylated polypeptide(s) were also found in bundle sheath strand extracts, but low yields prevented us from determining the type of ACCase present. Two other major biotinylated polypeptides of 75 and 74 kD were found in all tissues. Other non-biotinylated proteins of 66 kD (faint) and 55 kD were also recognized by ACCase antiserum. The 55 kD polypeptide was only found in leaves; it was also present in both ACCase I and II Mono Q fractions (FIG. 5) and was identified as the Rubisco large subunit based on its comigration with protein immunoprecipitated bN, spinach Rubisco antiserum.

Figure 6:
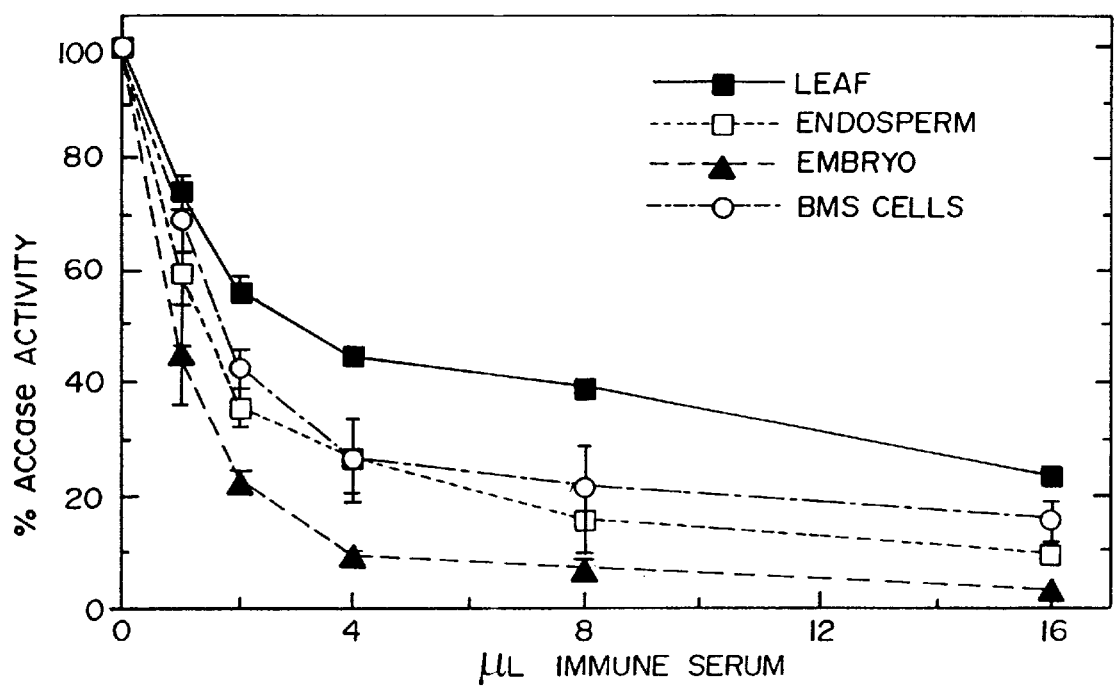
FIG. 6: Immunoprecipitation of ACCase activity from B73 leaf, embryo, endosperm, and BMS suspension cultured cells. Equal activities (0.58 nmol $min^{-1}$) were incubated with 16 µL serum (immune plus preimmune), immune complexes were precipitated with Protein A-agarose, and ACCase activity remaining in the resulting supernatant fraction was measured relative to the preimmune serum control.

ACCase antiserum immunoprecipitated at least 75% of ACCase activity from crude, desalted extracts of leaves endosperm tissue, embryos, and BMS cells (FIG. 6), indicating that most of the ACCase activity in these tissues is immunologically related to the ACCase I polypeptide of leaves. Less activity was precipitated from leaves (75%) than from other tissues, particularly embryos (98%). Compared to immunoprecipitation, inhibition of ACCase activity by antiserum in solution was less than 20% as effective in reducing ACCase activity.

The substrate specificity of ACCase from different purification fractions was examined to compare [$^{14}$C]HCO$_3$- incorporation in the presence of different acyl-CoA substrates. Both ACCase I and II utilized propionyl-Co-A 40 to 50% as rapidly as acetyl-CoA at 50 to 500 $\mu$M substrate even though they contained no biotinylated polypeptides (FIG. 5) the size of known propionyl CoA carboxylases (70 to 75 kD; see E. S. Wurtele et al., *Archives of Biochemistry and Biophysics*, 278, 179–186 (1990)). Activities in the presence of both acetyl-CoA and propionyl-CoA (250 or 500 $\mu$M each) were approximately 90 (ACCase I) to 130% (ACCase II) that of 500 $\mu$M acetyl-CoA alone. Crude leaf extracts utilized propionyl-CoA and methylcrotonyl-CoA 60% as efficiently as acetyl-CoA. Methylcrotonyl CoA carboxylase activity was reduced 85% by gel filtration and was completely removed by Blue Sepharose affinity chromatography.

Figure 7:
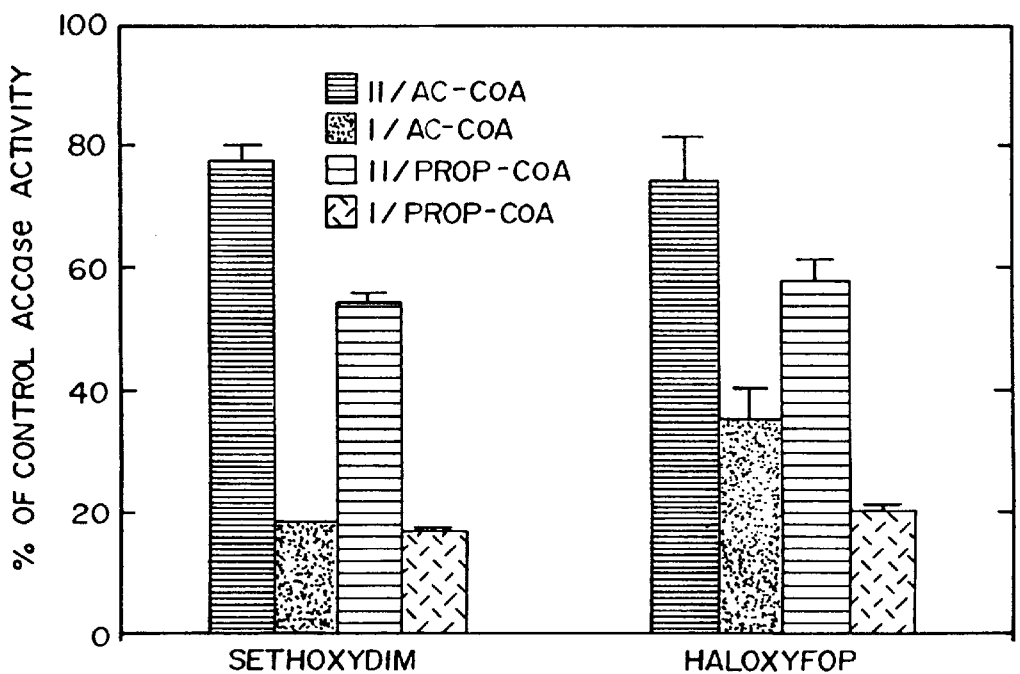
FIG. 7: Herbicide inhibition of acetyl-(AcCoA) or propionyl-CoA (Prop-CoA)-dependent $H^{14}CO_3$-incorporation into acid-stable product by ACCase I and II Mono-Q fractions. Activities in the presence of haloxyfop (1 µM) are expressed relative to the minus herbicide control.

ACCase I and II differed significantly in their inhibition by either haloxyfop or sethoxydim (FIG. 7). Acetyl-CoA or propionyl-CoA-dependent H$^{14}$CO$_3$- incorporation by ACCase I was strongly inhibited (65 to 80%) by 1 $\mu$M haloxyfop or 10 $\mu$M sethoxydim, while ACCase II activity was inhibited less than 50% for all herbicide/substrate combinations examined.

C. Cloning and Identification of Maize cDNA Clones Encoding ACCase

Maize cDNA clones encoding a portion of the ACCase game were identified by screening a DNA library generated from maize. The cDNA clones were used to identify the sequence of the ACCase gene and to identify the genomic DNA fragments encoding the gene or genes for ACCase.

A $\lambda$gt11 cDNA library from maize inbred A188 seedlings was prepared by standard method for oligo-dT priming, as described for pea cDNA. (Gantt and Key, *Eur. J. Biochem.*, 166:119–1125 (1987). Plaque lifts of the maize cDNA library were screened with maize ACCase antiserum (Egli et al., *Plant Physiol.*, 101, 499 (1993)) to identify plaques expressing ACCase-like proteins as described by Sambrook et al., cited supra. (1989). The initial screen of 800,000 plaques yielded 120 positives. Rescreening and plaque purification reduced the number of positives to 14. All 14 clones bound ACCase antibodies that, when eluted from plaque lifts (J. Hammarback et al., *J. Biol. Chem.*, 265:12763 (1990)), recognized a 227-kD biotinylated polypeptide on SDS-PAGE western blots of embryo and leaf crude extracts. The strongest western blot reaction was obtained with cDNA clone #15-14. The six best clones were digested with EcoRI to excise maize cDNA inserts. Total insert sizes ranged from 1.2 to 5.1 kb indicating the clones most likely did not contain the full coding sequences for the mature 219-kD and 227-kD ACCase polypeptides (minimum estimates of 6.1 and 6.3 kb, respectively).

Figure 8:
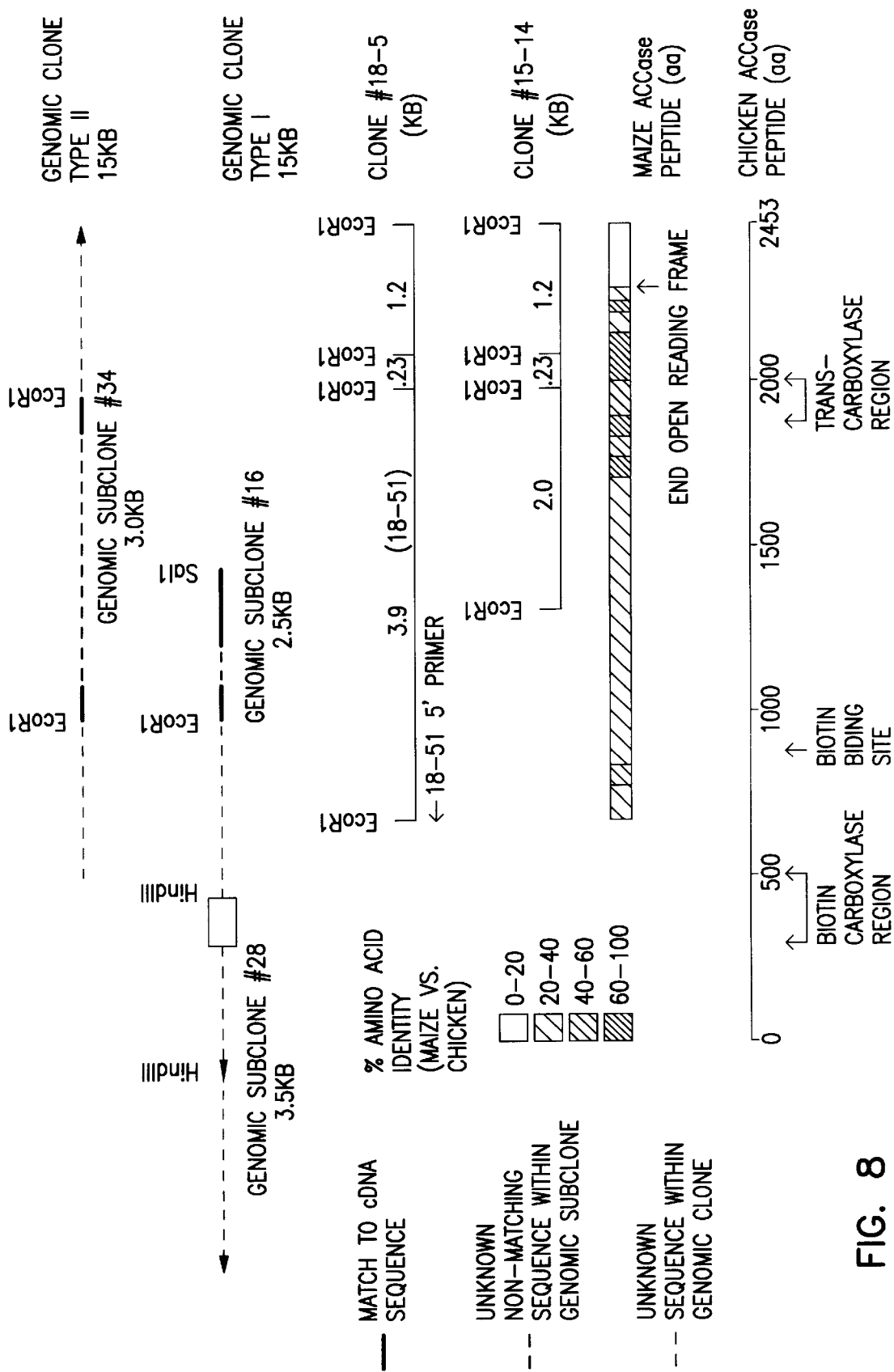
FIG. 8: Comparison of the peptide sequence of maize cDNA clones #15-14 and #18-5 with chicken ACCase. The approximate locations of the biotin carboxylase, biotin binding site, and biotin transcarboxylase functional domains are indicated for the chicken sequence. The percentages of amino acid identity are indicated by cross-hatched boxes for the maize coding sequence. Regions of genomic DNA Type I and Type 11 clone sequences that align with cDNA #18-5 are indicated by solid heavy lines. The approximate locations of subclone #28 and #16 from genomic Type I and subclone #34 from genomic Type II clones are indicated.
Figure 9:
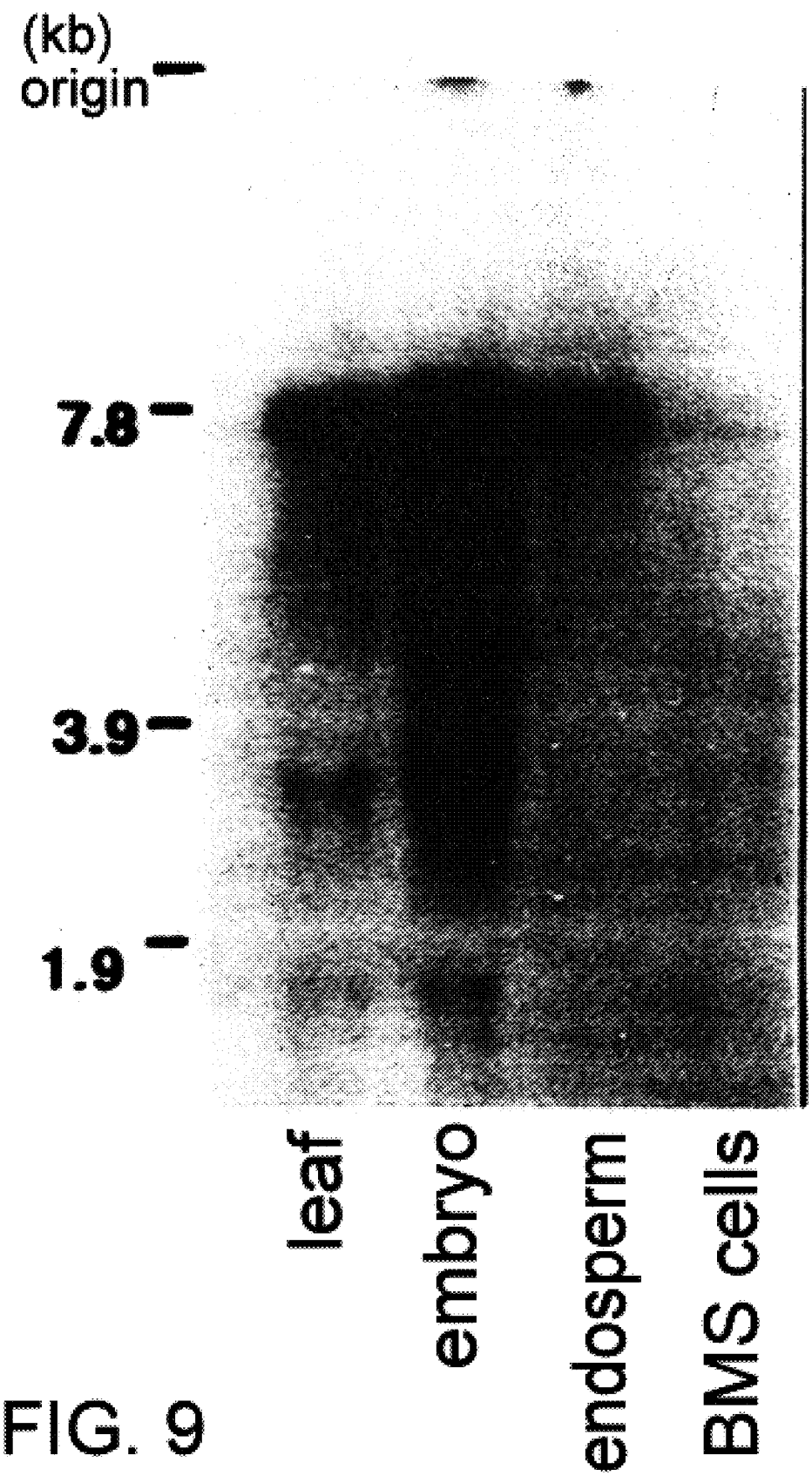
FIG. 9: Northern blot of total RNA from leaf, immature embryo and endosperm tissue (16 days after pollination), and Black Mexican Sweet corn (BMS) cells. Lanes contain 10 μg total RNA and were probed with the 2 kb EcoRI fragment of lambda clone #15-14.

Clone #15-14 contained three EcoRI fragments of 2.0, 1.2 and 0.23 kb shown in FIG. 8. Southern blots showed that the 1.2 and 2.0-kb fragments of clone #15-14 each hybridized to different fragments in the other five clones, with the exception of clone #4-4 which only contained a 1.2-kb fragment. The six maize cDNA clones contained EcoRI fragments that hybridized to a large transcript (ca. 7.8 kb) on Northern blots of total RNA from maize leaves, embryos and endosperm (FIG. 9). BMS cell culture RNA also contained a 7.8 kb transcript, but the hybridization signal is not evident on this exposure (FIG. 9). The relative abundance of the 7.8-kb transcript in embryos was higher than the other sources which is consistent with their ACCase activity.

The three EcoRI fragments were subcloned from cDNA clone #15-14 into BlueScript vector and sequenced by the dideoxy chain termination method (Sequenase 2.0 USB) initially using T3 and T7 primers and then oligonucleotide primers based on insert sequence. A clone #16-6 was also sequenced in a similar manner. Clone #16-6 included three EcoRI fragments of 3.1 kb, 1.2 kb, and 0.23 kb and had additional sequence located upstream from that of clone #15-14. After comparing the sequence and determining that the sequence was the same, the additional 1.2 kb sequence at the 5' end was sequenced.

Clone #18-5 was sequenced in a similar manner. Clone #18-5 included 3.9 kb, 1.2 kb, and 0.23 kb EcoRI fragments and contains an additional 1.9 kb 5' sequence upstream from clone #15-14. Subclone #18-5I (3.9 kb EcoRI fragment) has been deposited with the American Type Culture Collection and given Accession No. 69236.

GenBank, PIR-29, and Swiss-Prot 19 data banks have been searched for amino acid homology with the corresponding amino acid sequences of the three subclones of clone #18-5. Peptide sequences corresponding to the maize cDNA subclones had higher similarity to chicken, rat, and yeast ACCases than to any other peptide sequence in the data banks. FIG. 8 illustrates the relative organization of the 3.9, 1.2 and 0.23-kb EcoRI fragments of clone #18-5 and their co-linearity and extent of amino acid identity with chicken ACCase cDNA sequence. This comparison shows that the maize clone #18-5 has a large region near the 3' end with high amino acid identity (40 to 61%) to chicken ACCase, a longer region with 23% identity in the middle of the 3.9-kb sequence, and a short region with 52% identify near the 5' of the 3.9 kb sequence.

Portions of the sequence of the #18-5I subclone have been identified as encoding domains of the ACCase enzyme of functional significance. Those functional regions include a fragment that spans the presumed transcarboxylase active site in the enzyme having the following presumed sequence SEQ ID NO:2:

```
       1112-856
GTT CCT GCA AAC ATT GGT GGA CCT CTT CCT ATT ACC AAA CCT CTG GAC

CCT CCA GAC AGA CCT GTT GCT TAC ATC CCT GAG AAC ACA TGC GAT CCA

CGT GCA GCT ATC TGT GGT GTA GAT GAC AGC CAA GGG AAA TGG TTG GGT

GGT ATG TTT GAC AAA GAC AGC TTT GTG GAG ACA TTT GAA GGA TGG GCA

AAA ACA GTG GTT ACT GGC AGA GCA AAG CTT GGA GGA ATT CCT GTG GGC

GTC ATA GCT GTG GAG ACA
```

This functional domain is contained in the sequence 1112 to 856 base pair from the 3' stop codon or carboxy terminus region of the ACCase coding sequence of maize. This transcarboxylase active sequence is also present in clone #15-14.

Another functional region that has been identified spans the 12 base pair sequence encoding the biotin binding site having the following peptide sequence SEQ ID NO:3:

```
        5' GTT ATG AAG ATG 3'
           Val Met Lys Met
```

The biotin binding site is encoded approximately 30% in from the 5' (N-terminus) end of rat, chicken and yeast ACCase genes. These functional domains are useful in mapping and further identifying other cDNA and/or genomic fragments encoding ACCase genes.

The cDNA clones encoding portions of the acetyl CoA carboxylase genes are useful to identify the sequence of the gene or genes and are useful as probes to locate the genomic copies of the gene or genes. Because the ACCase antibodies used to screen the λgt11 library recognize both the 219 and 227 kD ACCase polypeptides, it has not been determined which polypeptide is encoded by these less than full length clones. It is likely that the majority of the clones encode the 227 kD polypeptide since that polypeptide is more abundant in the leaf tissue source of the DNA library and the antibodies have a higher affinity for the 227 kD ACCase polypeptide.

EXAMPLE VI

Isolation and Sequencing of Genomic Encoded ACCase Genes and a Complete cDNA Sequence of a Maize ACCase Gene The maize genome has been analyzed to identify copy number and location of the genomic copies of ACCase gene or genes. Four distinct types of maize ACCase genomic clones have been identified, termed A1, A2, B1 and B2 (see below).

To obtain genomic copies of ACCase genes, a maize B73 genomic library (Clontech, Palo Alto, Calif.) was screened with the 2 kb subclone from #15-14 and several clones of about 15 kb were identified as having homology to the ACCase cDNA. Restriction mapping and partial sequence analysis revealed two types of genomic clones (Type A and Type B) that differed in restriction sites and in their position relative to the ACCase partial cDNA sequence as shown in FIG. 8.

The 2.5 kb EcoRI-SalI fragment (#16) from the Type A genomic clone and the 3.0 kb EcoRI-EcoRI fragment (#34) from the Type B genomic clone were shown to hybridize to the 3.9 kb probe from #18-5 and were subcloned into the Bluescript vector and sequenced. Approximately 1.5 kb of DNA sequence from the genomic Type A 2.5 kb fragment were 100% identical to coding sequence from the 3.9 kb cDNA subclone #18-5I described in Example V; the remaining sequence exhibited no identity with the cDNA clone and presumably represents a noncoding intron sequence. A 350 nucleotide sequence derived from the genomic Type B 3.0 kb fragment was about 95% identical to the cDNA clone indicating that its coding sequence differs from that of genomic Type A. These results also indicate that the maize genome encodes at least two different genes encoding a polypeptide having acetyl CoA carboxylase activity.

To identify and clone the remainder of the gene representing the amino-terminus of maize ACCase, additional regions from the Type A genomic clone have been subcloned and partly sequenced. The 3.5 kb HindIII—HindIII fragment (#28) has been sequenced for about 400 nucleotides from each end. The 3' end of #28 shows significant homology to the amino acid sequence from the chicken sequence located about 0.5 kb from the start of the chicken gene.

The complete sequence for fragment #28 can be obtained and analyzed to determine whether it contains the 5' end of the ACCase coding region. The start of the transcribed region, and thus the likely start of the coding region for ACCase, can be identified by using the genomic clones in RNAse protection analysis (J. Sambrook et al., "Molecular Cloning—A Laboratory Manual," Cold Spring Harbor Press, Cold Spring Harbor, N.Y. (1989)). Based on sequence data from the genomic clone, alignment, as shown in FIG. 8, with sequences of other ACCases and identification of potential open reading frames, oligonucleotide primers can be constructed to synthesize cDNA molecules representing the amino terminus of the ACCase gene. These molecules can be hybridized to genomic Type A DNA fragments such as #28 and the nonhybridizing portions digested with S1 nuclease. The end of the protected fragment are determined by analysis on a DNA sequencing gel.

To synthesize the remaining coding region between the end of the cDNA clone #18-5 and the start of transcription, two oligonucleotide primers were synthesized. Primer I is complementary to the DNA sequence: (SEQ ID NO:4)

5' GCCAGATTCC ACCAAAGCAT ATATCC 3'
near the 5' end of cDNA subclone #18-5I and can be used as a primer for synthesis of cDNA molecules from maize seedling, leaf or embryo RNA.

A primer corresponding to a DNA sequence near the transcription start site can be used in combination with primer 1 for the amplification of DNA by the polymerase chain reaction (PCR). Several independent clones are then sequenced and their sequences compared to the known sequence of the Type A genomic clone to determine the exact coding sequence corresponding to that maize gene for ACCase. A similar strategy can be used to obtain the complete coding sequence for genomic Type B ACCase.

The remaining cDNA sequence was obtained by three successive rounds of RT-PCR using oligonucleotide primers based on genomic apparent exon (5') and known cDNA (3') sequences. The primers used to amplify nucleotides 1–240 of the cDNA were 28sst-a5+ (SEQ ID NO. 7) and 28sst-6at3+ (SEQ ID NO:8), nucleotides 217–610 of the cDNA were 28sst-5+(SEQ ID NO:9) and 28-2t3+(SEQ ID NO:10) and nucleotides 537–2094 of the cDNA were ACCPCR5' (SEQ ID NO:11) and 155-(SEQ ID NO:4) (Table V). PCR products corresponding to nucleotides 1–240, 217–610. and 537–2094 of the final sequence were cloned into PCR-script (Stratagene).

1952–1961), and carboxybiotin (amino acids 1662–1711) were highly conserved among all MF ACCases.

EXAMPLE VII

Characterization of other Genomic Clones

The initial restriction fragment length polymorphism (RFLP) analysis of EcoRI-digested total DNA from three maize inbred lines showed one band when probed with the 2 kb subclone from #15-14 (internal to gene) and two bands when probed with the 1.2 kb subclone (near the 3' end of the gene). Fragments homologous to the 2 kb probe were

TABLE V

| cDNA Position | 5' primer designation | 5' primer sequence | 3' primer designation | 3' primer sequence |
|---|---|---|---|---|
| nt-1–240 | 28sst-a5+ | GGTCTTCAATTGTGCTGTCTGG (SEQ ID NO:7) | 28sst-6at3+ | CCTTGACGAACAGACTGGCTGTGC (SEQ ID NO:8) |
| nt 217–610 | 28sst-5+ | CACAGCCAGTCTGTTCGTCAAGG (SEQ ID NO:9) | 28-2t3+ | CCTCTACGTAATTGGTCAGC (SEQ ID NO: 10) |
| nt 537–2094 | ACCPCR5' | CATAGCTATGGCAACTCCGG (SEQ ID NO:11) | I55 | GGATATATGCTTTGGTGGAATCTGGC (SEQ ID NO:4) |

The original 5.4-kb cDNA clone #18-5 and PCR products from at least three individual PCR per oligonucleotide pair were sequenced in both directions by the dideoxy chain-termination method, using either Sequenase II (U.S. Biochemicals) or ABI 373 (Applied Biosystems, Inc.) protocols. No sequence differences were found in regions of clone overlaps. The complete sequence of the cDNA of maize ACCase (nucleotides 1–7470 SEQ ID NO:5) and its corresponding amino acid sequence (amino acids 1–2325 SEQ ID NO:6) are shown in FIGS. 13 and 14. The 7470 bp cDNA includes a 459 nucleotide 3' untranslated region and 36 nucleotides of 5' untranslated sequences.

The first Met codon in the cDNA (nucleotides 37–39) was identified as the start codon based on its similarity to consensus initiation sequences (Kozak, *J. Cell. Biol.,* 108, 229 (1989); Lutcke et al., *Embo. J.,* 6, 43 (1987)). An in-frame stop was found in the genomic sequence 6 nucleotides upstream of the sequenced cDNA, and RT-PCR analysis of this region suggested that the in frame stop codon was also present in the cDNA. The 3' end of the coding sequence was defined by two stop codons present in the large open reading frame after nucleotide 7011. The translated coding sequence predicted a polypeptide of 2325 amino acids (257 kD; SEQ ID NO:6) which was 79 to 81% identical to the multifunctional (MF) ACCases from alfalfa (Shorrosh et al., *Proc. Nat'l. Acad. Sci.,* 91, 4323 (1994)) and wheat (Gornicki et al. *Proc. Nat'l Acad. Sci.,* 91, 6860 (1994)), and to a 118-amino acid predicted polypeptide of a rice expressed sequence tag (Genbank accession #D39099, T. Sasaki), but only 53 to 55% identical to ACCase from other eukaryotes.

In a pileup alignment of plant ACCases (Genetics Computer Group. Madison, Wis.), Met I of both maize and *Brassica napus* ACCases was located about 130 amino acids upstream of the conserved sequence VDEFCKALGG, compared to only 25 amino acids upstream for other plant ACCases. The predicted 2325 amino acids of maize ACCase contains a biotinylation site at position 806, within the conserved MKM motif (Ton et al., *Eur. J. Biochem.,* 215, 687 (1993)). The arrangement and amino acid sequence of binding sites (Shorrosh et al., *Proc. Nat'l. Acad. Sci.,* 91, 4323 (1994)) for ATP (amino acids 318–333), biotin (amino acids 799–811; biotin at 806), acetyl-CoA (amino acids monomorphic and the more intense of the two bands hybridizing with the 1.2 kb probe was dimorphic. As discussed in Example V, these results support the view that maize contains at least two distinguishable ACCase genes and that they may be quite similar for much of the coding region. Additional genomic Southern blots of a set of recombinant inbred lines were used to map polymorphisms for the ACCase probes to maize chromosomes. One polymorphism was mapped to the short arm of chromosome 2: other polymorphisms were not evident in these initial tests to identify a chromosomal location for other maize ACCase genes.

The isolation and restriction mapping of additional genomic clones from a B73 genomic library (Clontech) resulted in the identification of four different types of clones termed A1, A2, B1 and B2 (FIGS. 16–19) which had 96% nucleotide sequence identity. Types A and B correspond to previously published pA3 and pA4 cDNAs (Ashton et al., *Plant Mol. Biol.,* 24, 35 (1994)) and differ from pA3 and pA4 by 4% in their coding sequences.

Type A and B genomic clones have linear sequence homology except for an insertion in an intron of the Type B genes about 1400 bp 3 ' of the A1 (SEQ ID NO:5) translation start site. Analysis of the insert boundaries revealed a 3-bp target site duplication and a 6-bp direct repeat, and further sequence analysis showed the presence of two new and unique LINE elements (Long Interspersed Nuclear Elements) in B1 and B2. Mammalian LINE elements are highly abundant ($10^4$ to $10^5$ copies), 6 to 7 kb long, and have frequent 5 '-end deletions and an A-rich 3' terminus. They are flanked by short direct repeats, and contain two ORFs, one encoding a reverse transcriptase. Three LINE elements (Cin4, 50-100 copies in maize; del2, 250,000 copies in lily; BNR1, 2–5% of genome in sugarbeet) have been described in plants (Leeton et al., *Mol. Gen. Geneti.,* 237, 97 (1993); Schmidt et al., *Chromo. Res.,* 3, 335 (1995); Schwarz-Sommer et al., *EMBO J.,* 6, 3873 (1987)). Maize ACCase B1 has one unique LINE element and B2 has two. The two B2 LINE elements were characterized by differences in their reverse transcriptase sequence. The B genomic clone inserts have characteristic LINE features including cysteine motifs and a possible polyA tail, and high abundance. The LINE insert also has been found in an intron of the maize Shrunken-2 gene (Hannah et al., *Plant Physiol.*, 98, 1214 (1992)).

The partial nucleotide sequence (3489 nucleotide) of a Type A1 ACCase genomic clone is shown in FIG. 16 (SEQ ID NO:12). The clone is a HindIII fragment which includes nucleotides 1–931 of the cDNA in FIG. 13 (SEQ ID NO:5), and the first four introns within the coding region, at positions 240 (460 nucleotides), 296 (480 nucleotides), and 872 (76 nucleotides) of SEQ ID NO:5. The clone also has 1395 nucleotides 5' to the cDNA of SEQ ID NO:5 (i.e., 1431 nucleotides 5' of the translational start at nucleotide position 1432).

The partial nucleotide sequence (1328 nucleotide) of another Type A clone is shown in FIG. 17 (SEQ ID NO:1 ). The partial sequence is all 5' untranslated sequence and contains a 7 base insert between nucleotides 279–290, but is otherwise identical to SEQ ID NO:12.

The partial nucleotide sequence of six Type A2 clones is shown in FIG. 18 (1565, 1168, 638, 558, 976 and 852 nucleotides; SEQ ID NOs 14, 15, 16, 17. 18 and 19, respectively).

Within the A1–A2 clone pair, identified differences are in introns and 5' UTR sequences. The A2 genomic clone is weakly amplified with Type A1 PCR primers specific for the 5' UTR if the 3' primer employed is for a conserved amino acid sequence found in all ACCases (e.g., 28sst-110F, ACTGTGCGTTTGAGAAGGTC, SEQ ID NO:23, and 28sst-2T3+, CCTCTACGTAATTGGTCAGC, SEQ ID NO:24). The A2 amplified product is the same size as that from the Type A1 genomic clone, and restriction analysis indicated a difference in sequence from A1. Sequence differences in the 5' region should provide a means to distinguish between expression of A1 and A2 ACCase genes and to determine whether A2 also encodes a CTP.

The partial nucleotide sequence (231, 207 and 180 nucleotides) of three Type B clones is shown in FIG. 19 (SEQ ID NOs 20. 21 and 22, respectively).

The cDNAs corresponding to genomic clones A2, B1 and B2 are cloned and sequenced in a manner similar to that described above. The derived amino acid sequences are aligned with known ACCase sequences. If putative CTP sequences are identified, functionality is tested as described below. Also if the tissue specificity and developmental timing of expression differ for different ACCase genes, the sequences of the promoter regions of the corresponding genomic clones are compared. Gene-specific probes for specific ACCase genes can provide more information on their roles in lipid synthesis (plastid and cytoplasmic isoforms), secondary metabolism (cytoplasmic isoforms), and herbicide resistance (likely plastid isoforms).

A 3' Type A1 ACCase cDNA probe mapped to chromosome 2S (Egli et al., *Maize Genetics Newsletter*, 68, 92 (1994)) and to 10 L (Caffrey et al., Maize Gen. Coop., 69, 3 (1995)). Two 5' Type A1 cDNA probes which span the transit peptide mapped to chromosome 2S in the same location as the 3' probe (see maize genetic map, 1996 version, Maize Genomic Database). PCR primers 28sst-97F (CCTTTTTATGGCACTGTGCG, SEQ ID NO:25) and 28sst-6t3+; (CATCGTAGCCTATATGAGGACG, SEQ ID NO:26) located in non-coding regions of A1 that span the chloroplast transit peptide were used to amplify a B73 chromosome-specific product which segregated with the resistance trait. A nearby 5' primer (28sst-a5+, SEQ ID NO:7) amplified all genotypes and functioned as a positive control. Herbicide resistance due to the Acc1-S3 mutation segregates (29/29 individuals to date) with production of a Type A 5' end-specific PCR product derived from the mutant parent while herbicide sensitive plants lack the transit sequence (15/17 progeny). Two individual plants which contained B73-specific DNA at this location died of unknown causes while grown in the presence of herbicide.

Mutations in maize that confer resistance to cyclohexanedione and aryloxyphenoxypropionate herbicides by means of an altered ACCase target are found at two non-allelic loci, Acc1 and Acc2. A1 and A2 appear to encode plastidic ACCases and correspond to the Acc1 and Acc2 herbicide resistance loci. Acc2 has been mapped to 10 L (VanDee, M. S. Thesis, University of Minnesota (1994)). Acc1 is the site of five allelic mutations including Acc1-S2 and -S3 (Marshall et al., *Theor. Appl. Genet.*, 83, 435 (1992)), and has been mapped to chromosome 2.

Only one plastidic ACCase polypeptide was identified by SDS-PAGE of maize leaf extracts, although 2-D gel analyses might provide evidence for a second, highly similar isoform. Of the two ACCase isoforms, only ACCase I shows altered herbicide inhibition in Acc1-S2 mutants, and most of the ACCase activity in leaves and developing embryos is herbicide-resistant and thus attributed to the Acc1-S2 gene product.

Although a 3' ACCase probe has been mapped both to 10 L near Acc2-S5 and to 2S, the conserved sequence of ACCase genes and lack of polymorphism in multiple bands complicates identification of genes encoded at these loci. The Type A1 ACCase gene is probably located on chromosome 2, since (i) 5' untranslated and chloroplast transit peptide probes from Type A1 hybridize to two bands (dark and light) in maize inbreds, and (ii) analysis of maize-oat addition lines carrying maize chromosomes 2 through 9 indicates the dark band is on chromosome 2 and the light band is on chromosome 1 or 10.

Type B ACCase genes are likely to encode cytosolic isoforms. Given that cytosolic malonyl-CoA is a precursor in the synthesis of many secondary metabolites including flavonoids (e.g., maysin, a corn silk component associated with corn earworm resistance), these cytosolic ACCases can have agronomic utility.

Northern blot analysis of total maize RNA with an ACCase probe (nucleotides 3400–5932) showed a single 8.3 kilobase band. To determine whether the expression of ACCase RNAs was developmentally regulated, blots of total RNA from 16 to 42 DAP (days after pollination) embryos were probed with an ACCase cDNA fragment. Transcript abundance peaked about 23 DAP and the steady state pattern was similar to in vitro ACCase enzyme activities and protein measured from developing embryos. Type A- and B- specific $^{32}$P-CTP-labeled antisense transcripts were 780 nt long (662 nt of ACCase sequence+118 nt of vector/promoter sequence) and were identical except for 15 base mismatches scattered along their length. Each antisense transcript was hybridized to total RNA from embryos at 16, 20, 23, and 42 DAP and digested with RNAse A/TI mixture to yield a 662-base fragment specific to the probe used. The results showed that the Type A transcript was more abundant than Type B at all tested stages, and that only Type A remained high in older embryos. Types A and B had similar expression patterns and peaked around 20–23 DAP. The ratio of Type A:B mRNA in leaves was about 2: 1, similar to its relative abundance in cDNA expression libraries.

EXAMPLE VIII

Expression of the Maize ACCase Chloroplast Transit Peptide

The N-terminus of the predicted maize ACCase polypeptide is longer than that of predicted cytosolic ACCase isoforms and has several characteristics typical of chloroplast transit peptides within the first approximately 73 amino acids of the predicted N-terminal sequence. The CTP cleavage site motif is not found in the putative maize ACCase CTP, although only about 30% of known CTPs contain this consensus sequence (Gavel and von Hejne, *FEBS Lett.,* 261, 455 (1990)). However, the maize ACCase N-terminus appears to have several other properties typical of known CTPs: (1) a lack of acidic residues in amino acids 1–49, (2) high Ser+Thr content (69% within amino acid residues 23–35), (3) an R-rich region between S- and D-rich regions in amino acid residues 36–49, and (4) a predicted turn→β sheet within amino acid residues 58–73 (von Hejne and Nishikawa, *FEBS Lett.,* 278, 1(1991)).

The ability of the amino acid sequence contained within the N-terminal 100 amino acids of the translated maize acetyl-CoA carboxylase (ACCase) cDNA to direct the N-terminal portion of the maize ACCase biotin carboxylase domain into chloroplasts was tested in vitro by methods used extensively in the literature (see Cline et al., *J. Biol. Chem.,* 260, 3691 (1985); Lubben and Keegstra, *Proc. Nat'l. Acad. Sci.,* 83, 5502 (1986)). The criteria for import was that (1) in vitro-synthesized, $^{35}$S-labeled protein was imported into chloroplasts, and (2) the transported protein was smaller than the original translation product, by an amount which corresponds to the removal of the expected CTP. Import studies utilized either maize or pea chloroplasts. Pea chloroplasts have been reported to correctly import proteins from many different species, including maize (Nieto-Sotelo et al. *Plant Physiol.,* 93. 1321 (1990)). Alternatively, the function of the putative maize ACCase CTP is tested by inserting the first 258 coding nucleotides of maize ACCase in frame with and 5' of a GUS reporter gene in pBI221 (Clontech). This construct and the pBAR plasmid are used to co-transform maize "Black Mexican Sweet" suspension cells by particle bombardment. Basta-resistant transformants are selectedm and GUS activity and/or protein is assayed in surviving cultures or in plasmids isolated from transformants.

A partial ACCase construct consisting of nucleotides 1–833 of SEQ ID NO:5 including the putative CTP (nucleotides 37 to 256) and the first domain within the biotin carboxylase region (identified by amino acid sequence comparison with *E. coli* biotin carboxylase; see Waldrop et al. *Biochem.,* 33, 6249 (1994)) was amplified by PCR and cloned into the EcoRV site of PCR-script (Stratagene) to create the plasmid pBCN1. A corresponding plasmid lacking CTP sequences (nucleotides 278–833) was also made (-pBCN1). The protein encoded by -pBCN1 begins at amino acid residue 83 (Val—Met).

Constructs were transformed into *E. coli* SURE cells (Stratagene).

Restriction analysis of pBCN1 with BamHI and HindIII indicated that the 5' end of the ACCase was located adjacent to the T7 RNA polymerase binding site in PCR-Script. A partial sequence of pBCN1 obtained by using the T7 sequencing primer and the ABI373 automated sequencing protocol confirmed this orientation and showed that the pBCN1 insert sequence was identical to maize ACCase cDNA for at least the first 300 nucleotides and that it included the maize ACCase Met 1 ATG. An acyl carrier protein clone containing a CTP (spinach ACPII, a gift of Dr. John Ohlrogge, Michigan State University) can be used as a positive control. These constructs are used for in vitro transcription, translation, chloroplast import, and SDS-PAGE analysis of products in the same manner as pBCN1.

Purified pBCN1 was digested with EcoRI to linearize the plasmid at the 3' end of the BCN1 insert, electrophoresed in 1.5% agarose, and the plasmid band at approximately 3.8 kb was excised and Gene-Cleaned (BioLab 101). The purified band was digested with 20 µg proteinase K to remove any residual RNAse, extracted with phenol and then chloroform under RNAse-free conditions. DNA content was estimated by ethidium bromide fluorescence in droplets, relative to λDNA standards (Sambrook et al., *Molecular Cloning: A Laboratory Manual,* 2nd ed. (1989). One pg of pBCN1 DNA was transcribed into capped RNA with the T7/mMessage mMachine kit (Ambion). Uncapped transcripts (Sp6 RNA polymerase; Promega) of pea RUBISCO small subunit (SSU; Anderson et al., *Biochem. J.,* 240, 709 (1986)) were also transcribed. RNA yield was estimated by determining the % incorporation of a $^{32}$P-ATP (Amersham) into a precipitable product, according to the Ambion kit instructions. Electrophoresis and autoradiography of $^{32}$P-labeled product showed that it contained a single RNA band of approximately 895 nucleotides, as expected.

The RNA transcripts were translated into $^{35}$S-labeled polypeptides with Ambion's wheat germ IVT kit and approximately 45 µCi $^{35}$S-methionine (Amersham; 37 TBq/mmol) in a 50-µL reaction. Labeled proteins were held on ice 6 hours prior to their use in chloroplast import experiments.

Pea (cv. "Little Marvel") and maize (inbred A188) plants were grown in a growth chamber at 25° C., 16 hour day length. Chloroplasts were isolated from pea and maize leaves 7 days after planting, respectively, as previously described (Burton et al., *Pestic Biochem. and Physiol.,* 34, 76 (1989); Egli et al., *Plant Physiol.,* 101, 499 (1993)). Intact mesophyll chloroplasts were washed in resuspension buffer [50 mM HEPES-KOH, pH 7.8 plus 0.33 M (pea) or 0.66M (maize) sorbitol] in preparation for import assays. Suspensions were diluted to obtain 75 µg chlorophyll/0.3 ml (Arnon, *Plant Physiol.,* 24, 1 (1949)).

Import experiments were carried out essentially as described by Cline et al.(*J. Biol. Chem.,* 260, 3691 (1985)). Import reactions containing 0.3 ml pea or maize chloroplast suspension, 40 µl $^{35}$S-translation mixture, 3 mM Mg-ATP and 10 mM Met were incubated under light for 1–30 minutes at 25° C.

Unimported proteins were digested for 30 minutes with 40 µg of thermolysin, and proteolysis was stopped with 10 mM EDTA.

Chloroplasts were re-isolated by centrifuging them through I-ml 40% v/v Percoll gradients in the presence of resuspension buffer plus 3 mM Mg-ATP, 10 mM Met, and 20 mM EDTA, washed twice in the same buffer, and resuspended in 65 µl of 1 mM MgCl$_2$/10 mM Tris buffer, pH 8.0. Chloroplasts were lysed by three cycles of freeze-thawing in liquid N$_2$, microfuged, and aliquots of the supernatants and of the original in vitro-translated proteins were analyzed by SDS-PAGE in 8–25% gradient Phast gels (Pharmacia), followed by direct detection of radiolabeled proteins in the wet gels (AMBIS) (FIG. 20).

Figure 20A:
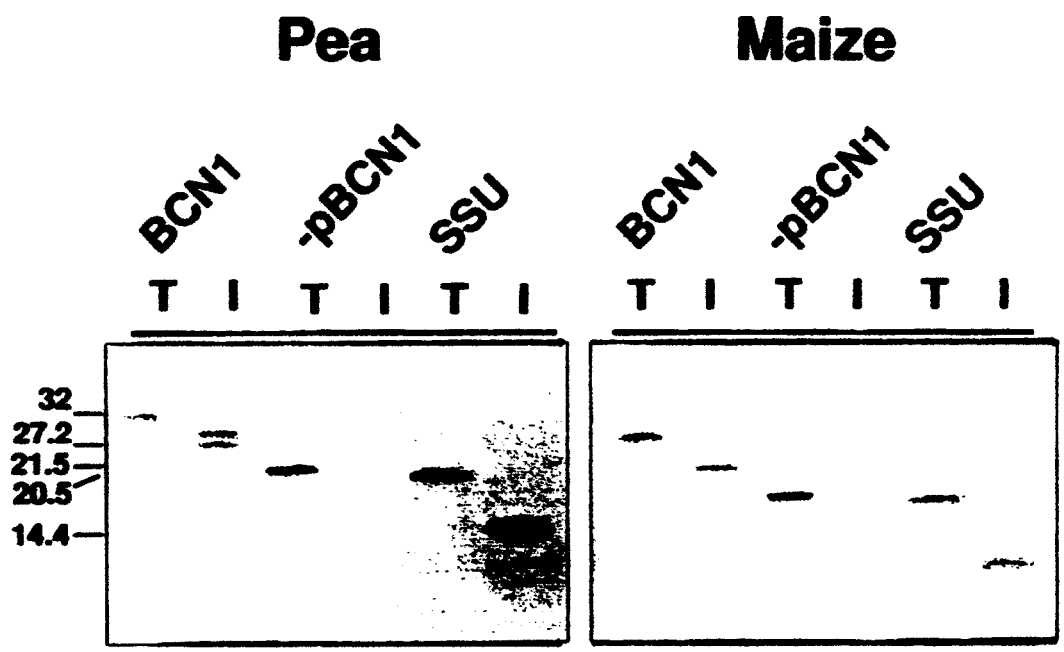
FIGS. 20A–20B: SDS/PAGE analysis of chloroplast importation of $^{35}$S-labeled ACCase polypeptides. (A) Pea and maize chloroplasts incubated with $^{35}$5-labeled ACCase polypeptides for 30 minutes. (B) A time course analysis of the importation of $^{37}$S-labeled ACCase polypeptides into maize chloroplasts.
Figure 20B:
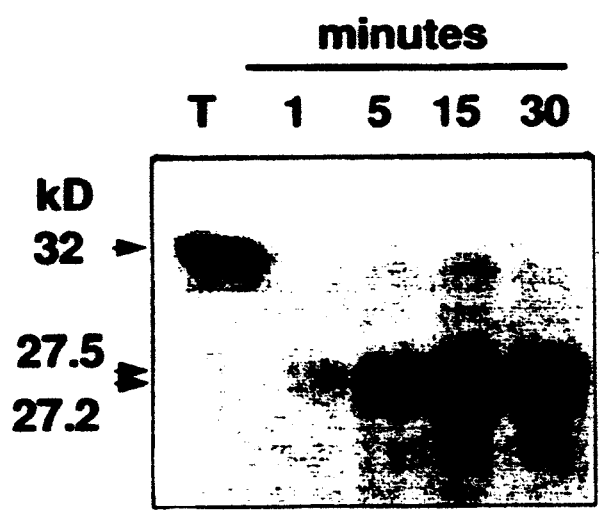

As estimated by SDS-PAGE, a 30 minute import converted the original 32-kD BCN1 polypeptide to a doublet of 27.2 and 27.5 kD in maize and produced an additional 30-kD band in pea (FIG. 20A). Neither maize or pea chloroplasts imported -pBCN1-derived polypeptides. Formation of the 27.2-kD polypeptide likely resulted from cleavage after amino acid #47–49, a likely cleavage site because it lies between S- and D-rich regions, and R residues are located at -2,-7, and -8 (S. Gavel and G. Von Heijne, *FEBS Lett.* 261, 455 (1990)).

Time-dependence of BCN1 import was further examined (1–30 minutes) (FIG. 20B) to determine if any imported polypeptides were a result of incomplete processing or proteolysis. Import was maximal after 15 minutes, but import time had no effect on the relative amounts of different-sized import products. Higher amounts of ATP (5 mM) stimulated import relative to lower amounts of ATP (<0.2 mM). The data suggest that, in maize, efficient cleavage of BCN1 occurs at two closely adjacent sites and that partially processed products are also formed during BCN1 import by pea chloroplasts. Therefore, nucleotides 1–833 of the maize ACCase gene encode a CTP.

EXAMPLE IX

Expression of a cDNA Clone or Genomic Clones Encoding the ACCase Gene

The cDNA and genomic clones encoding all or a portion of the ACCase gene can be subcloned into a known expression system and the gene products reactive with the antibodies specific for maize ACCase can be identified using a Western blot. For example, the ACCase cDNA clones are inserted into two transformation plasmids: (i) Glb1exp which contains the embryo-specific maize Globulin1 (Glb1) promoter and 3' regions (Belanger et al., *Genetics*, 129, 863 (1991)); and (ii) pAHC17 which contains the maize ubiquitin (Ubi-1) constitutive promoter and first exon and intron, and the NOS 3' terminator (Christensen et al., *Plant Mol. Biol.*, 18, 675 (1992); Toki et al., *Plant Physiol*, 100, 1503 (1992)). The 3' end of the $A_1$ cDNA has a unique Sal/I site just 3 ' of the stop codon which is used to ligate into a Sal/I site in both plasmids ahead of the construct terminator. Other cloning sites will be added as needed to the plasmids or cDNA to complete the ligation of the 5' end. The gene products can also be further characterized structurally and/or enzymatically. This will ensure that the genomic and cDNA clones that encode acetyl CoA carboxylase can be screened for promoters that provide for overproduction of the native or herbicide tolerant ACCase enzyme in plants.

For example, the 2 kb EcoRI fragment from clone #15-14 can be subcloned into a plant transformation plasmid pBI121 or pBI221 downstream from the 35S CaMV promoter and upstream from the nopaline 3' polyadenylation signal sequence, as described in Jefferson, *Plant Molec. Biol. Reptr.*, 5, 387–405 (1987). This plasmid can then be used to transform plant cells such as tobacco, Brassica and Arabidopsis cells using protoplast or biolistic transformation, as described by W. J. Gordon-Kamm et al., *Plant Cell*, 2, 603–618 (1990); M. E. Fromm et al., *Bio/Technology*, 8, 833–839 (1990); An, *Methods in Enzymology*, 153, 292 (1987); and D'Hafluin, *The Plant Cell*, 4, 1495 (1992). An increase in transient expression can be detected using quantitative Western blotting with antibodies specific for the ACCase enzymes. Polyclonal antibodies to maize ACCase most likely do not substantially crossreact with ACCase from dicots like tobacco or Arabidopsis.

Alternatively, the ACCase gene can be subcloned along with the 35S CaMV promoter into a binary Ti vector pGA482, as described in An, cited supra., which is a binary Ti vector system and can be used to transform plant cells by Agrobacterium-mediated transformation. Stably transformed plants can be generated by standard methods as described in Example III, and levels of expression of ACCase genes can be determined by quantitative Western blots, as described in Harlow and Lane, *Antibodies*, Cold Spring Harbor Laboratories (1988). The ability to monitor expression of cloned ACCase genes will permit the identification of promoters that provide for enhanced expression of the ACCase gene. The expression system can be used to screen for those promoters that enhance gene expression of the ACCase gene at least about 5 to 10-fold over the endogenous levels of ACCase produced normally in the plant cells. Because the 35S CaMV promoter is known as a strong promoter, it is likely this promoter will provide for at least a 5-fold increase in the expression of ACCase over that normally produced in the plant cell.

In addition, this expression system can be used to screen antisense DNA sequences. For example, an antisense sequence can be obtained that is complementary to an about 0.5 kb region of the maize ACCase cDNA that has high homology with a portion of the chicken ACCase gene and contains the sequence for the presumed transcarboxylase active site domain, as shown in FIG. 8. The antisense sequence could be subcloned into a pBI121 or pBI221 expression under the control of an inducible plant promoter, such as nitrite reductase promoter (Back et al., *Plant Molec. Biol.*, 17:9–18 (1991)). The ability of the antisense sequence to inhibit expression of the native ACCase gene can be evaluated in transformed cells, for example as described in Hamilton et al., *Nature*, 346:284–287 (1990).

EXAMPLE X

Identification and Cloning of the Gene From Herbicide Resistant Maize Cell Lines Herbicide resistant maize cell lines were generated as described in Examples I, II, and IV. These herbicide resistant cell lines have been shown to produce an ACCase enzyme that is less sensitive to inhibition by sethoxydim or haloxyfop. The genes encoding the herbicide resistant forms of the ACCase will be identified and cloned using standard methods as described in Sambrook et al., *Guide to Molecular Cloning: A Laboratory Manual* (1989). The genes encoding the herbicide resistant forms of ACCase can then be introduced into herbicide sensitive plant species by standard methods to confer herbicide resistance. For example, the ACCase enzyme in the maize cell line 2167-9/2160-154 S-1 is at least 100-fold less sensitive to sethoxydim than the wild-type.

DNA from the cell line or plants will be obtained and digested with EcoRI and/or other appropriate restriction enzymes, according to standard methods. The restriction enzyme digest will be separated out by agarose gel electrophoresis and probed with either the 2 kb or the 3.9 kb cDNA ACCase probe described in Example V. Fragments hybridizing to the 2 kb or 3.9 kb probe will be subcloned into a Bluescript vector and portions of the gene will be sequenced, as described in Example V, to verify that the entire ACCase gene has been isolated.

To confirm that the clone encodes the ACCase gene, it will be subcloned into the pBI121 or pBI221 expression vector, as described in Example VIII. The ACCase gene product expressed by the clone in either Black Mexican sweet corn cells or tobacco cells will be evaluated for reactivity with ACCase specific antibodies, by enzyme activity, and/or resistance of the enzyme activity to inhibition with sethoxydim and/or haloxyfop. It is likely that the cloned gene will encode an ACCase which is resistant to inhibition by sethoxydim and haloxyfop. This gene can then be introduced into an herbicide-sensitive embryogenic plant cell or an embryo, including maize cells or immature embryos, to confer herbicide resistance to that plant species upon regeneration.

The complete coding sequence encoding the herbicide resistant form of the ACCase enzyme will be cloned into a plant transformation vector such as pBI121 or pBI221 as described in Jefferson, *Plant Molec. Biol. Reporter*, 5:387–405 (1987). This vector contains the 35S CaMV constitutive promoter, the β-glucuronidase structural gene, and the nopaline synthase 3' polyadenylation signals. The β-glucuronidase gene is replaced with a cloned ACCase gene. Optionally, the cloned ACCase gene can be combined with natural or synthetically produced chloroplast transit peptide sequence from pea, as described in Keegstra & Olsen, *Ann. Rev. Plant. Physiol./Mol. Biol.* 40:471–501 (1989) and/or unique restriction sites introduced so the cloned gene can be distinguished from the endogenous maize ACCase gene. Standard methods of subcloning will be utilized as described in Sambrook et al., cited supra.

For transformation of maize cells, type II calli can be transformed using biolistic transformation, as described by W. J. Gordon-Kamm et al., *Plant Cell*, 2, 603–618 (1980); M. E. Fromm et al., *Bio/Technology*, 8, 833–839 (1990), and D. A. Walters et al., *Plant Molecular Biology*, 18, 189–200 (1992). Alternatively, type I embryogenic calli can be transformed using electroporation after mechanically or enzymatically wounding calli, as described by D'Hafluin et al., *The Plant Cell*, 4:1495 (1992). Once the cloned gene is introduced into these cells and transformants are selected, typically by antibiotic resistance, fertile transgenic maize plants can be regenerated, as described by D'Hafluin et al., cited supra. Fertile transgenic plants can be evaluated for herbicide tolerance, as described in Example III. It is likely that the fertile transgenic plants having and expressing a cloned ACCase gene as an ACCase resistant to sethoxydim and/or haloxyfop will exhibit herbicide tolerance as compared to the corresponding untransformed plant.

EXAMPLE XI

Generation of Transgenic Plants Having an Increase in Oil Content

Once identified and cloned, the gene or genes from maize acetyl CoA carboxylase can be introduced into monocot or dicot plant species, including maize, under the control of a promoter that provides for overexpression of the ACCase enzyme. The overexpression of the ACCase enzyme is likely to lead to an increase in the oil content of the plants and seeds.

Naturally occurring soybeans that have a high oil content and soybeans that have a low oil content have been identified. The acetyl CoA carboxylase from both types of soybeans was isolated, as described in Example V. The activity of the enzyme was measured as a function of the time of seed development and the results are shown in FIG. 11.

Figure 11:
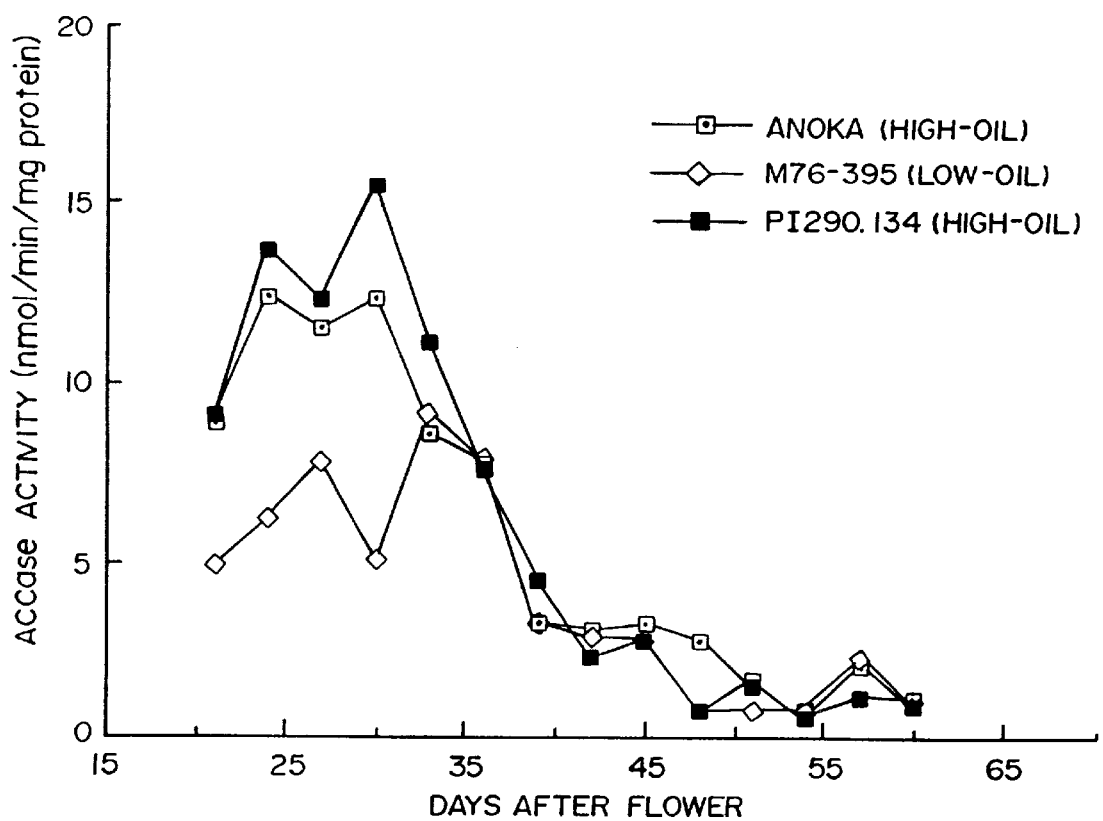
FIG. 11: Graph of ACCase activity during seed development in two high oil soybean cell lines and one low oil soybean cell line.
Figure 12:
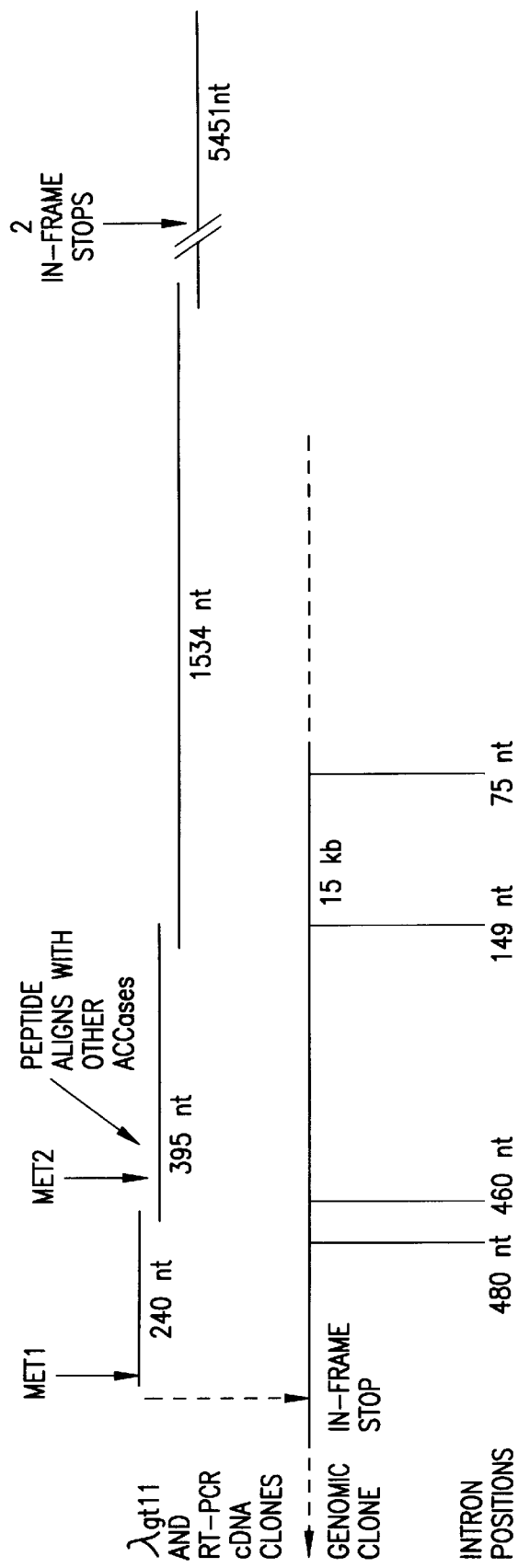
FIG. 12: Cloning strategy to obtain the complete coding sequence of the maize ACCase gene.
Figure 15:
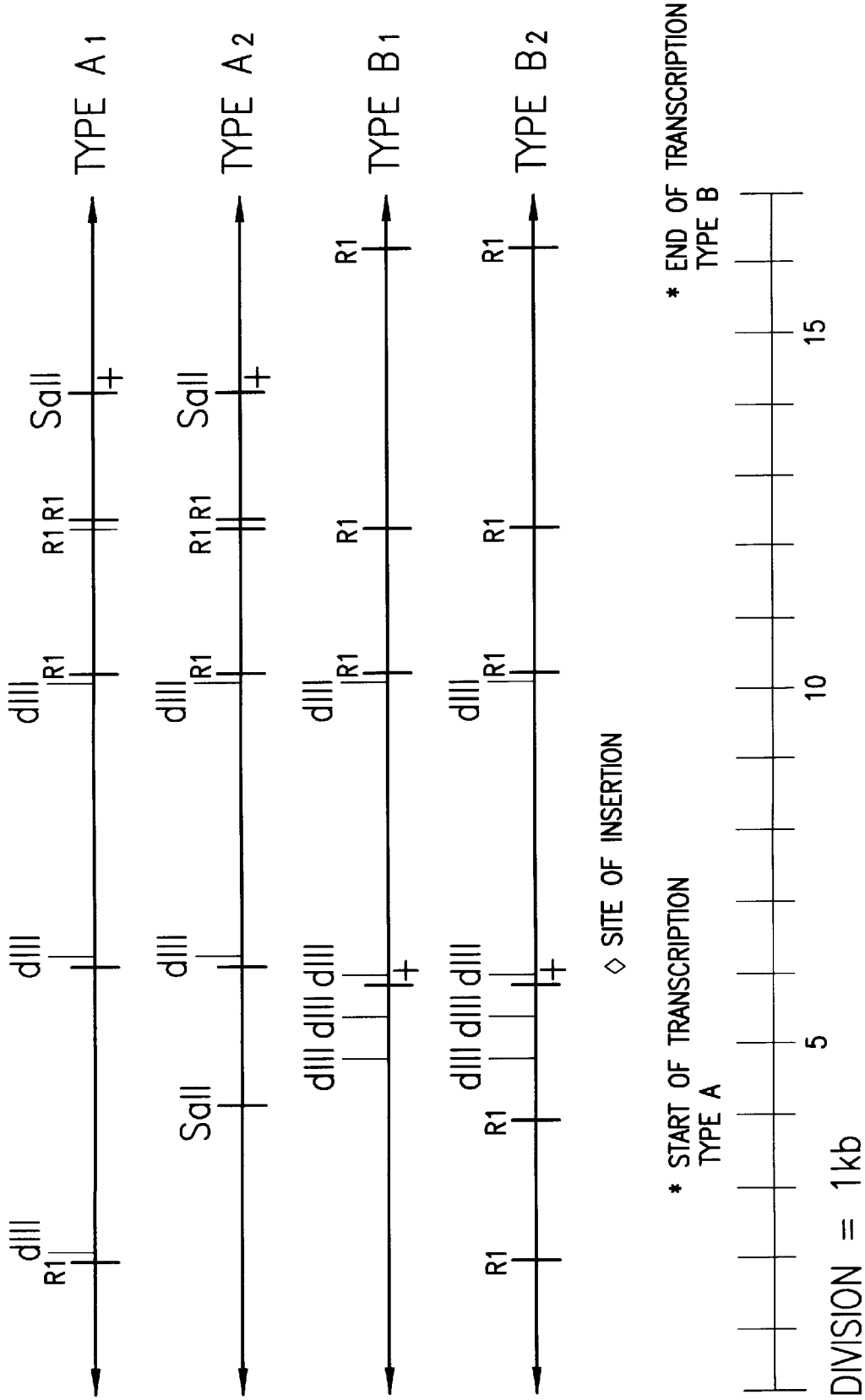
FIG. 15: Restriction map of ACCase genomic clones.

The results in the FIG. 11 indicate that higher oil content soybean is associated with a 2-fold increase in the ACCase activity during early to mid stages of development when compared with a low oil content soybean. Thus, increased expression of the ACCase gene correlates with an increase in the oil content of the seed. Total oil content of the seed was also measured at maturity (60 days). The high oil producing cell lines, Anoka and PI28C. 134, have a total oil content of 21.8% and 19.9%, respectively. In contrast, the low oil soybean line of M76-395, has an oil content of 13.6% oil. Thus, the increase of ACCase expression early in seed development correlates with a higher total oil content in the seed at maturity.

A gene encoding a genomic maize acetyl CoA carboxylase can be isolated, as described in Example V, and used to transform plant species by protoplast or biolistic transformation. If the gene is combined with a strong promoter, such as the 35S cauliflower mosaic virus promoter, overexpression of the ACCase gene is likely. Alternatively, selecting transformed cells with multiple copies of the gene can also result in transformed cells overexpressing the ACCase gene. The gene can be cloned into a vector such as pBI21 or pBI221, as described by Jefferson, cited supra. This vector contains the 35S cauliflower mosaic virus promoter, the β-glucuronidase structural gene, and the nopaline synthase 3' polyadenylation signals. The cloned ACCase gene can replace the β-glucuronidase gene and then be used to transform plant cells, including maize, as described in Example VIII.

Transformed cells can be screened for overproduction of ACCase. The presence of the cloned gene can be verified by identifying the unique restriction enzyme sites incorporated into the cloned gene. ACCase levels can be assessed by standard enzyme assay methods and quantitative Western blots using antibodies specific for maize ACCase. Fatty acid and lipid content in cells lines overproducing ACCase are likely to be elevated and can be assessed using standard methodologies, as described in Clark & Snyder, *JACS*, 66:1316 (1989). Transformed cell lines overproducing ACCase and having increased total oil content will be used to regenerate fertile transgenic plants and seeds, as described in D'Hafluin, cited supra.

EXAMPLE XII

Generation of Transgenic Plants Having an Increase in Plastidic ACCase Activity Maize embryos are transformed with sense and antisense cDNA constructs encoding the plastidic A1 ACCase. Selected transgenic cultures and regenerated transgenic plants and progeny are subjected to detailed analyses of: ACCase transcript levels: activity of ACCase I (plastidic) and ACCase II (presumably cytosolic) in various plant tissues; fatty acid synthesis; lipid accumulation in kernels (primarily embryos); and other plant traits. The culmination of these tests indicates whether plastidic ACCase activity can be modified via transformation and whether fatty acid synthesis is affected.

1. Transformation of maize embryos and plant regeneration

Immature maize embryos of the Hi-II genotype are transformed by particle bombardment according to slight modifications from previously described procedures (Fromm et al., *Biotech.*, 8, 833 (1990); Koziel et al., *Biotech.*, 11, 194 (1993)). This procedure has been employed in transformation studies for bombardment of approximately 15,000 embryos which were then selected for Basta-resistant callus (bar selectable marker gene expression), and regenerated into plants. Transformed (Basta-resistant) plants are obtained from 1–2% of the initial embryos and, when separate plasmids are used for co-transformation, the non-selected transgene is recovered in about 50% of the Basta-resistant plants.

Basta-resistant, hemizygous transformed ($T_0$=F1) plants will be tested by PCR or Southern blots for the presence of A1 ACCase sequences unique to the transformation vector, grown to maturity in growth chambers, greenhouse or field, and self-pollinated when possible, or backcrossed to a nontransformed parent. F2 or backcross progeny are grown in the greenhouse and field and tested for Basta resistance and presence of the A1 ACCase transgene to identify homozygous transgenic plants. Homozygous inbred transgenic lines are then developed.

2. Analysis of ACCase A1 transformants

Plants recovered from at least 100 independent transformation events (i.e., from different bombarded embryos) for both the UBI1 and GLB1 vectors are recovered. Regenerated plants are tested for the presence of the intact ACCase A1 transgene and its cosegregation with the Basta-resistance marker. Homozygous and heterozygous transgenic lines are assayed for total ACCase activity in leaves for UBI1 transformants and in developing embryos (22–26 DAP) for both UBI1 and GLB1 transformants. Sethoxydim and haloxyfop inhibition are used to quickly determine the levels of herbicide-sensitive ACCase I (plastidic) and the herbicide-insensitive ACCase II activity in both leaves and embryos. Increased expression of the ACCase A1 transgene contributes to plastidic ACCase activity and not to ACCase II activity. Kernel fatty acid and oil content are analyzed at maturity and their relationship with ACCase I determined by methods well known to the art.

Transformants that differ in kernel ACCase activity and/or fatty acid and oil content are then selected for more detailed analysis of embryos throughout development (4-day intervals from 16 DAP to maturity). These analyses include RNAse protection assays to determine total A1+A2 transcript levels using a non-specific probe and to determine relative levels of endogenous A1 versus transgene A1 transcripts by use of antisense riboprobes spanning the 5' UTR region of the A1 transgene constructs. Western blots of total proteins separated by SDS-PAGE gels are probed with the ACCase I-specific antibody described hereinabove or with avidin and analyzed by densitometry to distinguish changes in the 227-kD ACCase I and 219-kD ACCase II isoforms. ACCase I activity, fatty acid and lipid content are determined in embryos at each stage of development. These analyses determine whether expression of an additional gene(s) for plastidic ACCase increases ACCase activity and consequently fatty acid and oil content in maize tissues, especially in embryos.

3. Transformation with maize ACCase A1 antisense transformation vectors

Antisense transformation vectors were constructed by blunt-end ligation of nucleotides 1–833 of SEQ ID NO:5 in reverse orientation into multicloning sites of both the GLB1 and UBI1 plasmids. A sense construct with the same 833-bp cDNA sequence also was made with the GLB1 plasmid to serve as a transformation control. Insert orientations were verified by restriction mapping. UBI1 antisense, GLB1 antisense, and GLB1 sense constructs were introduced into >2100, >2900 and >2000 embryos, respectively, and Basta-resistant callus were selected.

If antisense expression results in significant reduction in ACCase activity, it may not be possible to obtain viable callus or plants from the constitutive UBI1 antisense transformants. Similarly, plants transformed with the embryo-specific GLB1 antisense construct may exhibit deleterious effects on embryo development. Thus, failure to obtain transgenic progeny containing the antisense ACCase gene from these transformations may indicate that ACCase activity cannot be downregulated without loss of viability.

4. Analysis of ACCase A1 antisense transformants

All Basta-resistant cultures will be regenerated. The presence of the UBI1 and GLB1 antisense constructs will be determined by PCR analysis for unique transgene sequences such as the Ubi-1 intron/ACCase A1 junction or Glb15' UTR/ACCase A1 junction, or by Southern blotting to detect unique fragments. Plants and lines homozygous or heterozygous for the antisense transgene are analyzed for steady state level of the ACCase A1 antisense transcripts in appropriate tissues/organs (such as leaves, tassels, ears, embryos and endosperm for UBI1; leaves and embryos for GLB1) by using ACCase A1 sense riboprobes for hybridization on RNA blots or for RNAse protection assays. Total ACCase activity (both ACCase I and ACCase II isoforms) and fatty acid and lipid content are determined for the antisense transgenic lines and for corresponding tissues from non-transformed control plants. These analyses show whether ACCase A1 antisense transgenes are expressed in plants and, if so, whether expression is associated with reduced ACCase activity and altered fatty acid and lipid content in maize.

EXAMPLE XIII

Expression of Plastidic and Cytosolic ACCases during Plant Development

Intact embryos are isolated from developing kernels of field-grown inbred B73 at 2 to 4 day intervals between 16–42 DAP and frozen immediately in liquid nitrogen. Samples also are saved for fresh and dry weight determinations. Subsamples from each stage are analyzed for total lipid and fatty acid content. Seedling leaves are sampled along the leaf blade ranging from the etiolated, meristematic basal region to the fully expanded, green tip. Leaves and other tissues (e.g., epidermis) of maize genotypes that accumulate anthocyanin pigments are also analyzed to assess whether a specific ACCase (such as a cytosolic ACCase) is more highly expressed in tissues in which malonyl-CoA also is required as a substrate for chalcone synthase in the flavonoid pathway leading to anthocyanin synthesis.

Gene-specific antisense riboprobes in RNAse protection assays are employed to determine A1, A2, B1 and B2 transcript levels. The corresponding sense transcripts are produced in vitro and used as standards to verify specificity and quantitate the sample transcript levels. Quantitation is done on an AMBIS radioanalytic image system. Herbicide inhibition of total ACCase activity provides an assessment of levels of herbicide-sensitive ACCase I (plastidic) and the herbicide-insensitive ACCase II activity in these tissues. ACCase I and II isoforms are separated by ion-exchange chromatography. Total proteins are separated by SDS-PAGE and Western blots probed with avidin to detect the biotinylated 227-kD ACCase I and 219-kD ACCase II isoforms or probed with ACCase I-specific antibodies.

While the present invention has been described in connection with the preferred embodiment thereof, it will be understood many modifications will be readily apparent to those skilled in the art, and this application is intended to cover any adaptations or variations thereof. It is manifestly intended this invention be limited only by the claims and equivalents thereof.

What is claimed is:

1. A method for altering the oil content of plant cells comprising:

(a) introducing an expression cassette comprising a promoter functional in a plant cell operably linked to a DNA molecule encoding a maize acetyl CoA carboxylase comprising an amino terminal chloroplast transit peptide, into the cells of a plant so as to yield transformed plant cells; and (b) regenerating said transformed plant cells to provide a differentiated transformed plant, wherein expression of the DNA molecule encoding the maize acetyl CoA carboxylase in said plant alters the oil content of the plant cells relative to the oil content in cells of a corresponding untransformed plant.

2. The method according to claim 1, wherein the acetyl CoA carboxylase is expressed in an amount that is greater than that in the untransformed plant.

3. The method according to claim 1, wherein the oil content of the transformed plant cells is increased.

4. The method according to claim 1, wherein the DNA molecule comprises SEQ ID NO:5.

5. The method according to claim 1, wherein the acetyl CoA carboxylase comprises SEQ ID NO:6.

6. The method according to claim 1, wherein the DNA molecule encoding the acetyl CoA carboxylase encodes a variant acetyl CoA carboxylase, wherein the variant acetyl CoA carboxylase has a specific activity which is different from the specific activity of the native acetyl CoA carboxylase.

7. The method of claim 1 wherein the DNA molecule comprises SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or SEQ ID NO:22.

8. A method for altering the oil content of plant cells comprising:
   (a) introducing into plant cells an expression cassette comprising a promoter functional in a plant cell operably linked to a DNA molecule which is complementary to a DNA comprising SEQ ID NO:5, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or SEQ ID NO:22 so as to yield transformed plant cells; and
   (b) regenerating said transformed plant cells to provide a differentiated transformed plant, wherein expression of the DNA molecule in said plant alters the oil content of the plant cells relative to the oil content in the cells of a corresponding untransformed plant.

9. The method according to claim 1 or 8, wherein the promoter is a maize globulin promoter.

10. The method according to claim 1 or 8, wherein the promoter is a maize ubiquitin promoter.

11. A transformed plant prepared by the method of claim 1.

12. A transformed seed of the transformed plant of claim 11.

13. A transformed plant having an altered oil content in its cells comprising a recombinant DNA molecule comprising a promoter functional in a plant cell operably linked to a DNA encoding a maize acetyl CoA carboxylase comprising an amino terminal chloroplast transit peptide, wherein expression of the DNA molecule in the cells of the plant alters the oil content of the plant cells relative to the oil content in the cells of a corresponding untransformed plant.

14. The transformed plant of claim 13, wherein the transformed plant has an increase in oil content in its leaves, seeds, or fruit above that present in a corresponding untransformed plant.

15. The transformed plant of claim 13, wherein the DNA molecule comprises SEQ ID NO:5.

16. The transformed plant of claim 13, wherein the acetyl CoA carboxylase comprises SEQ ID NO:6.

17. The transformed plant of claim 13, wherein the DNA molecule encodes a variant acetyl CoA carboxylase, wherein the variant acetyl CoA carboxylase has a specific activity which is different from the specific activity of the native acetyl CoA carboxylase.

18. The transformed plant of claim 13, which is a dicot.

19. The transformed plant of claim 13, which is a monocot.

20. The plant of claim 13 wherein the DNA molecule comprises SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or SEQ ID NO:22.

21. A transformed seed of the transformed plant of claim 13.

22. A transformed plant having an altered oil content in its cells comprising: a recombinant DNA molecule comprising a promoter functional in a plant cell operably linked to a DNA which is complementary to a DNA comprising SEQ ID NO:5, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or SEQ ID NO:22 wherein expression of the DNA molecule in the cells of the plant alters the oil content of the plant cells relative to the oil content in the cells of a corresponding untransformed plant.

23. The transformed plant of claim 13 or 22, wherein the promoter is a maize globulin promoter.

24. The transformed plant of claim 13 or 22, wherein the promoter is a maize ubiquitin promoter.

25. A transformed plant prepared by the method of claim 8.

26. A transformed seed of the transformed plant of claim 25.

27. The transformed seed of claim 12 or 26, wherein the transformed seed has an altered oil content relative to the oil content of an untransformed seed.

28. The transformed plant of claim 13 or 22, wherein the transformed plant has an altered oil content in its seeds relative to the oil content of an untransformed plant.

29. An expression cassette comprising a maize globulin promoter operably linked to a DNA molecule encoding a maize acetyl CoA carboxylase comprising an amino terminal chloroplast transit peptide.

30. An expression cassette comprising a maize ubiquitin promoter operably linked to a DNA molecule encoding a maize acetyl CoA carboxylase comprising an amino terminal chloroplast transit peptide.

31. The expression cassette of claim 29 or 30 wherein the DNA molecule comprises SEQ ID NO:5, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or SEQ ID NO:22.

32. An expression cassette comprising a maize globulin promoter operably linked to a DNA segment which is complementary to a DNA molecule encoding a maize acetyl CoA carboxylase comprising an amino terminal chloroplast transit peptide.

33. An expression cassette comprising a maize ubiquitin promoter operably linked to a DNA segment which is complementary to a DNA molecule encoding a maize acetyl CoA carboxylase comprising an amino terminal chloroplast transit peptide.

34. The expression cassette of claim 32 or 33 wherein the DNA segment is complementary to a DNA molecule comprising SEQ ID NO:5, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or SEQ ID NO:22.

* * * * *

UNITED STATES PATENT AND TRADEMARK OFFICE
CERTIFICATE OF CORRECTION

PATENT NO. : 6,222,099 B1
DATED : April 24, 2001
INVENTOR(S) : Gengenbach et al.

It is certified that error appears in the above-identified patent and that said Letters Patent is hereby corrected as shown below:

Column 5,
Line 56, delete "comprising)" and insert -- comprising --, therefor.

Column 7,
Line 63, delete "i-i" and insert -- is --, therefor.

Column 12,
Line 9, delete "expressed," and insert -- expressed. --, therefor.

Column 26,
Line 66, delete "Crude a" and insert -- Crude --, therefor.

Signed and Sealed this

Twelfth Day of February, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO.   : 6,222,099 B1
DATED        : April 24, 2001
INVENTOR(S)  : Gengenbach et al.

It is certified that error appears in the above-identified patent and that said Letters Patent is hereby corrected as shown below:

<u>Column 1,</u>
Line 5, please add the following:
--      The invention described herein was made with government support under Grant Number 92-37301-7852, awarded by the National Institutes of Health. The United States Government has certain rights in the invention. --

Signed and Sealed this

Twenty-second Day of October, 2002

*Attest:*

JAMES E. ROGAN
*Director of the United States Patent and Trademark Office*

*Attesting Officer*

UNITED STATES PATENT AND TRADEMARK OFFICE
CERTIFICATE OF CORRECTION

PATENT NO. : 6,222,099 B1
DATED : April 24, 2001
INVENTOR(S) : Gengenbach et al.

It is certified that error appears in the above-identified patent and that said Letters Patent is hereby corrected as shown below:

<u>Column 1,</u>
Line 5, insert
-- The invention described herein was made with government support under Grant Number 92-37301-7852, awarded by the United States Department of Agriculture. The United States Government has certain rights in the invention. --.

Signed and Sealed this

Twenty-eighth Day of January, 2003

JAMES E. ROGAN
*Director of the United States Patent and Trademark Office*